(12) United States Patent
Brown et al.

(10) Patent No.: US 7,897,146 B2
(45) Date of Patent: Mar. 1, 2011

(54) TREATMENT USING HERPES SIMPLEX VIRUS

(75) Inventors: Susanne Moira Brown, Glasgow (GB); Guy Michael Gary Hamilton, Glasgow (GB)

(73) Assignee: Crusade Laboratories Limited, Glasgow, Scotland (GB)

( * ) Notice: Subject to any disclaimer, the term of this patent is extended or adjusted under 35 U.S.C. 154(b) by 0 days.

(21) Appl. No.: 12/065,350

(22) PCT Filed: Aug. 30, 2006

(86) PCT No.: PCT/GB2006/003215
§ 371 (c)(1),
(2), (4) Date: Apr. 18, 2008

(87) PCT Pub. No.: WO2007/026146
PCT Pub. Date: Mar. 8, 2007

(65) Prior Publication Data
US 2009/0010889 A1    Jan. 8, 2009

Related U.S. Application Data

(63) Continuation-in-part of application No. 10/579,606, filed as application No. PCT/GB2004/04851 on Nov. 17, 2004, now Pat. No. 7,498,161.

(30) Foreign Application Priority Data

Nov. 17, 2003  (GB) ................... 0326798.6
Aug. 30, 2005  (GB) ................... 0517617.7
May 11, 2006   (GB) ................... 0609381.9

(51) Int. Cl.
*A01N 63/00* (2006.01)
*A61K 39/12* (2006.01)
*A61K 39/245* (2006.01)
*C12N 15/00* (2006.01)

(52) U.S. Cl. ............... 424/93.1; 424/205.1; 424/231.1; 435/320.1; 435/455; 514/44 R

(58) Field of Classification Search ............... 424/93.1, 424/205.1, 231.1; 435/320.1, 455
See application file for complete search history.

(56) References Cited

U.S. PATENT DOCUMENTS

| 5,922,576 | A  | 7/1999 | He et al. |
| 6,114,146 | A  | 9/2000 | Herlitschka et al. |
| 6,573,090 | B1 | 6/2003 | Breakefield et al. |

FOREIGN PATENT DOCUMENTS

| EP | 0353851  A1 | 2/1990 |
| EP | 0538496  A1 | 4/1993 |
| EP | 0753581  A1 | 1/1997 |
| WO | 93/08288 | 4/1993 |
| WO | 95/04139 | 2/1995 |
| WO | 96/03997 | 2/1996 |
| WO | 96/05291 | 2/1996 |
| WO | 97/04804 | 2/1997 |
| WO | 97/14808 | 4/1997 |
| WO | 97/26904 | 7/1997 |
| WO | 98/51809 | 11/1998 |
| WO | 99/38955 | 8/1999 |
| WO | 99/55345 | 11/1999 |
| WO | 01/16331 A1 | 3/2001 |
| WO | 01/46449 A1 | 6/2001 |
| WO | 01/53506 A2 | 7/2001 |
| WO | 03/018788 A2 | 3/2003 |
| WO | 03/068809 | 8/2003 |
| WO | 2005/049844 | 6/2005 |
| WO | 2005/049845 A2 | 6/2005 |
| WO | 2005/049846 | 6/2005 |
| WO | 2007/132169 | 11/2007 |
| WO | 2008/099189 | 8/2008 |
| WO | 2009/013448 | 1/2009 |

OTHER PUBLICATIONS

Moriuchi et al., (2002, vol. 9, pp. 584-591.*
Concalves et al., 2005, BioEssays, vol. 27, pp. 506-517.*
Haura et al., 2003, Molecular Biotechnology, vol. 25, pp. 139-148.*
Verma et al., 2005, Annu. Rev. Biochem. vol. 74, pp. 711-738.*
Parekh-Olmedo et al., 2005, Gene Therapy, vol. 12, pp. 639-646.*
Bilsland, Alan E., "Selective ablation of human cancer cells by telomerase-specific adenoviral suicide gene therapy vectors expressing bacterial nitroreductase," Oncogene, 2003, vol. 22, pp. 370-380.
Bryant, Christopher, et al., "Cloning, Nucleotide Sequence, and Expression of the Nitroreductase Gene from *Enterobacter cloacae*," The Journal of Biological Chemistry, 1991, vol. 296, pp. 4126-4130.
Coukos, George, et al., "Use of Carrier Cells to Deliver a Replication-selective Herpes Simplex Virus-1 Mutant for the intraperitoneal Therapy of Epithelial Ovarian Cancer," Clinical Cancer Research, 1999, vol. 5, pp. 1523-1537.
Dachs, Gabi U., et al., "From bench to bedside for gene-directed enzyme prodrug therapy of cancer," Anti-Cancer Drugs, 2005, vol. 16, pp. 349-359.
Fu, Xinping, et al., "Expression of a Fusogenic Membrane Glycoprotein by an Oncolytic Herpes Simplex Virus Potentiates the Viral Antitumor Effect," molecular Therapy, 2003, vol. 7, pp. 748-754.
Gomez-Lira, Macarena, et al., "CD45 and multiple sclerosis: the exon 4 C77G polymorphism (additional studies and meta-analysis) and new markers," Journal of Neuroimmunology, 2003, vol. 140, pp. 216-221.

(Continued)

Primary Examiner—Peter Paras, Jr.
Assistant Examiner—David Montanari
(74) Attorney, Agent, or Firm—Swanson & Bratschun, L.L.C.

(57) ABSTRACT

The use of Herpes Simplex Virus (HSV) in the treatment of tumour by extratumoural administration of HSV, and the use of HSV in treatment of tumour by combination therapy with a pharmaceutical wherein the HSV and/or pharmaceutical is administered at an extratumoural location, is disclosed.

22 Claims, 36 Drawing Sheets

OTHER PUBLICATIONS

Figure 1:
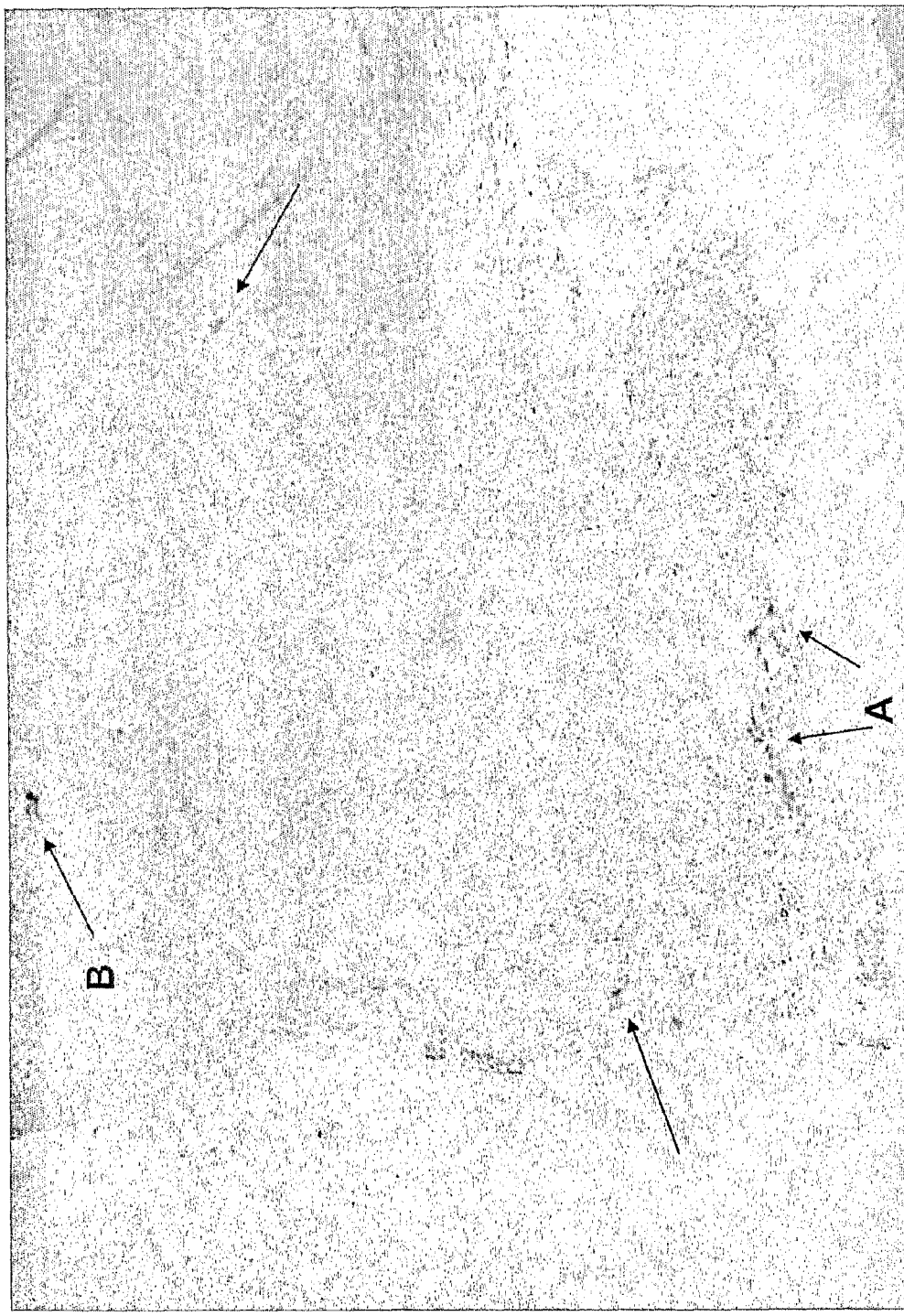

Goncalves, Manuel A.F.V., "A concise peer into the background, initial thoughts and practices of human gene therapy," BioEssays, 2005, vol. 27, pp. 506-517.

Haura, Eric B., "Gene Therapy for Lung Cancer," Molecular Biotechnology, 2003, vol. 25, pp. 139-148.

Jorgensen, Timothy J., "Ionizing Radiation Does Not Alter the Antitumor Activity of Herpes Simplex Virus Vector G207 in Subcutaneous Tumor Models of Human and Murine Prostate Cancer," Neoplasia, vol. 3, pp. 451-456.

Liu, B.L., et al., "ICP34.5 deleted herpes simplex virus with enhanced oncolytic, immune stimulating, and anti-tumour properties," Gene Therapy, 2003, vol. 10, pp. 292-303.

Markert, J.M., "Conditionally replicating herpes simplex virus mutant, G207 for the treatment of malignant glioma: results of a phase I trial," Gene Therapy, 2000, vol. 7, pp. 867-874.

McNeish, I.A., et al., "Virus directed enzyme prodrug therapy for ovarian and pancreatic cancer using retrovirally delivered E. coli nitroreductase and CB1954," Gene Therapy, 1998, vol. 5, pp. 1061-1069.

Moriuchi, S., et al., "Double suicide gene therapy using a replication defective herpes simplex virus vector reveals reciprocal interference in a malignant glioma model," Gene Therapy, 2002, vol. 9, pp. 584-591.

Nakamori, Mikihito, et al., "Effective Therapy of Metastatic Ovarian Cancer with an Oncolytic Herpes Simplex Virus Incorporating Two Membrane Fusion Mechanisms," Clinical Cancer Research, 2003, vol. 9, pp. 2727-2733.

Nakamori, Mikihito, et al., "Potent Antitumor Activity After Systemic Delivery of a Doubly Fusogenic Oncolytic Herpes Simplex Virus Against Metastatic Prostate Cancer," The Prostate, 2004, vol. 60, pp. 53-60.

Palmer, Daniel H., et al. "Virus-Directed Enzyme Prodrg Therapy: Intratumoral Administration of a Replication-Deficient Adenovirus Encoding Netroreductase to Patients with Resectable Liver Cancer," Journal of Clinical Oncology, 2004, vol. 22, pp. 1546-1552.

Parekh-Olmedo, H., et al., "Gene therapy progress and prospects: targeted gene repair," Gene Therapy, 2005, vol. 12, pp. 639-646.

Perna, Nicole T., et al., "Genome sequence of enterohaemorrhagic Escherichia coli 0157:H7," Nature, 2001, vol. 409, pp. 529-533.

Toyoizumi, Takane, et al., "Combined Therapy with Chemotherapeutic Agents and Herpes Simplex Virus Type 1 ICP34.5 Mutant (HSV-1716) in Human Non-Small Cell Lung Cancer," Human Gene Therapy, 1999, vol. 10, pp. 3013-3029.

Varghese, Susan; Rabkin, Samuel D., "Oncolytic herpes simplex virus vectors for cancer virotherapy," Cancer Gene Therapy, 2002, vol. 9, pp. 967-978.

Verma, Inder M., et al., "Gene Therapy: Twenty-First Century Medicine," Annual Review of Biochemistry, 2005, vol. 74, pp. 711-738.

Walker, Jonathan R., et al. "Local and Systemic Therapy of Human Prostate Adenocarcinoma with the Conditionally Replicating Herpes Simplex Virus Vector G207," Human Gene Therapy, 1999, vol. 10, pp. 2237-2243.

Watanabe, Masahiko, et al., "Nucleotide sequence of Salmonella typhimurium nitroreductase gene," Nucleic Acids Research, Submitted Jan. 5, 1990, vol. 18, No. 4, p. 1059.

Weedon, Sarah J., et al., "Sensitisation of Human Carcinoma Cells to the Prodrug CB1954 by Adenovirus Vector-Mediated Expression of E. coli Nitroreductase," International Journal of Cancer, 2000, vol. 86, pp. 848-854.

Wong, Richard J., et al., "Oncolytic Herpesvirus Effectively Treats Murine Squamous Cell Carcinoma and Spreads by Natural Lymphatics to Treat Sites of Lymphatic Metastases," Human Gene Therapy, 2002, vol. 13, pp. 1213-1223.

Chou et al. (1990) Science, 250:1262-1266, "Mapping of herpes simplex virus-1 neurovirulence to $_{\gamma 1}34.5$, a gene nonessential for growth in culture".

Kucharczuk et al (1997) Cancer Research, 57:466-471, "Use of a "Replication-Restricted" Herpes Virus to Treat Experimental Human Malignant Mesothelioma".

Lovering et al. (2001) J. Mol. Biol. 309:203-213, "The structure of Escherichia coli nitroreductase complexed with nicotinic acid: three crystal forms at 1.7 A, 1.8 A and 2.4 A resolution".

Liu et al (2003) Gene Therapy 10:292-303 "ICP34.5 deleted herpes simplex virus with enhanced oncolytic, immune stimulating, and anti-tumour properties".

Mackie et al (2001) The Lancet 357:525 "Intralesional injection of herpes simplex virus 1716 in metastatic melanoma".

MacLean et al. (1991) Journal of General Virology, 72:631-639, "Herpes simplex virus type 1 deletion variants 1714 and 1716 pinpoint neurovirulence-related sequences in Glasgow strain 17[+] between immediate early gene 1 and the 'a' sequence".

Parkinson et al. (2000) J. Med. Chem. 43:3624-3631, "Crystal structure of FMN-dependent nitroreductase from Escherichia coli B: a prodrug-activating enzyme".

Randazzo et al (1997) J. Invest Dermatol 108:933-937, "Treatment of Experimental Subcutaneous Human Melanoma with a Replication-Restricted Herpes Simplex Virus Mutant".

Toda et al (1998) Human Gene Therapy 9:2177-2185, "Treatment of Human Breast Cancer in a Brain Metastatic Model by G207, a Replication-Competent Multimutated Herpes Simplex Virus I".

Senzer et al (Poster from ASCO 2009: "Updated Results of a Phase II Clinical Trial with a Second Generation, Enhanced Potency, Immune-enhanced, Oncolytic Herpesvirus in Unresectable Metastatic Melanoma".

Randazzo et al. (1995) Virology 211(1): 94-101, "Treatment of experimental intracranial murine melanoma with a neuroattenuated herpes simplex virus 1 mutant".

* cited by examiner

Figure 5:
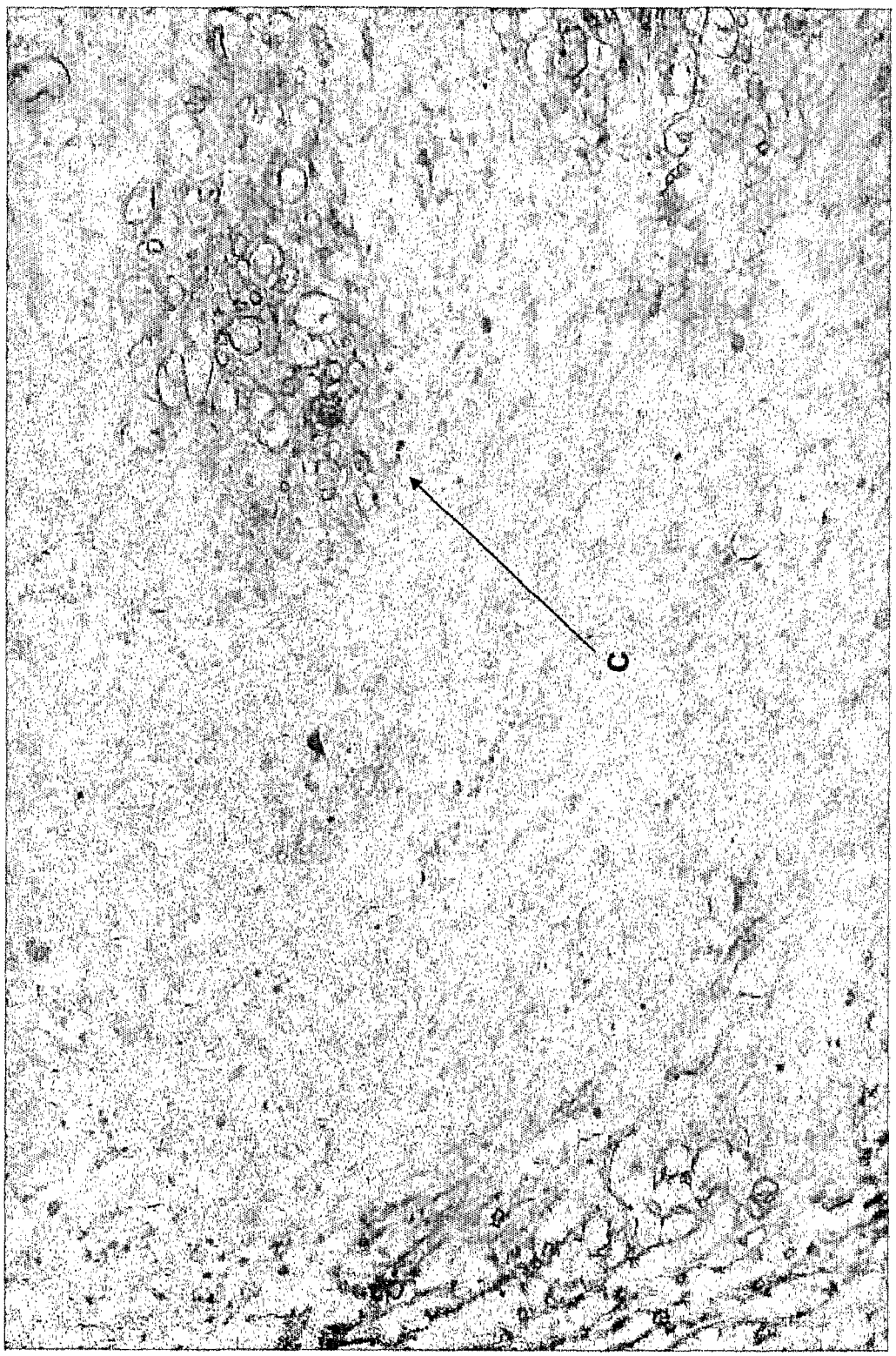
Figure 6:
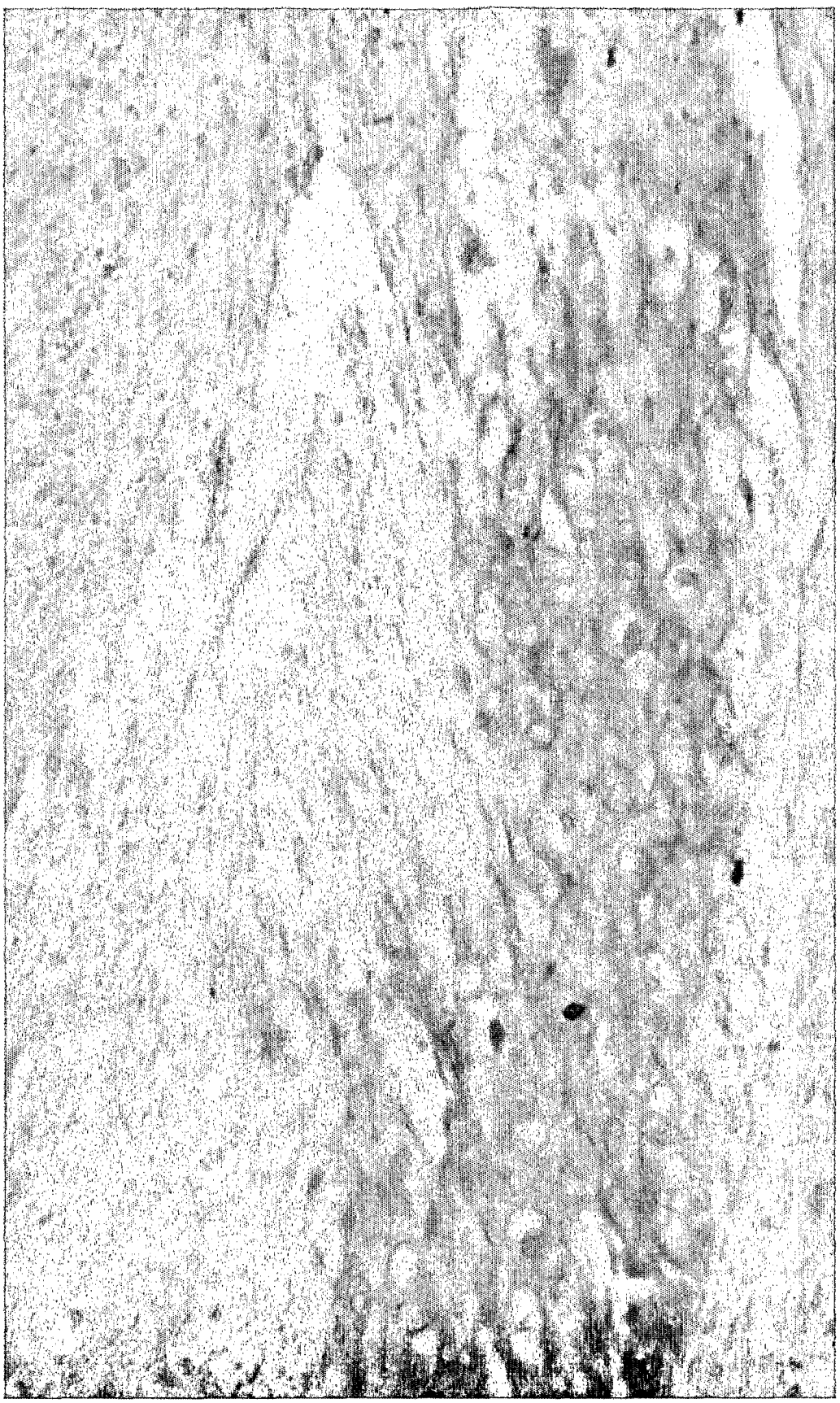

| Fig 5 L | | DNA | DNA | RNA | RNA |
|---|---|---|---|---|---|
| Sample | Day | HSV | NTR | HSV | NTR |
| Tumour | 1 | + | - | ++ | - |
| Blood | 1 | - | - | NI | - |
| Brain | 1 | - | - | - | - |
| Skin | 1 | - | - | - | - |
| Lung | 1 | - | - | - | - |
| Kidney | 1 | - | - | - | - |
| Gut | 1 | - | - | - | - |
| Spleen | 1 | +++ | - | - | - |
| heart | 1 | | - | + | - |
| liver | 1 | - | - | - | - |
| Tumour | 7 | +++ | +++ | +++ | ++ |
| Blood | 7 | - | - | NI | NI |
| Brain | 7 | - | - | - | - |
| Skin | 7 | - | + | - | - |
| Lung | 7 | - | - | - | - |
| kidney | 7 | - | - | - | - |
| Gut | 7 | - | - | - | - |
| Spleen | 7 | - | - | - | - |
| Heart | 7 | - | - | - | - |
| liver | 7 | - | - | - | - |

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
acgacgacgt ccgacggcga                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic
```

<400> SEQUENCE: 2
gtgctggtgc tggacgacac                          20

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
ctttcacatt gagtcattat gg                       22

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
ttacacttcg gttaaggtga tg                       22

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
cgtgaaaaga tgacccaga                           19

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
agcatagccc tcgtagatg                           19

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
acgacgacgt ccgacggcga                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
gtgctggtgc tggaggacac                          20

<210> SEQ ID NO 9

```
<211> LENGTH: 21
<212> TYPE: DNA
<213> ORGANISM: Artificial Sequence
<220> FEATURE:
<223> OTHER INFORMATION: Synthetic

<400> SEQUENCE: 9
tttcacattg agtcattatg g                                               21

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
ttacacttcg gttaaggtga tg                                              22
```

TREATMENT USING HERPES SIMPLEX VIRUS

RELATED APPLICATIONS

This application is a 35 U.S.C. §371 national phase application of PCT/GB2006/003215 (WO 2007/026146) filed on Aug. 30, 2006 entitled "Treatment Using Herpes Simplex Virus", which application claims the benefit of Great Britain Application Serial No. 0517617.7 filed Aug. 30, 2005 and also claims the benefit of Great Britain Application Serial No. 0609381.9 filed May 11, 2006, each of which are incorporated herein by reference in their entirety; this application is also a continuation-in-part of U.S. patent application Ser. No. 10/579,606 filed May 16, 2006 entitled "Mutant Viruses" which is a 35 U.S.C. §371 national phase application of PCT/GB2004/04851 filed on Nov. 17, 2004 which claims priority to Great Britain Application Serial No. 0326798.6 filed on Nov. 17, 2003, each of which is incorporated herein by reference in their entirety.

FIELD OF THE INVENTION

The present invention relates to the treatment of cancer using herpes simplex virus.

Incorporated by reference herein in its entirety is the Sequence Listing entitled "sequence Listing.txt," created Sep. 29, 2010, size of 3 kilobytes.

BACKGROUND TO THE INVENTION

The herpes simplex virus (HSV) genome comprises two covalently linked segments, designated long (L) and short (S). Each segment contains a unique sequence flanked by a pair (terminal and internal) of inverted repeat sequences. The long repeat (RL or $R_L$) and the short repeat (RS or $R_S$) are distinct.

The HSV ICP34.5 (also γ34.5) gene, which has been extensively studied[1,6,7,8], has been sequenced in HSV-1 strains F[9] and syn17+[3] and in HSV-2 strain HG52[4]. One copy of the ICP34.5 gene is located within each of the $R_L$ repeat regions. Mutants inactivating both copies of the ICP34.5 gene (i.e. null mutants), e.g. HSV-1 strain 17 mutant 1716[2] (HSV 1716) or the mutants R3616 or R4009 in strain F[5], are known to lack neurovirulence, i.e. be avirulent, and have utility as both gene delivery vectors or in the treatment of tumours by oncolysis. HSV-1 strain 17 mutant 1716 has a 759 bp deletion in each copy of the ICP34.5 gene located within the BamHI s restriction fragment of each RL repeat.

ICP34.5 null mutants of HSV-1 strain 17 have consistently shown much better clinical oncolytic efficacy than mutants in other HSV strains, such as strain F, to the extent that some strain 17 mutants are now in advanced stage clinical trials for the treatment of tumour. Strain 17 ICP34.5 null mutants are additionally advantageous over those of other strains in that they achieve clinical efficacy when administered directly to tumours at dosages that are one or more logs lower than those required to achieve a comparable effect using mutants of other strains.

HSV 1716 is one example of such a mutant and is described in WO 92/13943[2], specifically incorporated herein by reference. HSV 1716 has been deposited on 28 Jan. 1992 at the European Collection of Animal Cell Cultures, Vaccine Research and Production Laboratories, Public Health Laboratory Services, Porton Down, Salisbury, Wiltshire, SP4 0JG, United Kingdom under accession number V92012803 in accordance with the provisions of the Budapest Treaty on the International Recognition of the Deposit of Microorganisms for the Purposes of Patent Procedure (herein referred to as the 'Budapest Treaty').

HSV1716/CMV-NTR/GFP (referred to herein as HSV 1790) is another exemplary ICP34.5 null mutant of HSV-1 strain 17. This virus is an engineered herpes simplex virus ICP34.5 null mutant which expresses the nitroreductase (NTR) gene and is described in WO 2005/049845[14], specifically incorporated herein by reference. It is modified in each ICP34.5 locus by insertion of the E. coli nitroreductase (NTR) gene which disrupts the ICP34.5 protein coding sequence such that the virus lacks a functional ICP34.5 protein. The virus is ICP34.5 deficient, non-neurovirulent and exhibits good oncolytic properties.

In HSV 1790 the NTR gene is operably linked to a transcription control element permitting expression of the NTR gene. As such the virus may be used in gene therapy techniques wherein the virus acts as a vector for the expression of NTR in an HSV infected cell. NTR is capable of converting a range of prodrug molecules, such as CB1954, into cytotoxic active pharmaceutical agents. Thus, HSV1790 can be used in targeted combination therapy in which the oncolytic ability of HSV1790 is combined with localised prodrug activation in tumour cells. HSV 1790 has been deposited (under the name HSV1716/CMV-NTR/GFP) in the name of Crusade Laboratories Limited having an address at Department of Neurology Southern General Hospital 1345 Govan Road Govan Glasgow G51 5TF Scotland on 05 Nov. 2003 at the European Collection of Cell Cultures (ECACC), Health Protection Agency, Porton Down, Salisbury, Wiltshire, SP4 0JG, United Kingdom under accession number 03110501 in accordance with the provisions of the Budapest Treaty on the International Recognition of the Deposit of Microorganisms for the Purposes of Patent Procedure (herein referred to as the 'Budapest Treaty').

To date, the treatment of tumours using ICP34.5 deficient HSV has relied upon direct introduction of the HSV to the tumour, usually by intratumoral injection. This has been considered necessary in order to ensure that the HSV reaches its intended target, i.e. the tumour that is to be treated. Moreover, this approach reduces the risks associated with introduction of a viral vector into healthy tissue in as far as the lytic capacity of the virus is focused on the tumour.

It is well known that tumours may occur in virtually any tissue and at virtually any position in the body. As such it can often be procedurally difficult, as well as the cause of considerable discomfort and possible risk to the patient, to deliver the HSV directly to the tumour. Accordingly, it would be of significant clinical benefit if the oncolytic effect of these HSV could be obtained without having to administer the HSV directly to the tumour. However, the ability of a clinically efficacious oncolytic HSV that is administered to a patient's healthy tissue to successfully and selectively target and lyse tumour tissue located elsewhere in the body, and which does not exhibit serious disadvantageous side-effects on the patient's healthy tissue, remains uncertain.

SUMMARY OF THE INVENTION

The inventors have now shown that oncolytic HSV of strain 17 administered systemically at a site distal from a tumour may be used to treat the tumour without causing damaging side effects to the patient being treated.

In particular, the inventors have shown that successful tumour treatment may be obtained by intravenous administration of the HSV, i.e. to the circulating blood. These results demonstrate that oncolytic HSV of strain 17 introduced to healthy tissue may circulate in the body to target and treat the cancerous tissue without pathologically infecting or lysing the intervening healthy tissue.

This finding represents a significant advance in clinical HSV oncolytic therapy and provides the basis for considerable improvements in clinical efficacy, procedure and risk management, as well as in patient comfort.

At its most general the present invention relates to the use of an HSV to treat a cancerous condition in a patient in need of treatment, wherein the HSV is administered to the patient at a location that is outside of the cancerous condition that is to be treated.

The administration may therefore be extratumoral or extraneoplastic, i.e. where the HSV is not administered directly to the tumour or neoplastic tissue that is to be treated. Such administration may involve administration of the HSV to a tissue in which a tumour or neoplasia to be treated is not present.

Administration may be systemic, i.e. wherein substantially the entire body is exposed to the HSV, rather than only the cancerous tissue that requires treatment. This may be achieved by a route of administration that permits the HSV to circulate in one of the body's circulating fluids, e.g. the blood, lymph or spinal fluid.

Preferably, administration of the HSV is such that the HSV can be transported within the body to a cancerous condition that requires treatment. This may involve transport to more than one site of the cancerous condition, e.g. to two or more tumours, for the treatment of one or more of those tumours. In that respect, the HSV may be considered to be indirectly administered to the cancerous condition. Administration to the blood may be particularly preferred (e.g. by intravenous and/or intra-arterial administration). This route of administration may be preferred for the treatment of any cancerous condition, but optionally it may exclude blood cancers, e.g. leukaemia.

Administration to other circulating fluids such as to the lymph fluid, through administration to the lymphatic system, or to the spinal fluid may also be preferred for the treatment of any cancerous condition, but optionally excluding cancers of the lymph fluid and/or of the lymphatic system (e.g. lymphoma) or of the spinal fluid and/or spinal column respectively.

According to one aspect of the present invention an herpes simplex virus (HSV) is provided for use in the treatment of a tumour by extratumoural administration of said HSV.

According to another aspect of the present invention the use of an herpes simplex virus (HSV) in the manufacture of a medicament for use in the treatment of a tumour by extratumoural administration of said HSV is provided.

According to a further aspect of the present invention an herpes simplex virus (HSV) is provided for use in the treatment of a cancerous condition in a patient by administration of said HSV to the patient's blood.

According to another aspect of the present invention the use of an herpes simplex virus (HSV) in the manufacture of a medicament for use in the treatment of a cancerous condition in a patient by administration of said HSV to the patient's blood is provided.

In another aspect of the present invention there is provided a method of treating a tumour in a patient in need of treatment thereof, said method comprising the step of administering an herpes simplex virus (HSV) to said patient at an extratumoural location on or in the patient's body.

In a further aspect of the present invention there is provided a method of treating a cancerous condition in a patient in need of treatment thereof, said method comprising the step of administering an herpes simplex virus (HSV) to the patient's blood.

In another aspect of the present invention there is provided a kit of parts for use in treating a tumour in a patient, said kit comprising a container containing an herpes simplex virus (HSV) and instructions for the administration of said HSV to a patient in need of treatment at an extratumoural location in order to treat the tumour.

In yet another aspect of the present invention there is provided a kit of parts for use in treating a cancerous condition in a patient comprising a container containing an herpes simplex virus (HSV) and instructions for the administration of said HSV to a patient's blood in order to treat a cancerous condition of the patient.

The instructions for administration may include information on suitable HSV dosages.

The inventors have also found that that the ability of systemically (extratumourally) administered HSV to preferentially target and infect cancerous cells may be used in combination with a pharmaceutical or medicament to treat a cancerous condition. As the pharmaceutical may also be administered systemically this provides a significant advance in the available treatments. Such combination therapy may also provide for therapeutic improvements owing to the potential synergistic effect provided by the combination.

Therefore, further aspects of the present invention concern the use of HSV according to the invention in combination with a pharmaceutical or medicament, preferably a chemotherapeutic drug or activatable prodrug, in the treatment of a cancerous condition.

Accordingly, in a further aspect of the present invention an herpes simplex virus (HSV) is provided for use in the treatment of a tumour by combination therapy with a pharmaceutical, wherein the HSV and/or pharmaceutical is administered at an extratumoural location.

In another aspect of the present invention a pharmaceutical is provided for use in the treatment of a tumour by combination therapy with an herpes simplex virus (HSV), wherein the HSV and/or pharmaceutical is administered at an extratumoural location.

According to a further aspect of the present invention an herpes simplex virus (HSV) is provided for use in the treatment of a cancerous condition by combination therapy with a pharmaceutical, wherein the HSV and/or pharmaceutical is administered to the patient's blood.

According to a further aspect of the present invention a pharmaceutical is provided for use in the treatment of a cancerous condition by combination therapy with an herpes simplex virus (HSV), wherein the HSV and/or pharmaceutical is administered to the patient's blood.

In another aspect of the present invention products are provided containing an herpes simplex virus (HSV) and a pharmaceutical as a combined preparation for simultaneous, separate, or sequential use in the treatment of a tumour wherein the HSV and/or pharmaceutical is administered at an extratumoural location.

According to a further aspect of the present invention products are provided containing an herpes simplex virus (HSV) and a pharmaceutical as a combined preparation for simultaneous, separate, or sequential use in the treatment of a cancerous condition wherein the HSV and/or pharmaceutical is administered to the patient's blood.

In another aspect of the present invention the use of an herpes simplex virus (HSV) in the manufacture of a medicament for treatment of a tumour by combination therapy of said medicament with a pharmaceutical, wherein the HSV and/or pharmaceutical is administered at an extratumoural location, is provided.

In another aspect of the present invention the use of a pharmaceutical in the manufacture of a medicament for treatment of a tumour by combination therapy of said medicament with an herpes simplex virus (HSV), wherein the HSV and/or medicament is administered at an extratumoural location, is provided.

According to a further aspect of the present invention the use of an herpes simplex virus (HSV) in the manufacture of a medicament for treatment of a cancerous condition by combination therapy of said medicament with a pharmaceutical, wherein the HSV and/or pharmaceutical is administered to the patient's blood, is provided.

According to a further aspect of the present invention the use of a pharmaceutical in the manufacture of a medicament for treatment of a cancerous condition by combination therapy of said medicament with an herpes simplex virus (HSV), wherein the HSV and/or medicament is administered to the patient's blood, is provided.

In another aspect of the present invention a method of treating a tumour is provided comprising the steps of administering to an individual in need of treatment a therapeutically effective amount of an herpes simplex virus (HSV) and a pharmaceutical, wherein the HSV and/or pharmaceutical is administered at an extratumoural location.

According to a further aspect of the present invention a method of treating a cancerous condition is provided comprising the steps of administering to an individual in need of treatment a therapeutically effective amount of an herpes simplex virus (HSV) and a pharmaceutical, wherein the HSV and/or pharmaceutical is administered to the patient's blood.

In another aspect of the present invention a kit of parts is provided for use in the treatment of a tumour by combination therapy, the kit comprising a first container comprising an herpes simplex virus (HSV) and a second container comprising a pharmaceutical, together with instructions for the extratumoural administration of the HSV and/or pharmaceutical.

According to a further aspect of the present invention a kit of parts is provided for use in the treatment of a cancerous condition by combination therapy, the kit comprising a first container comprising an herpes simplex virus (HSV) and a second container comprising a pharmaceutical, together with instructions for administration of the HSV and/or pharmaceutical to the patient's blood.

In preferred embodiments the HSV genome encodes an exogenous/heterologous (non-HSV originating) polypeptide/protein such as NTR that may be expressed by the HSV following infection of cells in vitro and/or in vivo, particularly tumour or other cancerous cells in vivo (e.g. in a patient requiring treatment). The expressed polypeptide and pharmaceutical are preferably capable of interacting, directly or indirectly, to produce a therapeutic effect, which may be enhanced as compared to the therapeutic effect of the HSV or pharmaceutical alone.

In particularly preferred embodiments, the pharmaceutical is an activatable prodrug and the exogenous polypeptide/protein is capable of converting the prodrug to a therapeutically active pharmaceutical. In one particularly preferred embodiment the expressed polypeptide/protein is an NTR and the prodrug is an NTR prodrug, such as CB1954. Accordingly, the HSV may be HSV1790. This therapeutic approach may be referred to as gene directed enzyme-prodrug therapy (GDEPT).

Accordingly, the following further aspects of the invention are also provided.

According to one further aspect of the present invention an herpes simplex virus (HSV) is provided for use in the treatment of a tumour by combination therapy with an activatable prodrug, wherein the HSV and/or activatable prodrug is administered at an extratumoural location, and wherein the HSV genome encodes a polypeptide/protein capable of converting the activatable prodrug to a therapeutically active pharmaceutical.

In another aspect of the present invention an activatable prodrug is provided for use in the treatment of a tumour by combination therapy with an herpes simplex virus (HSV), wherein the HSV and/or activatable prodrug is administered at an extratumoural location, and wherein the HSV genome encodes a polypeptide/protein capable of converting the activatable prodrug to a therapeutically active pharmaceutical.

According to a further aspect of the present invention an herpes simplex virus (HSV) is provided for use in the treatment of a cancerous condition by combination therapy with an activatable prodrug, wherein the HSV and/or activatable prodrug is administered to the patient's blood, and wherein the HSV genome encodes a polypeptide/protein capable of converting the activatable prodrug to a therapeutically active pharmaceutical.

According to a further aspect of the present invention an activatable prodrug is provided for use in the treatment of a cancerous condition by combination therapy with an herpes simplex virus (HSV), wherein the HSV and/or activatable prodrug is administered to the patient's blood, and wherein the HSV genome encodes a polypeptide/protein capable of converting the activatable prodrug to a therapeutically active pharmaceutical.

In another aspect of the present invention products are provided containing an herpes simplex virus (HSV) and an activatable prodrug as a combined preparation for simultaneous, separate, or sequential use in the treatment of a tumour wherein the HSV and/or activatable prodrug is administered at an extratumoural location, and wherein the HSV genome encodes a polypeptide/protein capable of converting the activatable prodrug to a therapeutically active pharmaceutical.

According to a further aspect of the present invention products are provided containing an herpes simplex virus (HSV) and an activatable prodrug as a combined preparation for simultaneous, separate, or sequential use in the treatment of a cancerous condition wherein the HSV and/or activatable prodrug is administered to the patient's blood, and wherein the HSV genome encodes a polypeptide/protein capable of converting the activatable prodrug to a therapeutically active pharmaceutical.

In another aspect of the present invention the use of an herpes simplex virus (HSV) in the manufacture of a medicament for treatment of a tumour by combination therapy of said medicament with an activatable prodrug is provided, wherein the HSV and/or activatable prodrug is administered at an extratumoural location, and wherein the HSV genome encodes a polypeptide/protein capable of converting the activatable prodrug to a therapeutically active pharmaceutical.

In another aspect of the present invention the use of an activatable prodrug in the manufacture of a medicament for treatment of a tumour by combination therapy of said medicament with an herpes simplex virus (HSV) is provided, wherein the HSV and/or activatable prodrug is administered at an extratumoural location, and wherein the HSV genome encodes a polypeptide/protein capable of converting the activatable prodrug to a therapeutically active pharmaceutical.

According to a further aspect of the present invention the use of an herpes simplex virus (HSV) in the manufacture of a medicament for treatment of a cancerous condition by combination therapy of said medicament with an activatable prodrug is provided, wherein the HSV and/or activatable prodrug is administered to the patient's blood, and wherein the HSV genome encodes a polypeptide/protein capable of converting the activatable prodrug to a therapeutically active pharmaceutical.

According to a further aspect of the present invention the use of an activatable prodrug in the manufacture of a medicament for treatment of a cancerous condition by combination therapy of said medicament with an herpes simplex virus (HSV) is provided, wherein the HSV and/or activatable prodrug is administered to the patient's blood, and wherein the HSV genome encodes a polypeptide/protein capable of converting the activatable prodrug to a therapeutically active pharmaceutical.

In another aspect of the present invention a method of treating a tumour is provided comprising the steps of administering to an individual in need of treatment a therapeutically effective amount of an herpes simplex virus (HSV) and an activatable prodrug, wherein the HSV and/or activatable prodrug is administered at an extratumoural location, and wherein the HSV genome encodes a polypeptide/protein capable of converting the activatable prodrug to a therapeutically active pharmaceutical.

According to a further aspect of the present invention a method of treating a cancerous condition is provided comprising the steps of administering to an individual in need of treatment a therapeutically effective amount of an herpes simplex virus (HSV) and an activatable prodrug, wherein the HSV and/or activatable prodrug is administered to the patient's blood, and wherein the HSV genome encodes a polypeptide/protein capable of converting the activatable prodrug to a therapeutically active pharmaceutical.

In another aspect of the present invention a kit of parts is provided for use in the treatment of a tumour by combination therapy, the kit comprising a first container comprising an activatable prodrug and a second container comprising an herpes simplex virus (HSV) wherein the HSV genome encodes a polypeptide/protein capable of converting the activatable prodrug to a therapeutically active pharmaceutical, together with instructions for the extratumoural administration of the HSV and/or activatable prodrug.

According to a further aspect of the present invention a kit of parts is provided for use in the treatment of a cancerous condition by combination therapy, the kit comprising a first container comprising an activatable prodrug and a second container comprising an herpes simplex virus (HSV) wherein the HSV genome encodes a polypeptide/protein capable of converting the activatable prodrug to a therapeutically active pharmaceutical, together with instructions for administration of the HSV and/or pharmaceutical to the patient's blood.

In preferred embodiments, both the HSV and pharmaceutical are administered to the patient at a location that is outside of the cancerous condition that is to be treated, i.e. extratumoural. For example, administration may be systemic into any circulating fluid, e.g. to the blood by intravenous administration. In another embodiment, one of the HSV or pharmaceutical may be administered extratumourally, with the other being administered directly to the tumour, e.g. by injection.

In terms of route of administration, the HSV and pharmaceutical may be administered either by the same route of administration, e.g. both intravenously, or by separate routes of administration, e.g. one intravenously and the other intraperitoneal.

In order to provide a 'combination therapy', therapeutically effective amounts of the HSV and pharmaceutical should be present in the body. This may be achieved by simultaneous, separate or sequential administration of the HSV and pharmaceutical. Where the HSV and pharmaceutical are not administered simultaneously the time period between administration of the first and second compounds may be predetermined such that the HSV, or a polypeptide/protein encoded by the HSV genome, and pharmaceutical are present in active form in the patient's body at the same time in order that they may directly or indirectly interact and provide a therapeutic benefit, which may optionally involve a synergistic effect of the HSV (and/or the polypeptide/protein encoded by the HSV genome) and pharmaceutical. Preferred time periods may be less than 15 minutes, less than one hour, two hours, three hours, four hours, five hours or six hours, twelve hours, twenty four hours, forty eight hours, one week or two weeks. Either the herpes simplex virus or pharmaceutical may be administered first.

The administered pharmaceutical may comprise a therapeutically active compound, or a pharmaceutically acceptable salt or ester thereof. In some preferred embodiments of the invention the pharmaceutical is administered in the form of an activatable prodrug, e.g. an NTR prodrug. An activatable prodrug may not be therapeutically active, e.g. as a chemotherapeutic, or may be only partially active. Preferably, the prodrug may be converted to a therapeutically active pharmaceutical form in the body, e.g. to a chemotherapeutic form. In preferred embodiments, the prodrug requires a factor, preferably an enzyme or protein, to be present for conversion to occur. This factor is preferably encoded by the HSV and expressed in cells infected by the HSV. This system provides a means of highly effective targeting of the active pharmaceutical form to cells infected by the HSV. HSV modified so as to be capable of targeting specific cells and tissues are described in PCT/GB2003/000603 (WO 03/068809), hereby incorporated in its entirety by reference.

Preferably the administered HSV is non-neurovirulent. The HSV is also preferably oncolytic. More preferably the HSV is modified in at least one of the long repeat regions ($R_L$) of the HSV genome, relative to the genome of the corresponding wild-type strain, such that the HSV lacks neurovirulence. The modification may be within the BamHI s restriction fragment of one or each $R_L$ repeat. As such, the HSV genome may be modified within the Bam HI s region of the internal repeat $R_L$ (0.81-0.83 mu) and within the counterpart region of the terminal $R_L$ (0-0.02 mu) such that the variant lacks neurovirulence.

Such modification may take the form of at least one addition, deletion, substitution or insertion of one or more nucleotides.

In one arrangement the genome is modified in each said region by a deletion of one or more nucleotides. The deletion may be of at least 50 or at least 100 nucleotides or from 0.5 Kb to 3 Kb or from 0.7 Kb to 2.5 Kb. In one arrangement the deletion is 759 bp in length and is located between nucleotide positions 125213 and 125972 of the internal long repeat ($IR_L$) and in the counterpart region of the terminal long repeat ($TR_L$) of HSV-1 strain 17.

Suitable modifications may also include the insertion of an exogenous nucleic acid sequence or exogenous/heterologous cassette comprising said sequence into the herpes simplex virus genomic DNA. The insertion may be performed by homologous recombination, or by site-specific recombination using an HSV genome with appropriate recombination sites, of the exogenous nucleic acid sequence into the genome of the selected herpes simplex virus. For example, the modification may take the form of insertion of a sequence of nucleotides encoding a gene product, such as NTR, which may be operably linked to one or more control sequences enabling expression of the gene product from the HSV vector.

Where a plurality of nucleotides are inserted, e.g. in the case of insertion of a gene sequence, the inserted nucleotides may be located entirely within, or may overlap, at least one of the ICP34.5 protein coding sequences of the HSV genome. The inserted nucleic acid may be located in both (this will usually be all) copies of the RL1 locus or ICP34.5 protein coding sequence.

The HSV may, therefore, have an inactivating mutation in the RL1 locus of the HSV genome, more specifically a mutation which inactivates the function of the ICP34.5 gene product, such that the herpes simplex virus does not produce a functional ICP34.5 gene product and is non-neurovirulent.

Accordingly, an inactivating mutation may be present in one or each ICP34.5 locus, disrupting the ICP34.5 protein coding sequence such that the ICP34.5 gene is non-functional and cannot express a functional ICP34.5 gene product.

Preferably, both copies of the ICP34.5 gene sequence contain inactivating mutations, which may be the result of one or more modifications of the HSV genome, as described above.

Where all copies of the ICP34.5 gene present in the herpes simplex virus genome (two copies are normally present) are disrupted such that the herpes simplex virus is incapable of producing a functional ICP34.5 gene product, the virus is considered to be an ICP34.5 null mutant.

The HSV may lack at least one expressible ICP34.5 gene, but is preferably an ICP34.5 null mutant.

In another arrangement the herpes simplex virus may lack only one expressible ICP34.5 gene.

The HSV may be a mutant of HSV-1 or HSV-2, more preferably of one of HSV-1 strains 17, F or HSV-2 strain HG52 and most preferably of HSV-1 strain 17. Non-neurovirulent ICP34.5 null mutants of HSV-1 strain 17 are particularly preferred and suitable examples include:

(a) HSV 1716 (ECACC accession number V92012803); and
(b) HSV 1790 (ECACC accession number 03110501).

The HSV may be a further mutant of HSV 1716 or HSV 1790.

Suitable HSV may therefore be described as mutants or variants of the parent HSV strain from which they are derived or to which they correspond. For example, HSV 1716 and HSV 1790 are mutants of HSV-1 strain 17 and may be obtained by modification of the strain 17 genomic DNA. Suitable mutant HSV may be non-wild type and may be recombinant. Mutant herpes simplex viruses may comprise a genome containing modifications relative to the wild type, as described above.

The present invention provides HSV for use in a method of medical treatment. Preferably they are provided for use in the treatment of cancer, i.e. in oncotherapy. This treatment may comprise the oncolytic treatment of the cancer, which may take the form of a tumour. Accordingly, the method of treatment may involve the killing of tumour cells by the HSV. Treatment may involve the selective infection and/or lysis of dividing cells. The use of HSV in the manufacture of a medicament, pharmaceutical composition or vaccine for the treatment of cancer is also provided. Such medicaments, pharmaceutical compositions or vaccines may comprise suitable HSV together with a pharmaceutically acceptable carrier, adjuvant or diluent.

Medicaments and pharmaceutical compositions according to aspects of the present invention may be formulated for administration by a number of routes, including but not limited to, systemic, parenteral, intravenous, intra-arterial, intramuscular, intraperitoneal, oral and nasal. The medicaments and compositions may be formulated in fluid or solid form. Fluid formulations may be formulated for administration by injection to a selected region of the human or animal body.

The HSV may be administered systemically, topically, parenterally, intravenously, intra-arterially, intramuscularly, intrathecally, intraocularly, subcutaneously, orally or transdermally. Any one of these routes of administration may involve injection of the HSV. Injectable formulations may comprise the HSV in a sterile and/or isotonic medium.

The route of administration may be selected by the ability of that route to expose substantially the entire body to the HSV. This may be determined by the ability of the HSV to circulate throughout substantially all parts of the body via the selected route. Circulation throughout substantially all of the body may exclude exposure of the HSV to one or a small number of tissues. For example, where the HSV is circulated in the blood it may be excluded from the brain by the blood brain barrier.

In preferred embodiments of the invention the HSV is administered by injection to the circulating blood, e.g. by intravenous or intra-arterial injection.

The delivery of suitable HSV to cancerous cells that are to be treated may be performed using naked virus or by encapsulation of the virus in a carrier, e.g. in nanoparticles, liposomes or other vesicles.

Administration is preferably in a "therapeutically effective amount", this being sufficient to show benefit to the individual. The actual amount administered, and rate and time-course of administration, will depend on the nature and severity of the tumour being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The HSV may be administered at any therapeutically effective dosage amount. Therapeutically effective dosages may comprise less than or equal to one of $10^3$, $10^4$, $10^5$, $10^6$, $10^7$, $10^8$ or $10^9$ plaque forming units (pfu).

The patient to be treated may be any animal or human. The patient may be a non-human mammal, but is more preferably a human patient. The patient may be male or female.

In this specification a cancerous condition may be any unwanted cell proliferation (or any disease manifesting itself by unwanted cell proliferation), neoplasm or tumour. The cancerous condition may be a cancer and may be a benign or malignant cancer and may be primary or secondary (metastatic). A neoplasm or tumour may be any abnormal growth or proliferation of cells and may be located in any tissue. Examples of tissues include the colon, pancreas, lung, breast, uterus, stomach, kidney, testis, central nervous system (including the brain), peripheral nervous system, skin, blood or lymph.

Tumours to be treated may be nervous system tumours originating in the central or peripheral nervous system, e.g. glioma, medulloblastoma, meningioma, neurofibroma, ependymoma, Schwannoma, neurofibrosarcoma, astrocytoma and oligodendroglioma, or may be non-nervous system tumours originating in non-nervous system tissue e.g. melanoma, mesothelioma, lymphoma, hepatoma, epidermoid carcinoma, prostate carcinoma, breast cancer cells, lung cancer cells or colon cancer cells. HSV mutants of the present invention may be used to treat metastatic tumours occurring in the central or peripheral nervous system which originated in a non-nervous system tissue or metastatic tumours occurring outside the central or peripheral nervous system which originated in a central or peripheral nervous system tissue.

In this specification, non-neurovirulence is defined by the ability to introduce a high titre of virus (approx $10^6$ plaque forming units (pfu)) to an animal or patient[12, 13] without causing a lethal encephalitis such that the $LD_{50}$ in animals, e.g. mice, or human patients is in the approximate range of $\geq 10^6$ pfu[11].

In this specification the term "operably linked" may include the situation where a selected nucleotide sequence and regulatory or control nucleotide sequence are covalently linked in such a way as to place the expression of a nucleotide coding sequence under the influence or control of the regulatory sequence. Thus a regulatory sequence is operably linked to a selected nucleotide sequence if the regulatory sequence is capable of effecting transcription of a nucleotide coding sequence which forms part or all of the selected nucleotide sequence. Where appropriate, the resulting transcript may then be translated into a desired protein or polypeptide.

NTR Prodrug

In this specification, "NTR prodrug" means any chemical compound or agent which is not toxic, or exhibits low toxicity, to a selected human or animal body, or to selected cells or tissues of the human or animal body, and which may be activated by a nitroreducase enzyme to a chemical compound or agent which is cytotoxic to the human or animal body or to those selected cells.

"Activation" may involve conversion of a non-toxic (or low toxicity) prodrug to an active cytotoxic form. That conversion may involve enzymatic reduction of the prodrug by NTR. The enzymatic reduction reaction may involve the prodrug as a substrate for NTR and may involve other co-factors.

Examples of NTR prodrugs may include compounds from the following classes of molecules:

1. dinitirobenzamides;
2. dinitroaziridinylbenzamides (e.g. CB1954);
3. dinitrobenzamide mustard derivatives (e.g. SN23862);
4. 4-nitrobenzylcarbamates;
5. nitroindolines;
6. nitroaromatics that are substrates of NTR and are activated to release a cytotoxic phosphoramide mustard or like-reactive species upon NTR-reduction (also called nitroaryl phosphoramides);
7. nitroaromatic prodrugs of the dinitrobenzamide class.

Examples of NTR prodrugs are disclosed in

Johansson E, Parkinson G N, Denny, W A and Neidle S. Studies on the Nitroreductase Prodrug-Activating System. Crystal Structures of Complexes with the Inhibitor Dicoumarol and Dinitrobenzamide prodrugs and of the Enzyme Active Form. J. Med. Chem. 2003, 46, 4009-4020; and Hu L, Yu C, Jiang Y et al. Nitroaryl Phosphoramides as Novel Prodrugs for *E. coli* Nitroreductase Activation in Enzyme Prodrug Therapy. J. Med. Chem. 2003 46, 4818-4821. both of which are incorporated herein in their entirety by reference.

The invention includes the combination of the aspects and preferred features described except where such a combination is clearly impermissible or expressly avoided.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures.

FIGS. 1 to 31 show light micrographs of tissue sections following tail vein administration of HSV 1790. The tissue sections illustrated, time after administration and other relevant information are set out below:

FIG. 1. Tumour tissue at day 1 following treatment; ×5 magnification. Areas of positive staining are highlighted by arrows.

FIG. 2. Tumour tissue at day 1 following administration; x20 magnification showing view of the stained area marked A in FIG. 1.

FIG. 3. Tumour tissue at day 1 following administration; ×20 magnification showing view of the stained area marked B in FIG. 1. An island of positive HSV staining is surrounded by HSV negative cells. The positively stained cells show the classic appearance of HSV infected cells—they are necrotic and form large multi-nucleated cells.

FIG. 4. Tumour tissue at day 7 following administration; x5 magnification. Large and more widespread areas of HSV staining are present, as compared to day 1 (FIG. 1).

FIG. 5. Tumour tissue at day 7 following administration. The area marked C in FIG. 4 is shown at higher magnification.

FIG. 6. Tumour tissue at day 7 following administration; ×20 magnification. Cells stained positively for HSV are shown in the area marked D in FIG. 4.

FIG. 7. Tumour tissue at day 7 following administration. Highly HSV positive cells are shown in the area marked E in FIG. 4. The tissue is highly necrotic and cell debris from dead cells are present (marked A in the Figure).

FIG. 8. Tumour tissue at day 7 following administration; ×20 magnification.

FIG. 9. Gut tissue at day 1 following administration; x5 magnification. No HSV staining is present.

FIG. 10. Gut tissue at day 1 following administration; x20 magnification. Goblet cells producing gut mucosa are visible (A) and appear to be filled with mucosa that does not stain. Area B is a fold in the tissue.

FIG. 11. Spleen tissue at day 1 following administration; ×5 magnification.

FIG. 12. Spleen tissue at day 1 following administration; ×5 magnification. A number of light brown stained circular patches are present (A). They may represent infiltrating blood.

FIG. 13. Lung tissue at day 1 following administration; ×5 magnification. The tissue appears normal and healthy with no positive staining.

FIG. 14. Lung tissue at day 1 following administration; ×20 magnification. The tissue appears normal and healthy with no positive staining.

FIG. 15. Liver tissue at day 1 following administration; ×5 magnification.

FIG. 16. Kidney tissue at day 1 following administration; ×5 magnification. No HSV staining is present.

FIG. 17. Heart tissue at day 1 following administration.

FIG. 18. Skin tissue at day 1 following administration; ×5 magnification.

FIG. 19. Brain tissue at day 1 following administration; ×20 magnification. No HSV staining is present.

FIG. 20. Gut tissue at day 7 following administration; ×5 magnification. No HSV staining is present.

FIG. 21. Gut tissue at day 7 following administration; ×20 magnification. The micrograph shows the villi and microvilli (A).

Figure 22:
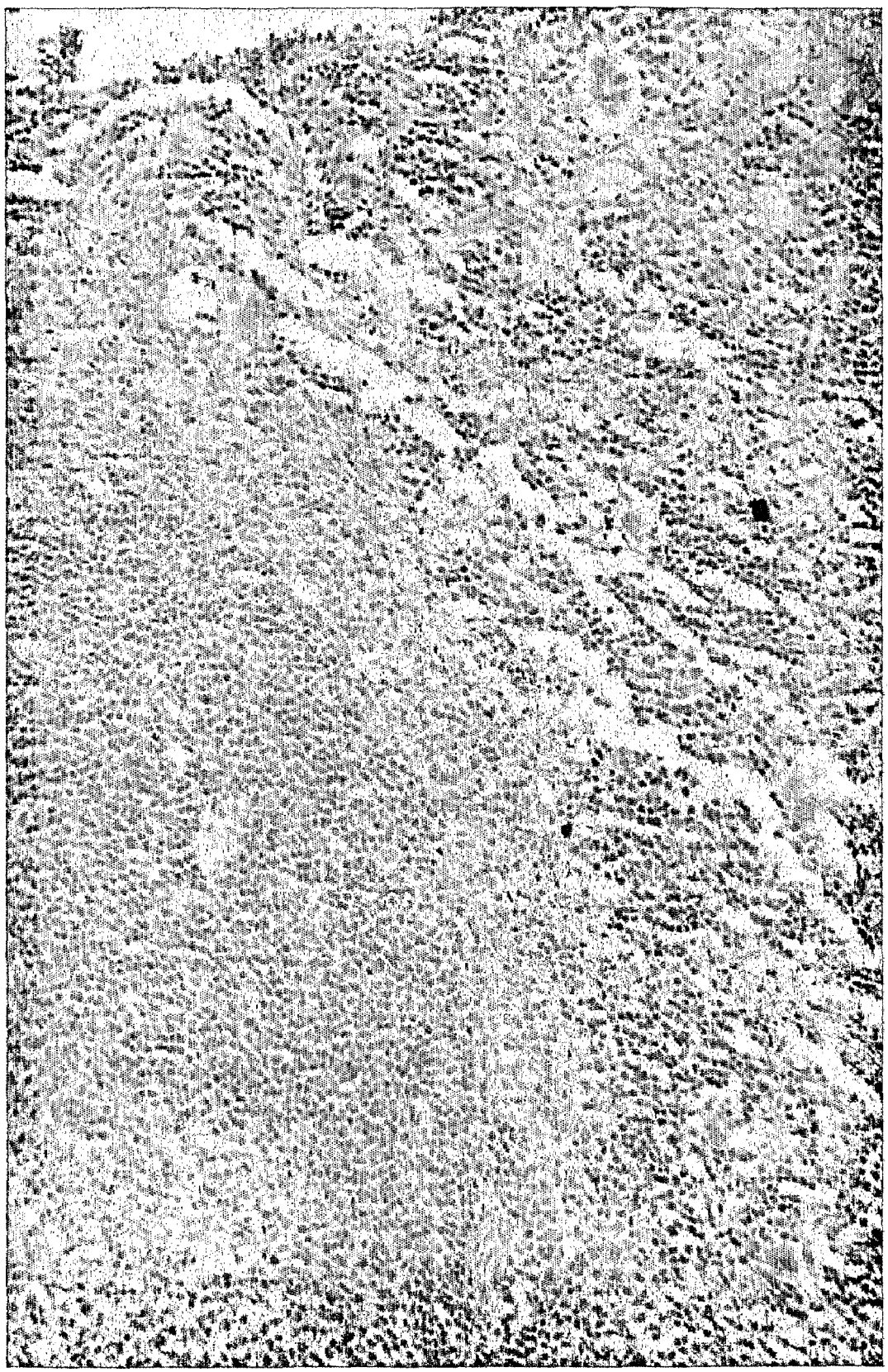

FIG. 22. Spleen tissue at day 7 following administration; x5 magnification. Most of the cells are negative for HSV staining. There is some background staining. Some cells surrounding the holes stained bright blue suggesting they are active.

Figure 23:
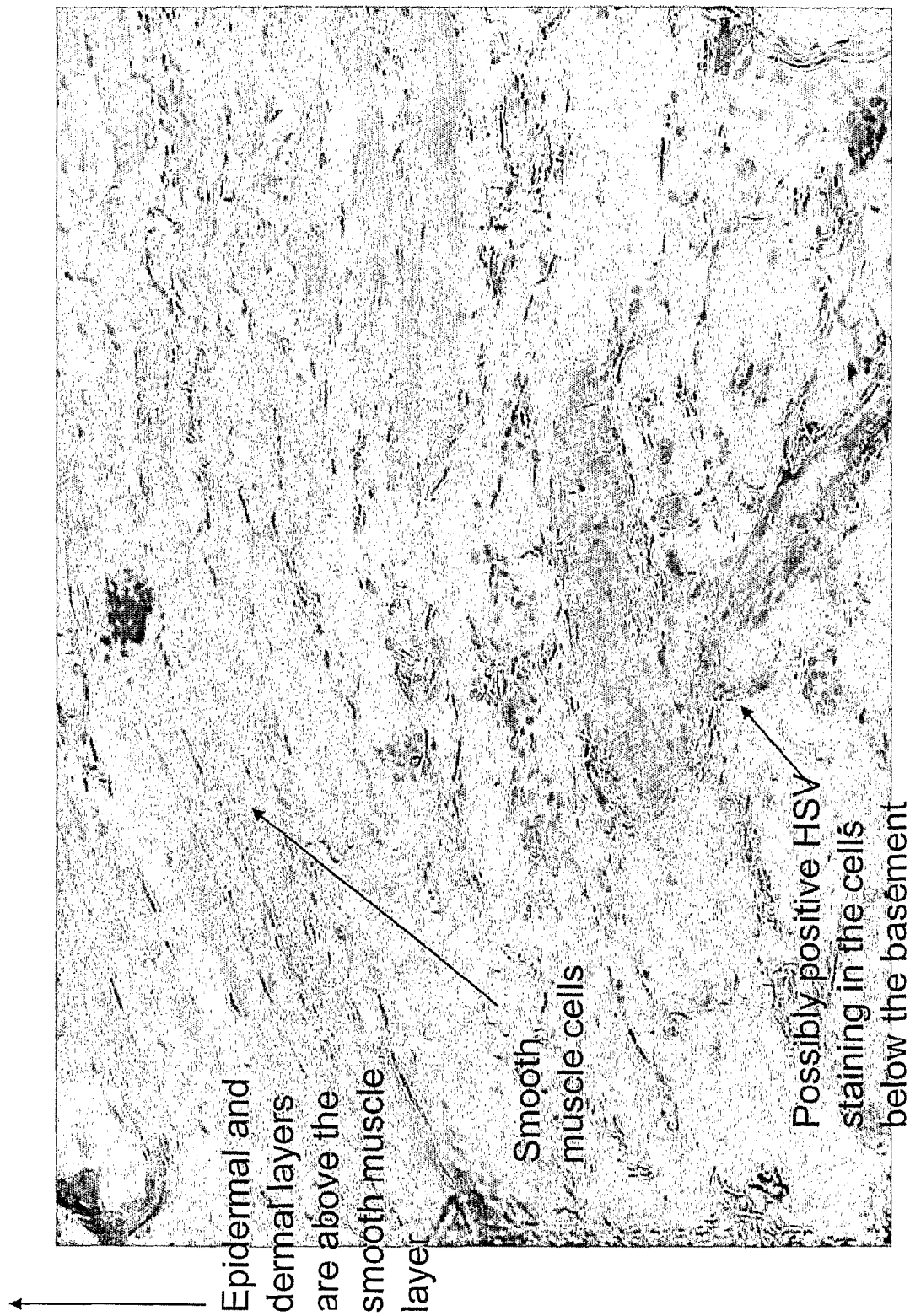

FIG. 23. Skin tissue at day 7 following administration. Some positive staining may be present in cells below the basement layer (indicated with an arrow).

Figure 24:
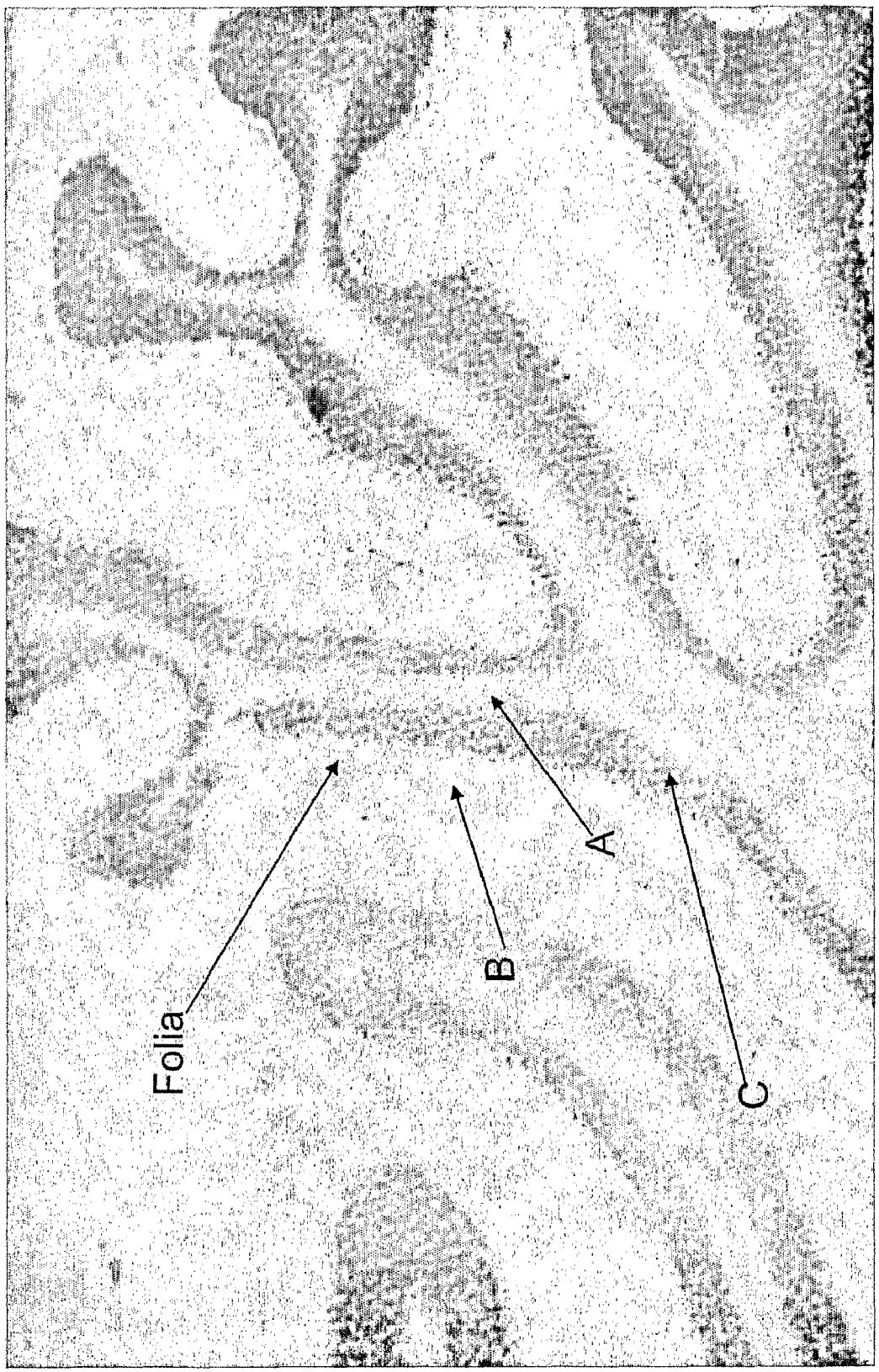

FIG. 24. Brain tissue at day 7 following administration; x5 magnification. The section is of the cerebellar cortex and shows several folia. Each folium has a central core of white matter (A), consisting of nerve processes entering and leaving the superficial cortex. The cortex has an external pale layer (B) and a darker staining granular layer beneath (C). No HSV staining is present.

Figure 25:
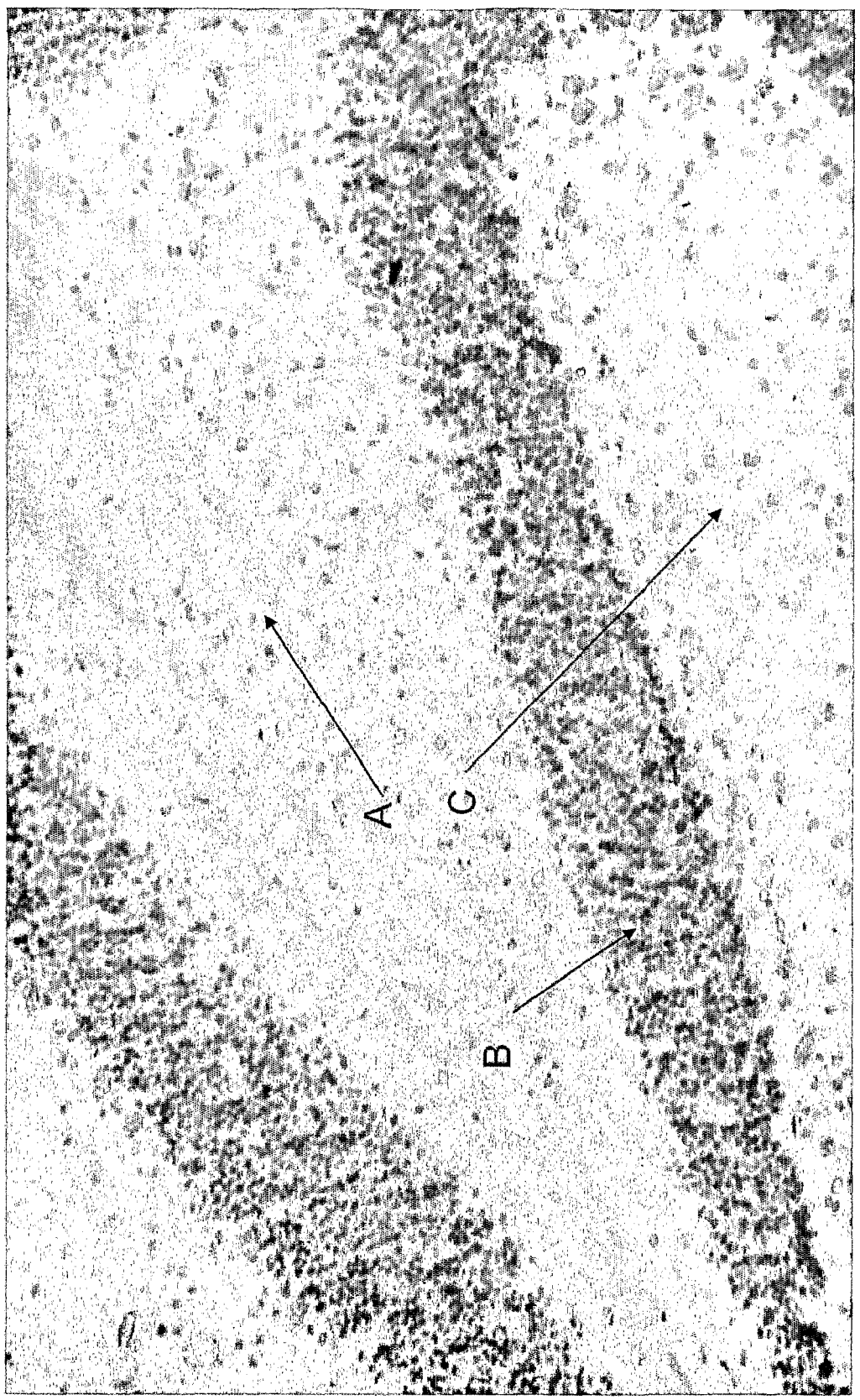

FIG. 25. Brain tissue at day 7 following administration; x20 magnification. (A) white matter; (B) granular layer; (C) cortex. No HSV staining is present.

Figure 26:
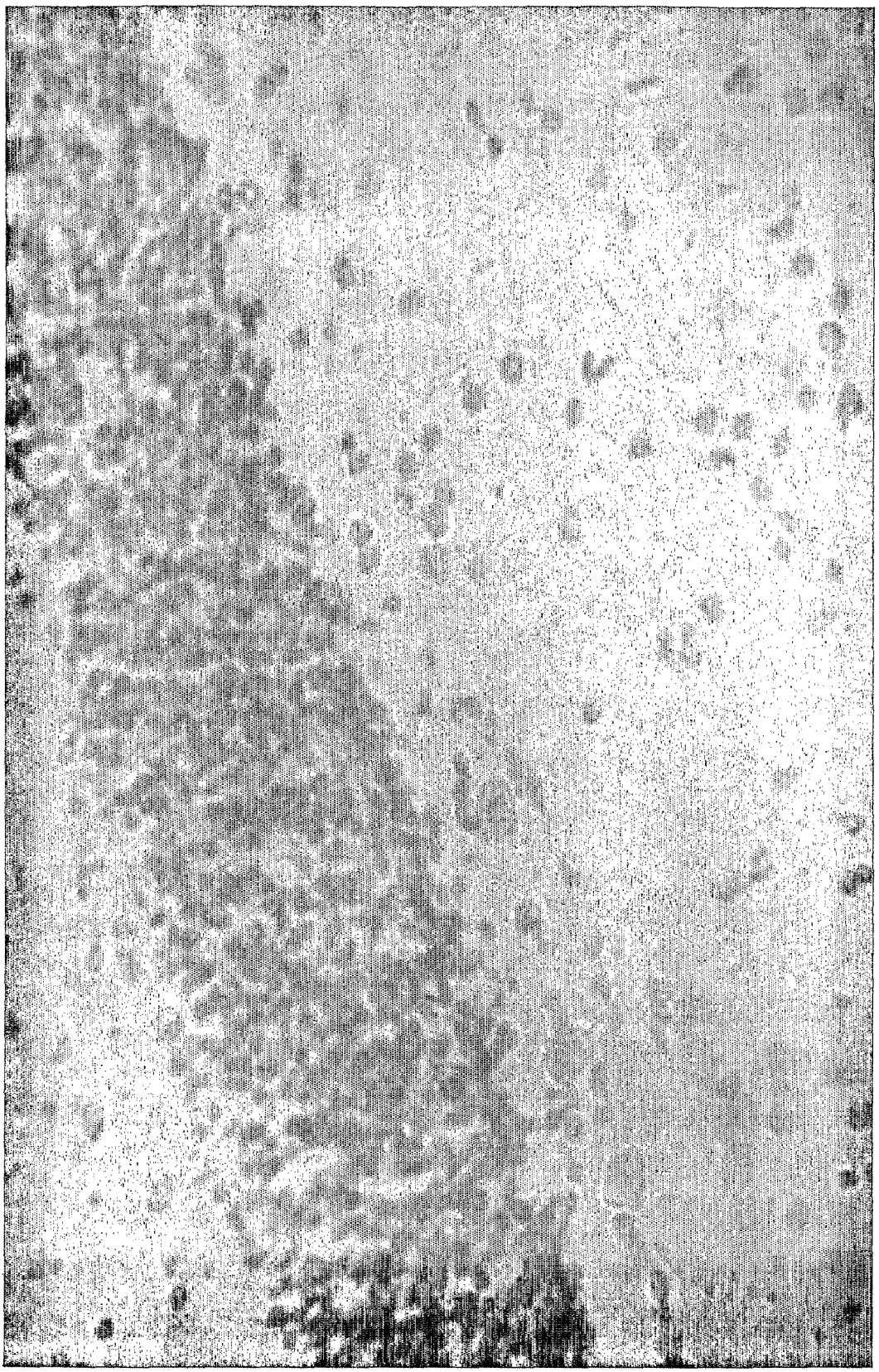

FIG. 26. Brain tissue at day 7 following administration; x20 magnification. View of the granular layer between the white matter and the cortex. No HSV staining is present.

Figure 27:
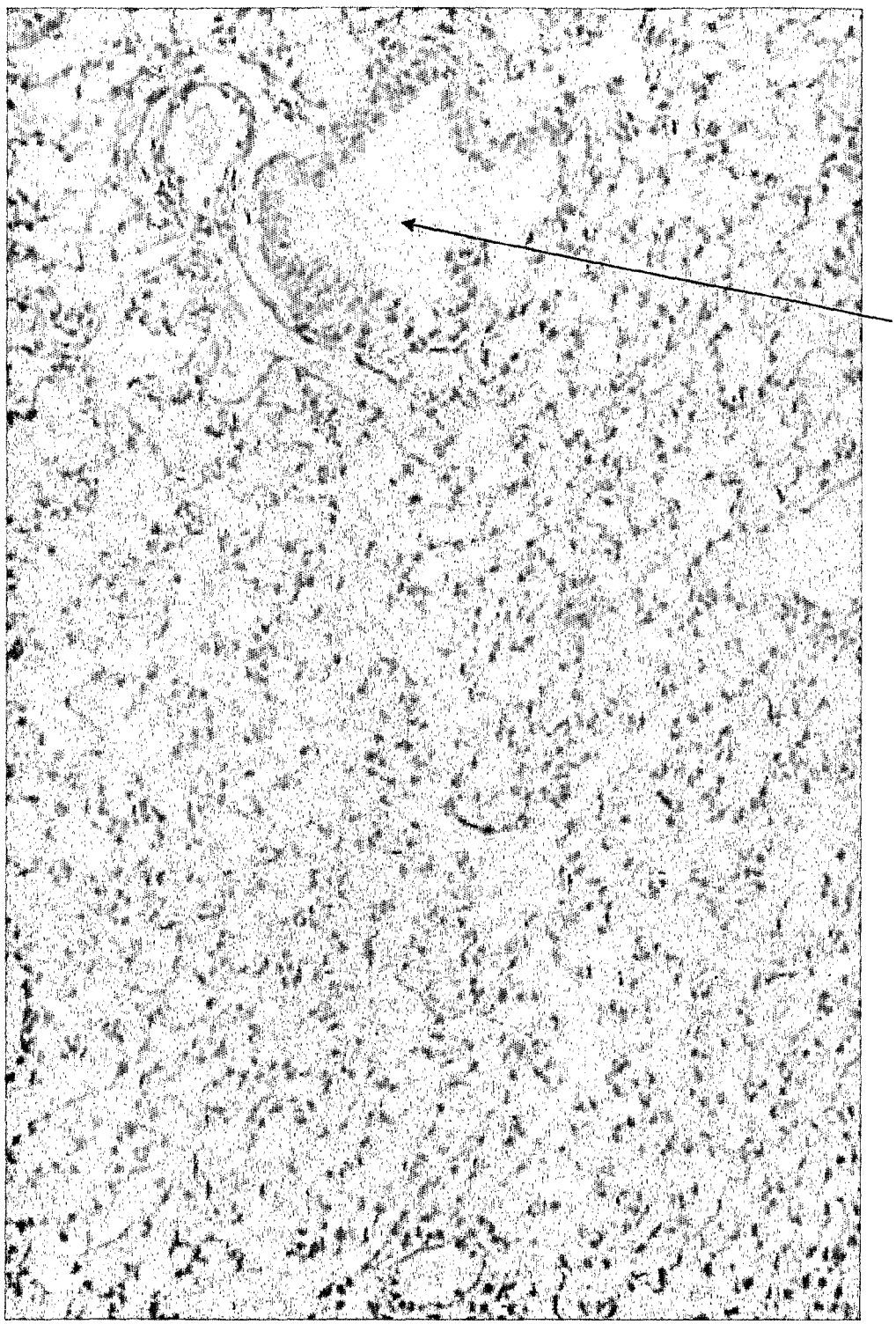

FIG. 27. Lung tissue at day 7 following administration; x5 magnification. No HSV staining is present.

Figure 28:
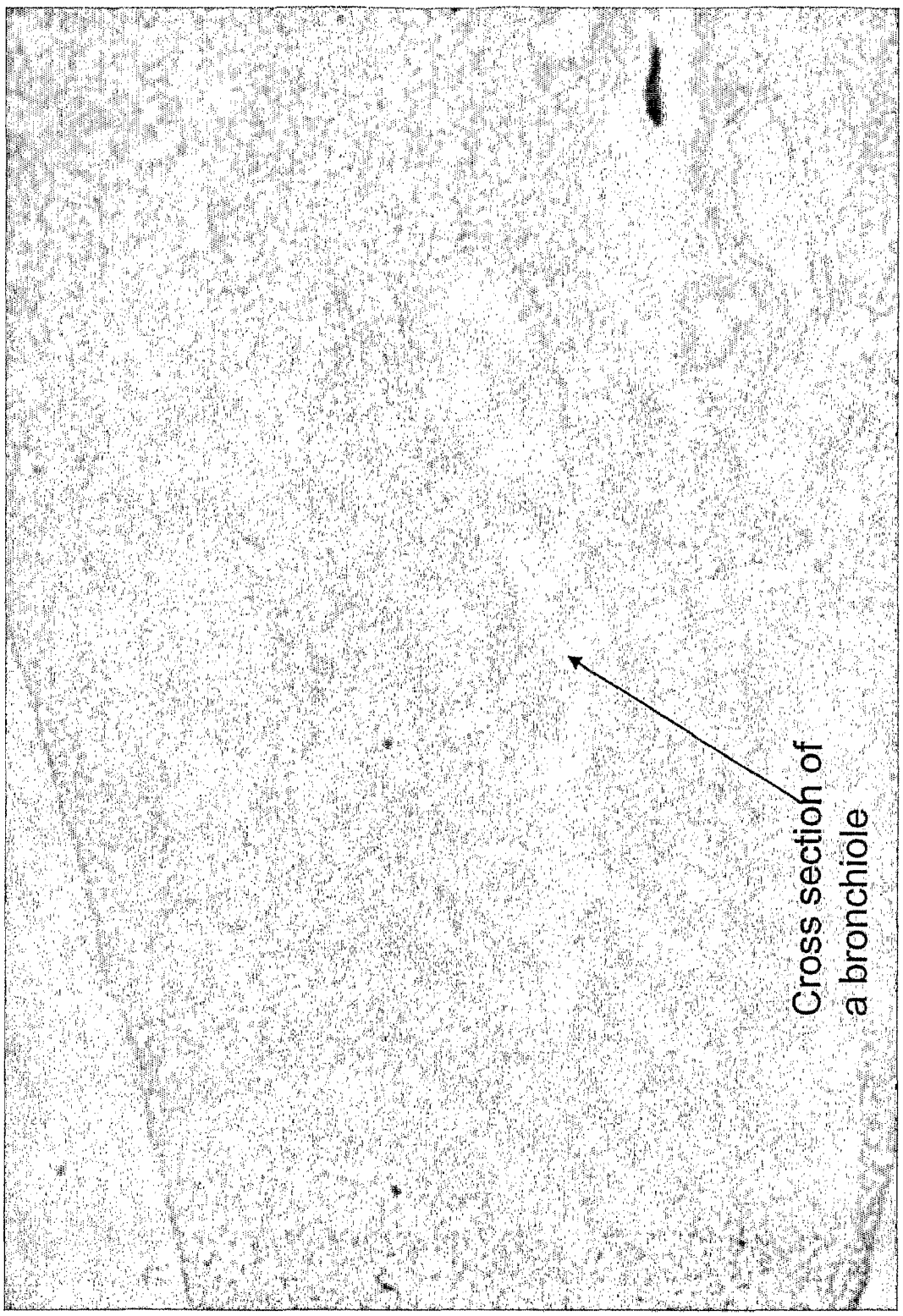

FIG. 28. Lung tissue at day 7 following administration; x5 magnification. No HSV staining is present.

Figure 29:
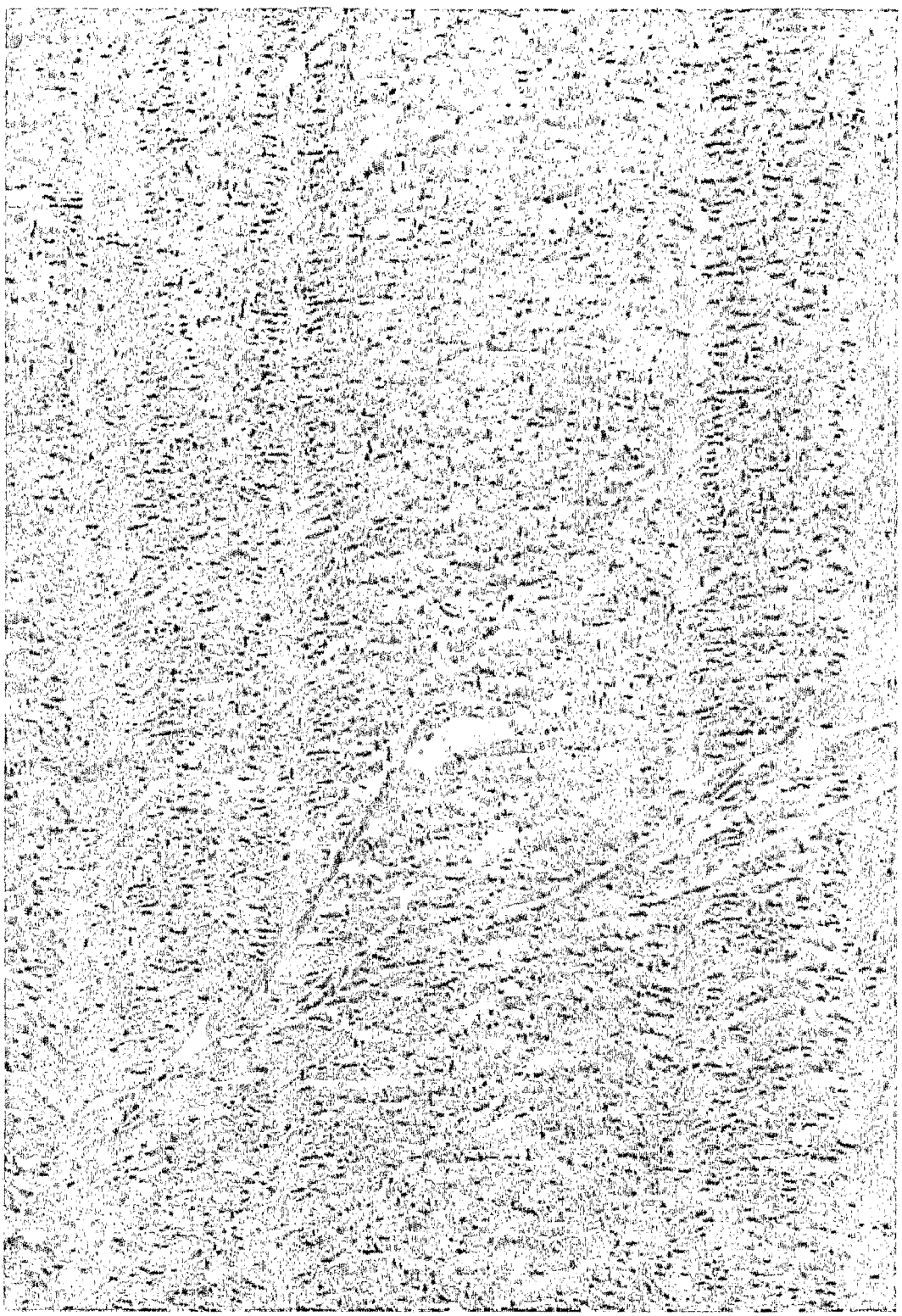

FIG. 29. Heart tissue at day 7 following administration; x5 magnification. No HSV staining is present.

Figure 30:
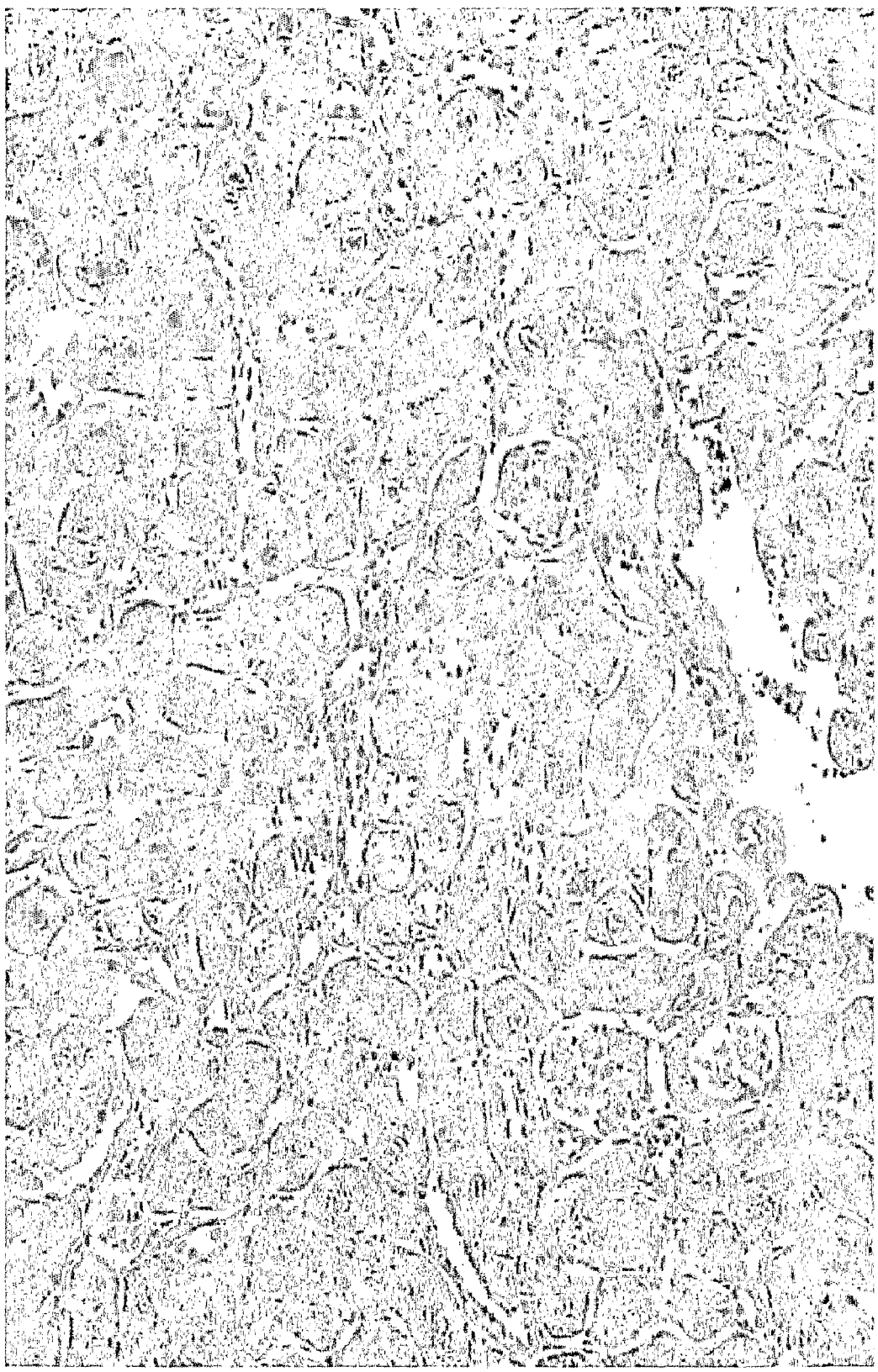

FIG. 30. Kidney tissue at day 7 following administration. Background staining in this section is present, but individual cells are not stained for HSV.

Figure 31:
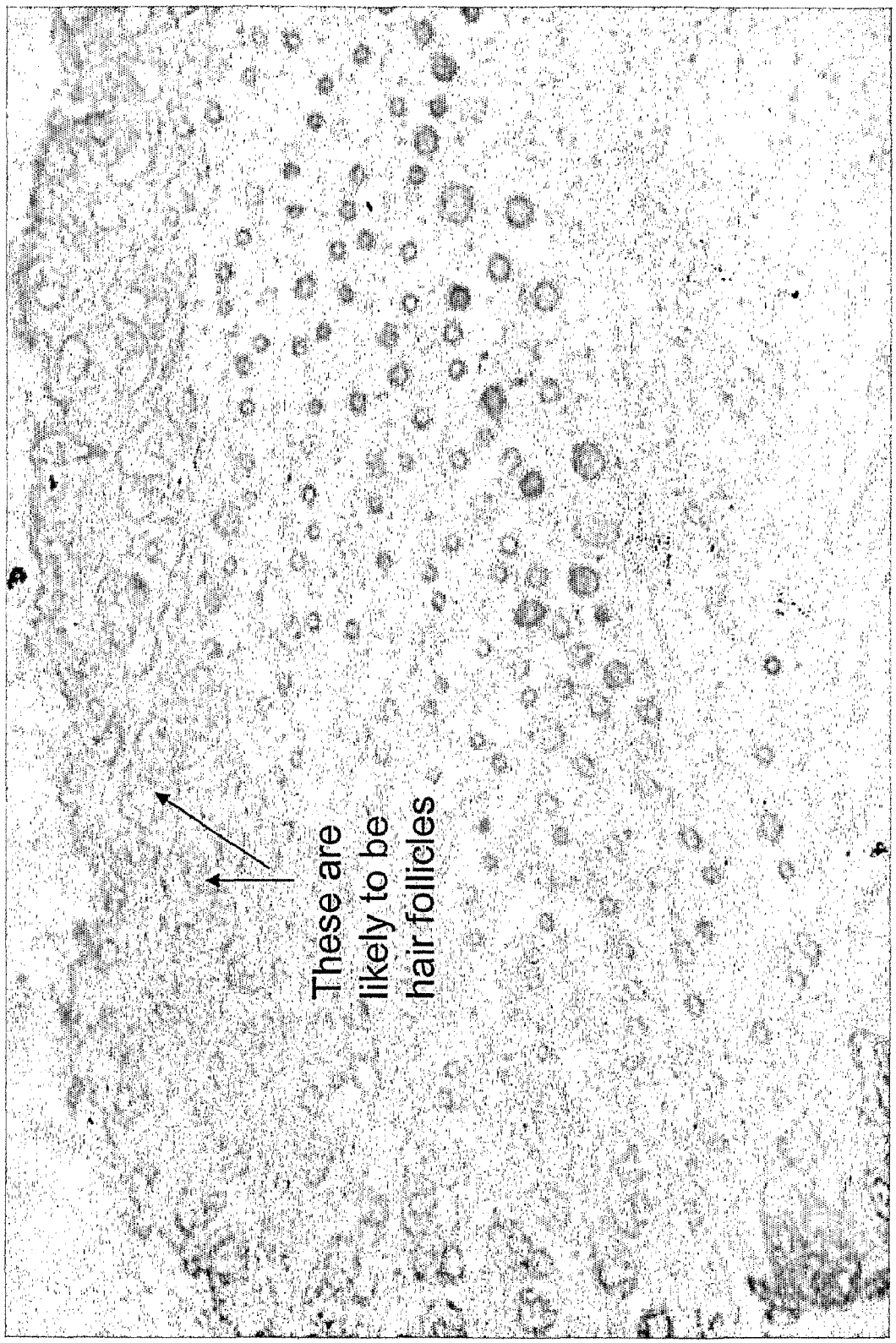

FIG. 31. Skin tissue at day 7 following administration; x5 magnification. No HSV staining is present.

Figure 32:
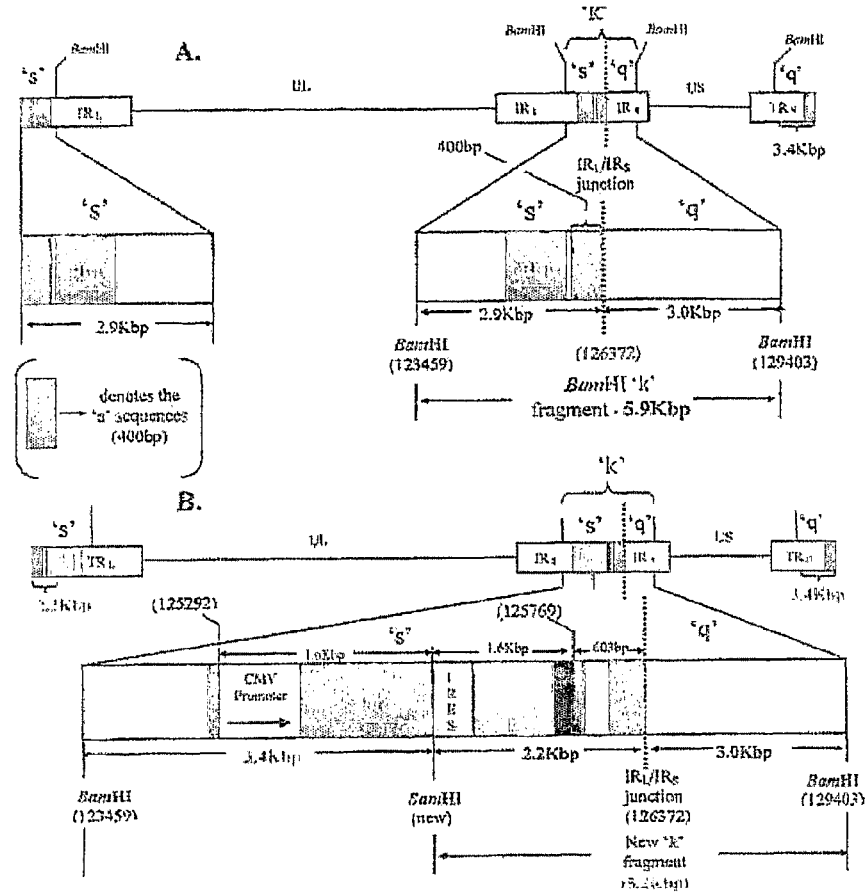

FIG. 32. Schematic representation of (A) the HSV17+ genome and (B) the HSV1716/CMV-NTR/GFP genome. BamHI cuts the HSV-1 genome in several places to generate fragments of different sizes. The RL1.del probe contains the BamHI 'k' fragment and will therefore hybridize to fragments that contain sequences in the BamHI 'k' region. If the foreign DNA had been inserted into the HSV-1 genome in the location shown in B, the normal BamHI 'k' fragment would disappear and be replaced with a smaller fragment of 5.2 Kbp. The BamHI 'q' fragment would not be altered and should be 3.4 Kbp. Two new fragments (3.4 Kbp and 2.2 Kbp) would be generated in place of the one 's' fragment that would hybridize to the RL1.del probe. The fragments are visualized by Southern Blotting.

Figure 33:
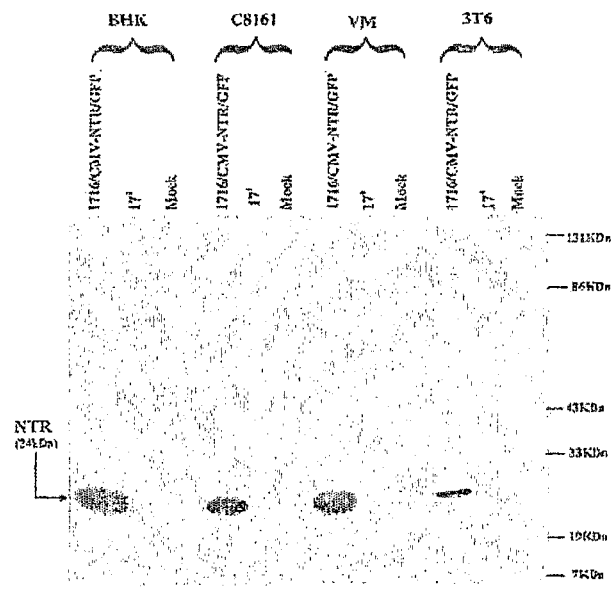

FIG. 33. Western blot analysis of NTR expression in HSV1716/CMV-NTR/GFP infected cell lines. BHK, C8161, VM and 3T6 cells were infected with 10 pfu/cell HSV1716/CMV-NTR/GFP, HSV17+ or mock infected. 16 hrs post infection, the cells were harvested and protein extracts analyzed in a Western blot using a polyclonal NTR-specific antibody. Significant NTR expression was detected in all the HSV1716/CMV-NTR/GFP infected cells. No NTR expression was detected in the mock or HSV17+ infected cells.

Figure 34:
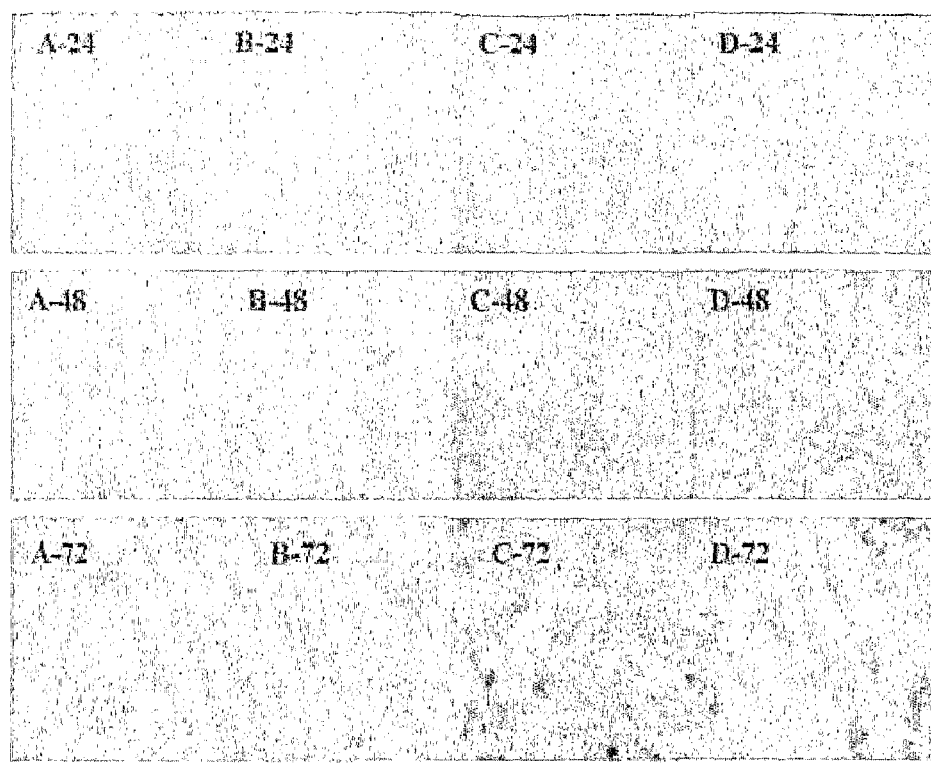

FIG. 34. Confluent 3T6 cells 24, 48 and 72 hrs post treatment with HSV1790, CB1954, or both.

Confluent 3T6 cells in 60 mm dishes were mock infected (A and B) or infected with 10 pfu/cell HSV 1790 (C and D). After 45 minutes, the cells were overlaid with media. 50 µM CB1954 was included in the overlay in B and D. After 24 hrs, no significant effects were observed in the mock infected cells overlaid with media containing 50 µM CB1954 (B). However, enhanced cell killing was evident in HSV1790 infected cells overlaid with media containing CB1954 (D) compared with HSV1790 infected cells overlaid with media not containing CB1954 (C). Images were captured under a 10x objective.

Figure 35:
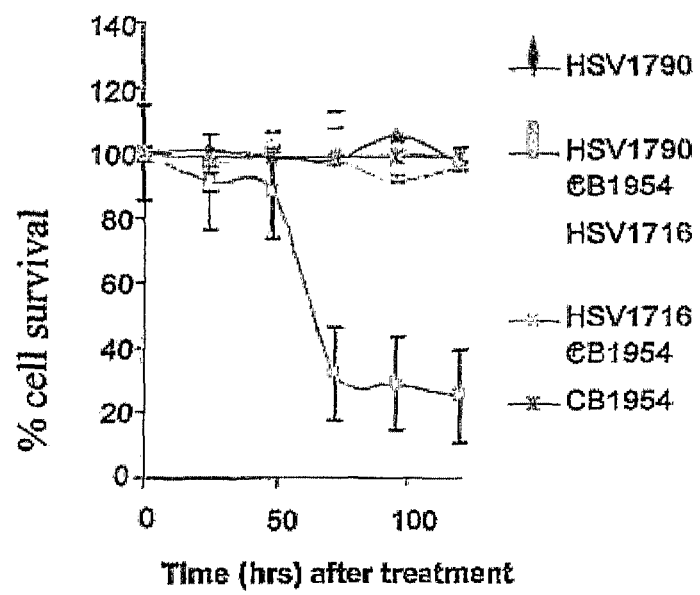

FIG. 35. Confluent 3T6 cells were infected with HSV1790, HSV1716 or no virus. After 45 minutes, the infected cells were overlaid with media containing CB1954 or with media alone. At 24, 48, 72, 96 and 120 hours, % cell survival (y axis) was determined relative to that of mock infected cells without prodrug using CellTiter 96 Aqueous Solution Cell Proliferation Assay (Promega). Figures shown represent the mean of 3 values ±SD.

Figure 36:
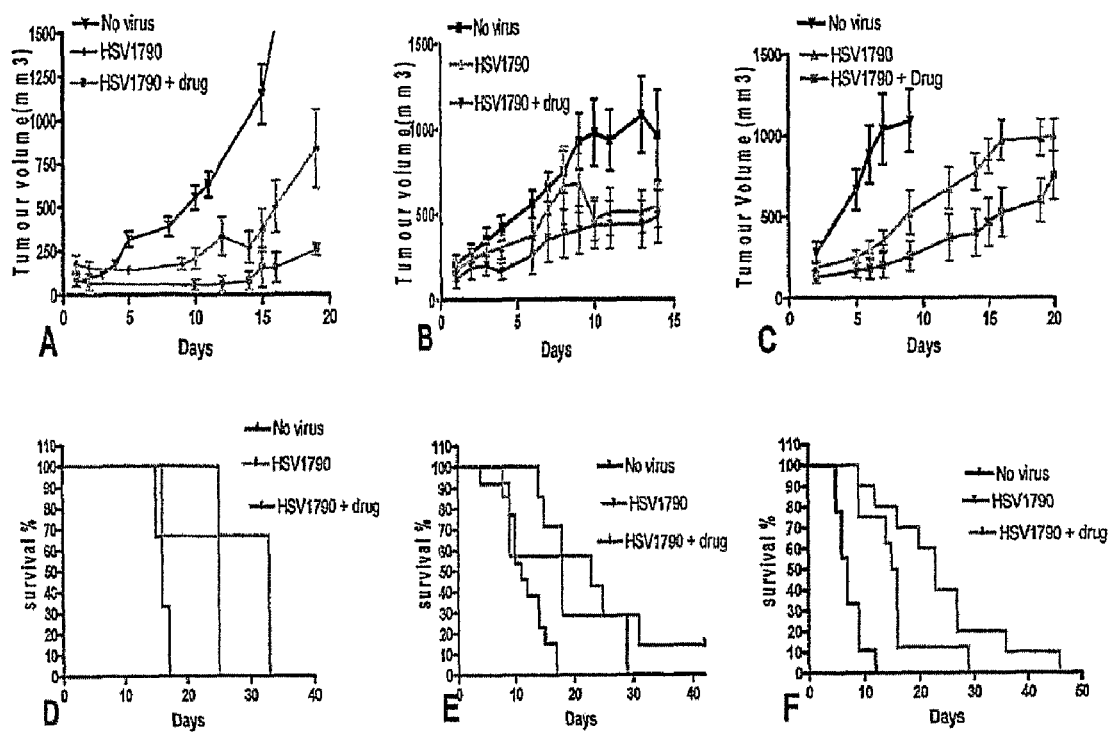

FIG. 36. Comparison of tumour volume between HSV1790 treated tumours and tumour receiving no treatment in A2780 (A) CP70 (B) and A431 (C).

(A) A2780 human tumour xenograft model. Mice treated with a combination of HSV1790 and CB1954 had smaller tumour burdens and (D) significantly longer survival that those either not virally treated or treated with HSV1790 only (p<0.05-log rank test). As n=3 in this tumour type the reduction in tumour volume seen was not significant.

(B) In CP70 xenografts the addition of the prodrug CB1954 had no effect on tumour volume, or (E) survival.

(C) Mice bearing A431 xenografts. Tumours treated with a combination of HSV1790 and CB1954 were significantly smaller than those treated with HSV1790 alone (P<0.05) the difference in survival (F) between animals treated with HSV1790 alone or HSV1790+CB1954 is not statistically significant by log rank method. However, the difference in the median survival between animals treated with HSV1790 alone and those treated with HSV1790+CB1954 is significant (P=0.034, Students t test).

Figure 37:
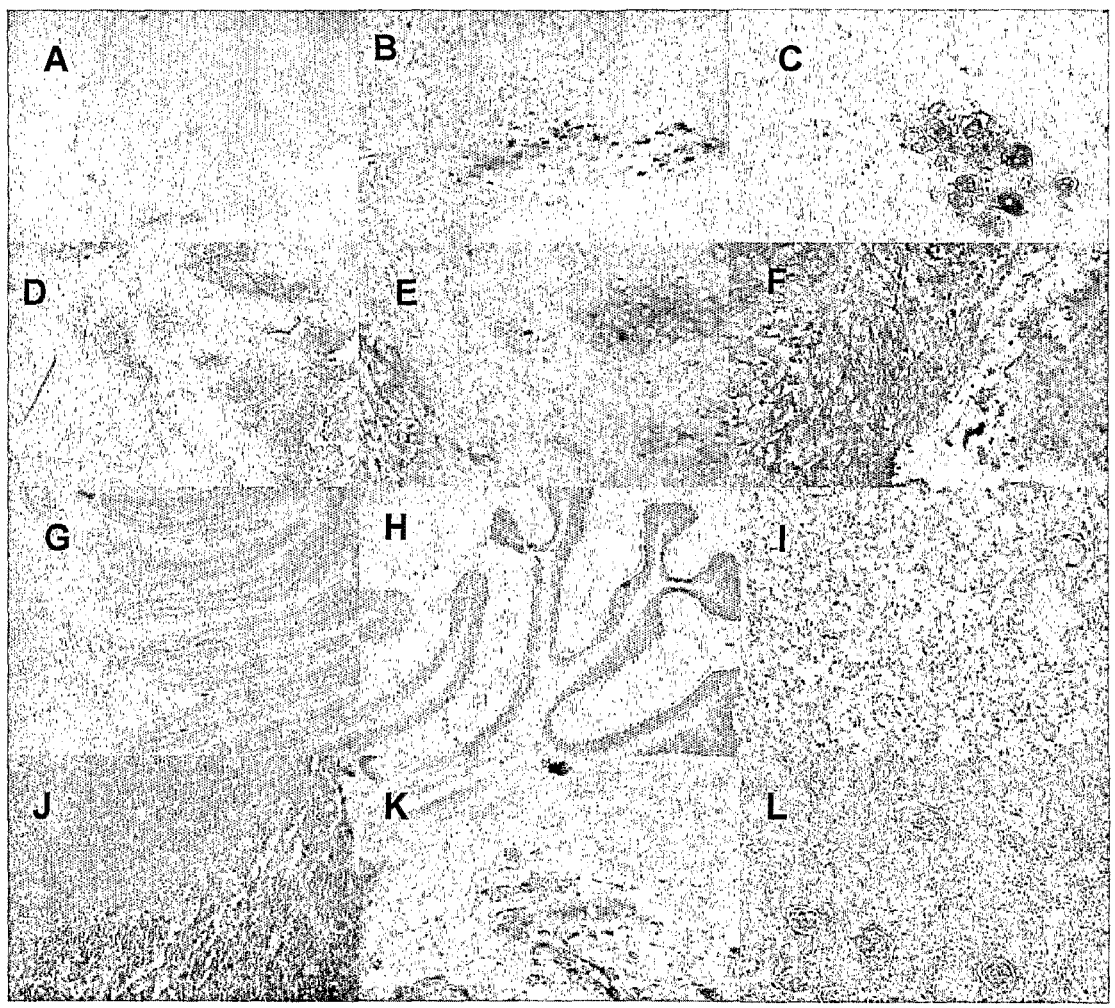

FIG. 37. Immunohistochemical staining of UVW xenograft tumours using an HSV antibody.

(A) Low power field (x5) of tumour at day 1 post i.v viral injection showing small areas of positively stained cells (brown stained cells).

(B) x20 magnification of the areas with positive staining cells.

(C) (x40) shows area with a typical HSV infection—giant multi-nucleated cells have formed holes, where cells have been killed.

(D) x5 magnification of Day 7 post i.v HSV1790 injection showing more and larger areas of positive staining.

(E, F) x20 magnification of areas from (D). (F) shows an area of HSV mediated necrosis, with cell debris visible.

(G) Cross section of the gut showing villi—an area of active cell division.

(H) Section of cerebellar cortex. The cortex has an external pale layer and a darker staining granular layer between it and the white matter.

(I) Lung section. A bronchiole is visible on the left of the section.

(J) Spleen section.

(K) Skin section x20.

(L) Liver section x20.

Figures 38, 39:
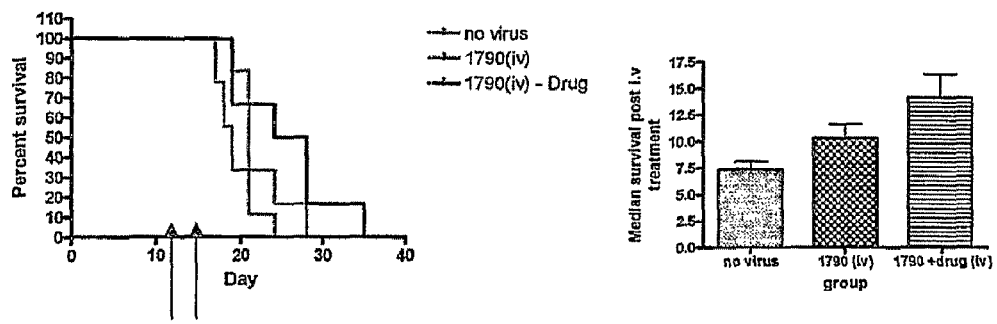

FIG. 38. PCR Results from samples of major organs and xenograft tumours following i.v injection of HSV1790. DNA PCR detects the presence of virus. RNA PCR (reverse transcriptase PCR) detects mRNA, therefore detecting actively replicating virus.

Key:

+++ very strong band

++ strong band

+ weak band

− no band (RNA only) NI—non informative, sample contaminated with DNA.

FIG. 39. Kaplan-Meier plots indicate survival of the athymic nude mice bearing subcutaneous A431 tumours.

Figure 13:
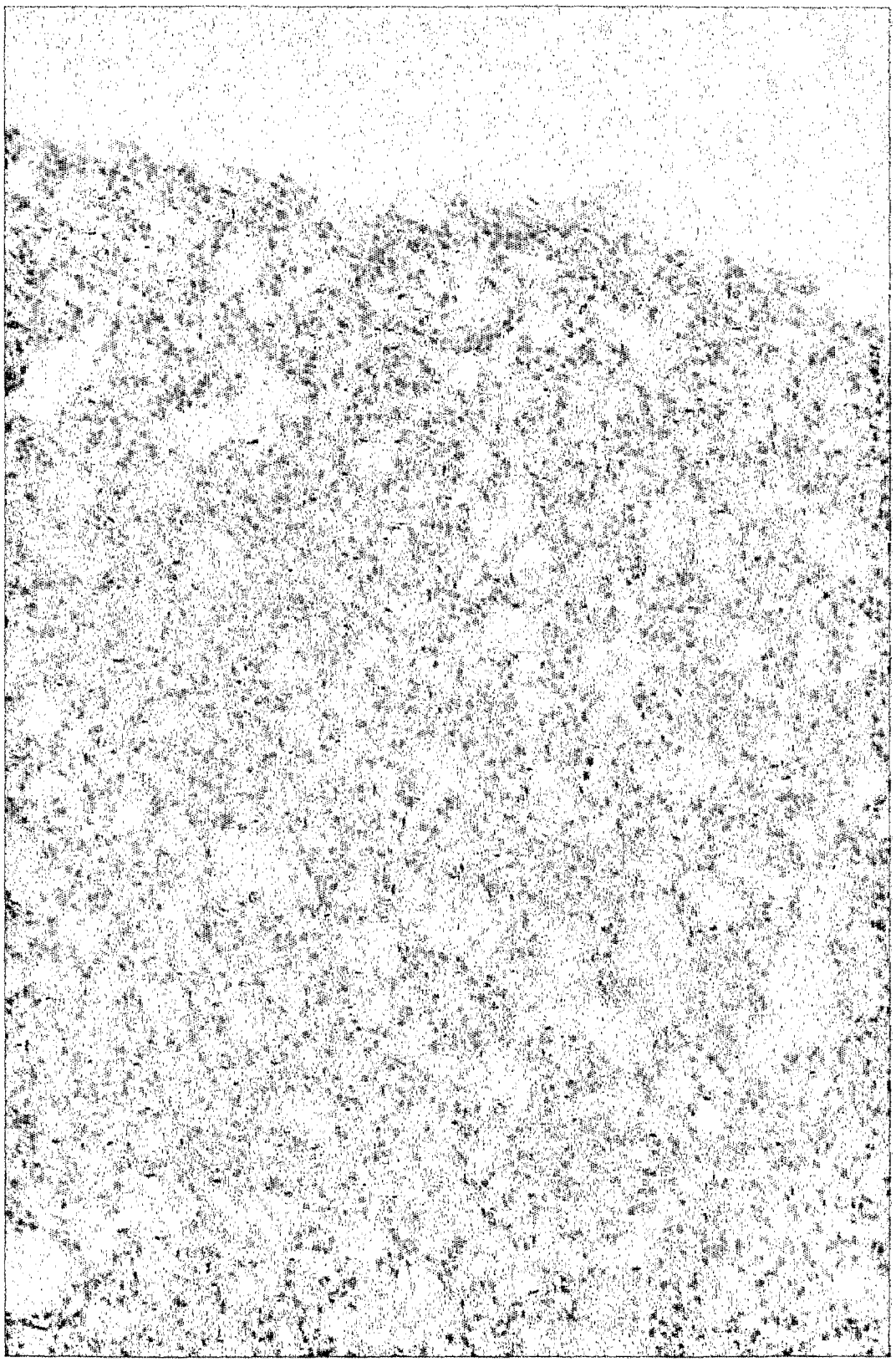
Figure 14:
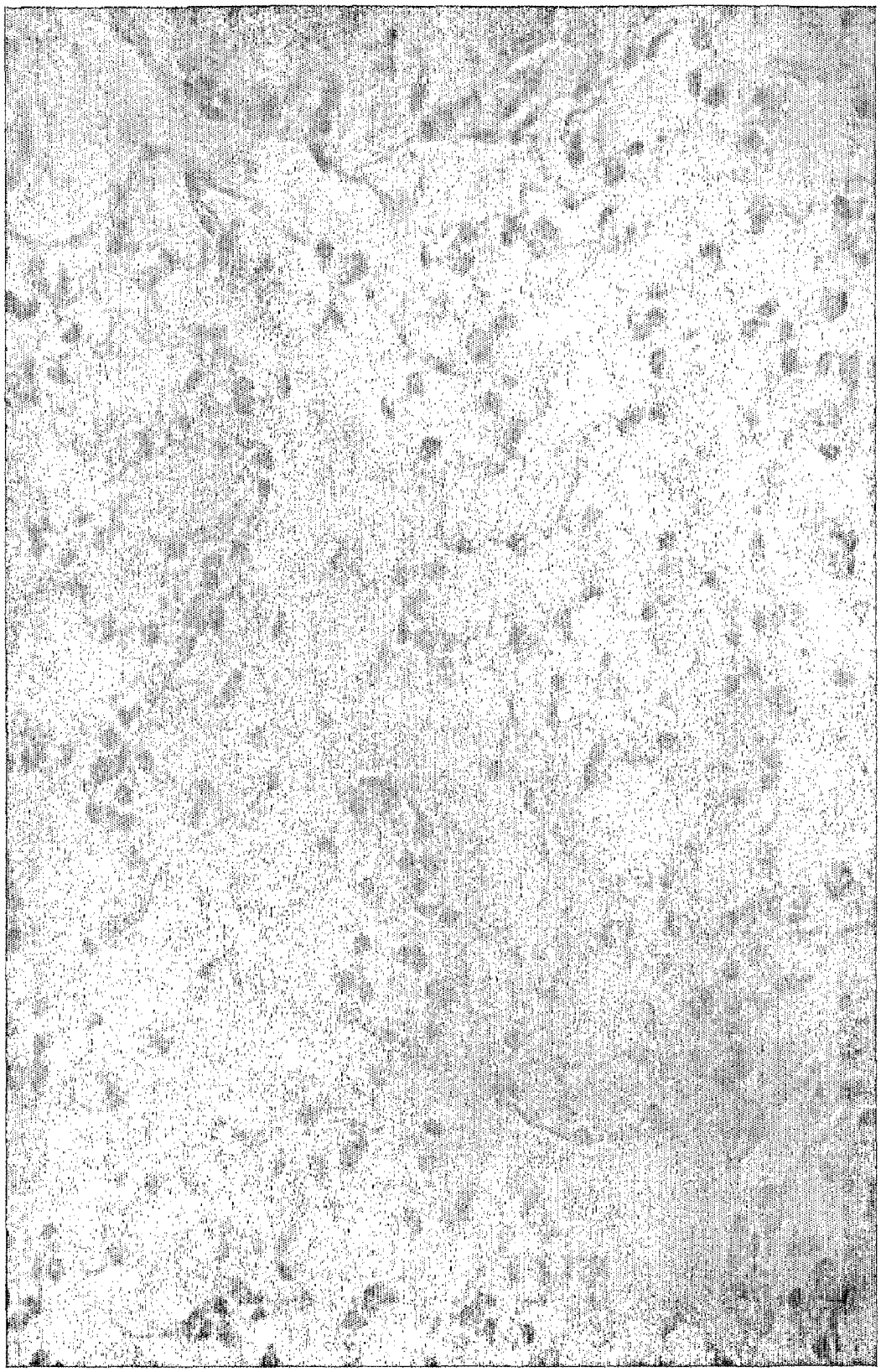
Figure 15:
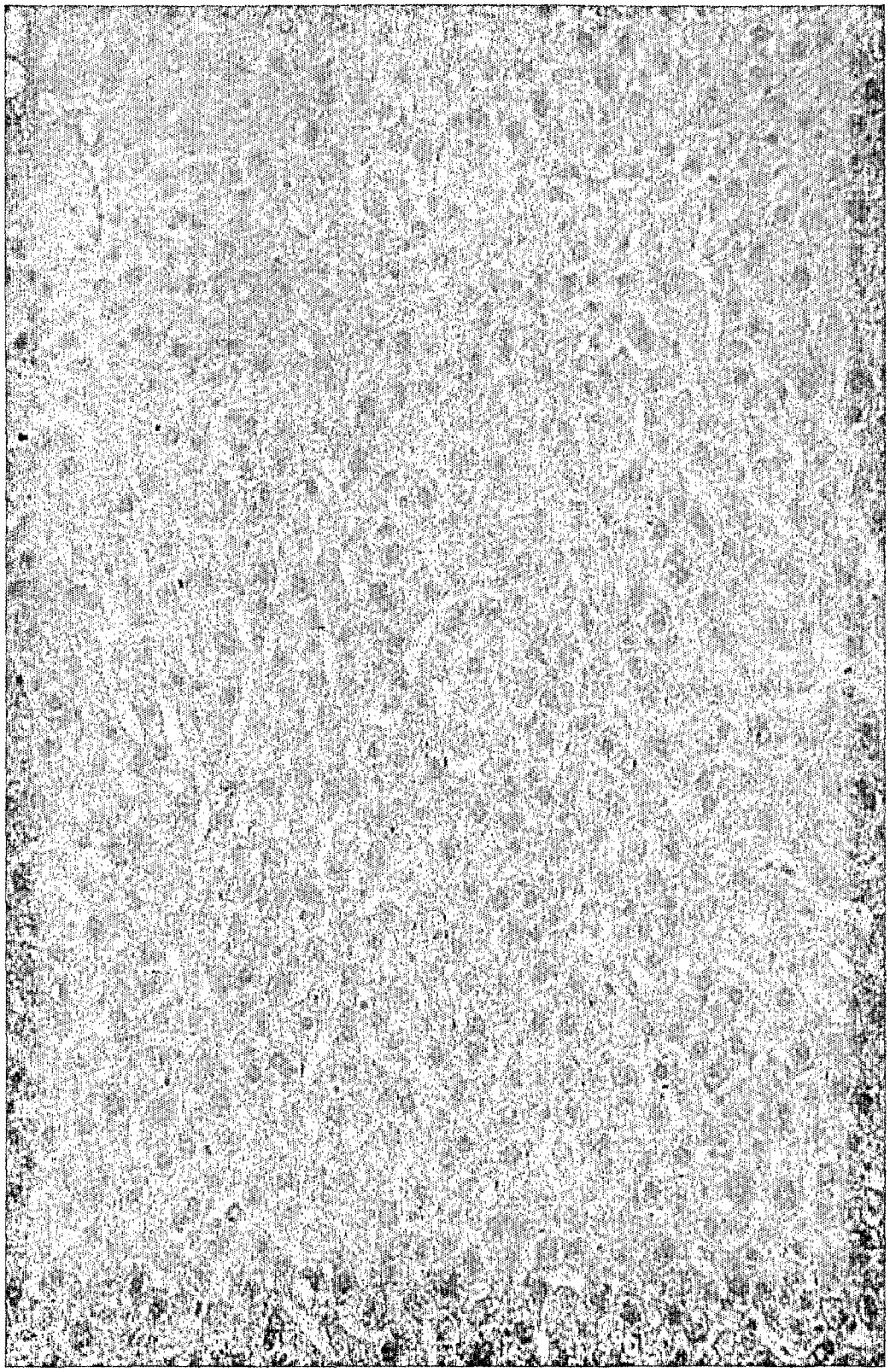
Figure 16:
Figure 17:
Figure 18:
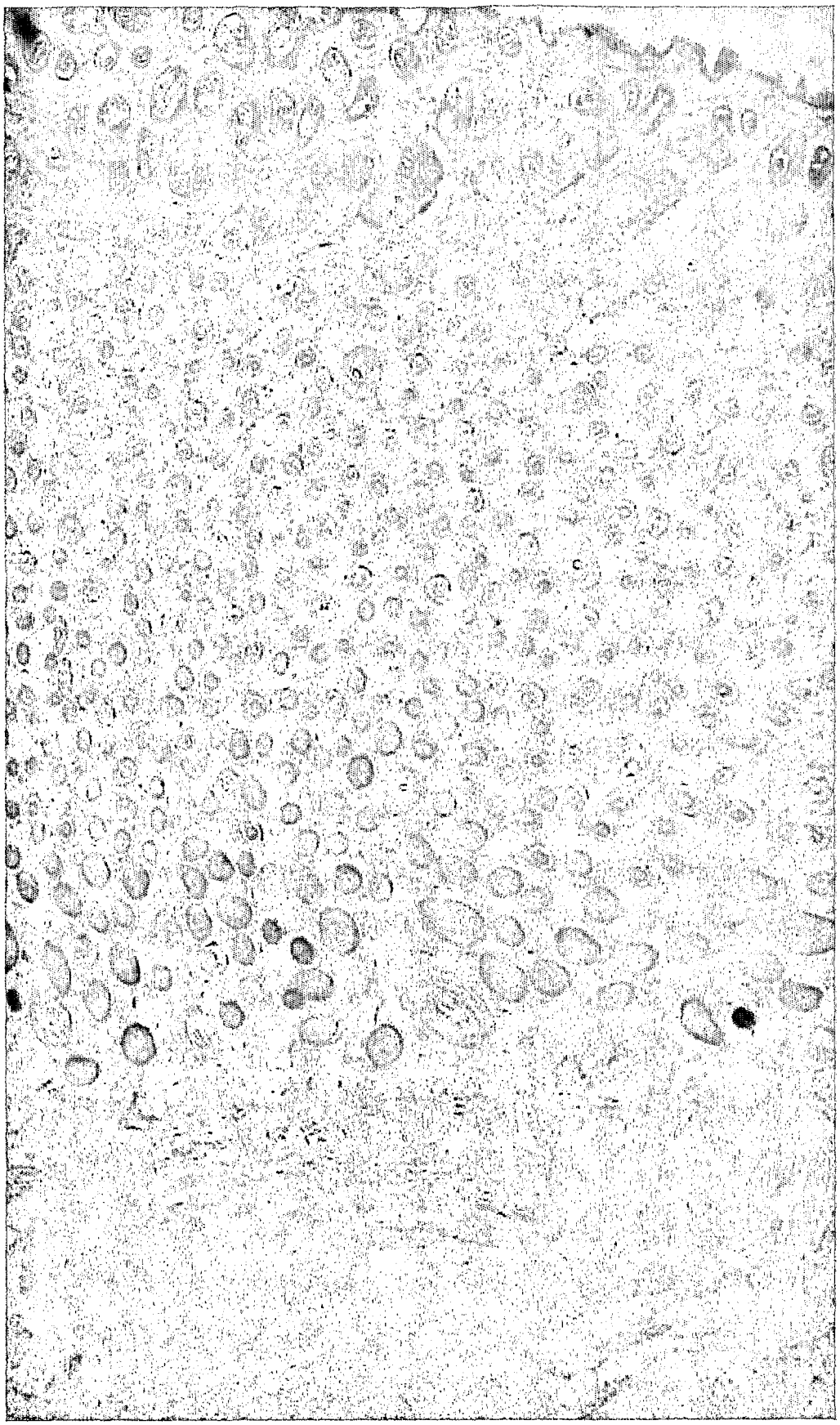
Figure 19:
Figure 20:
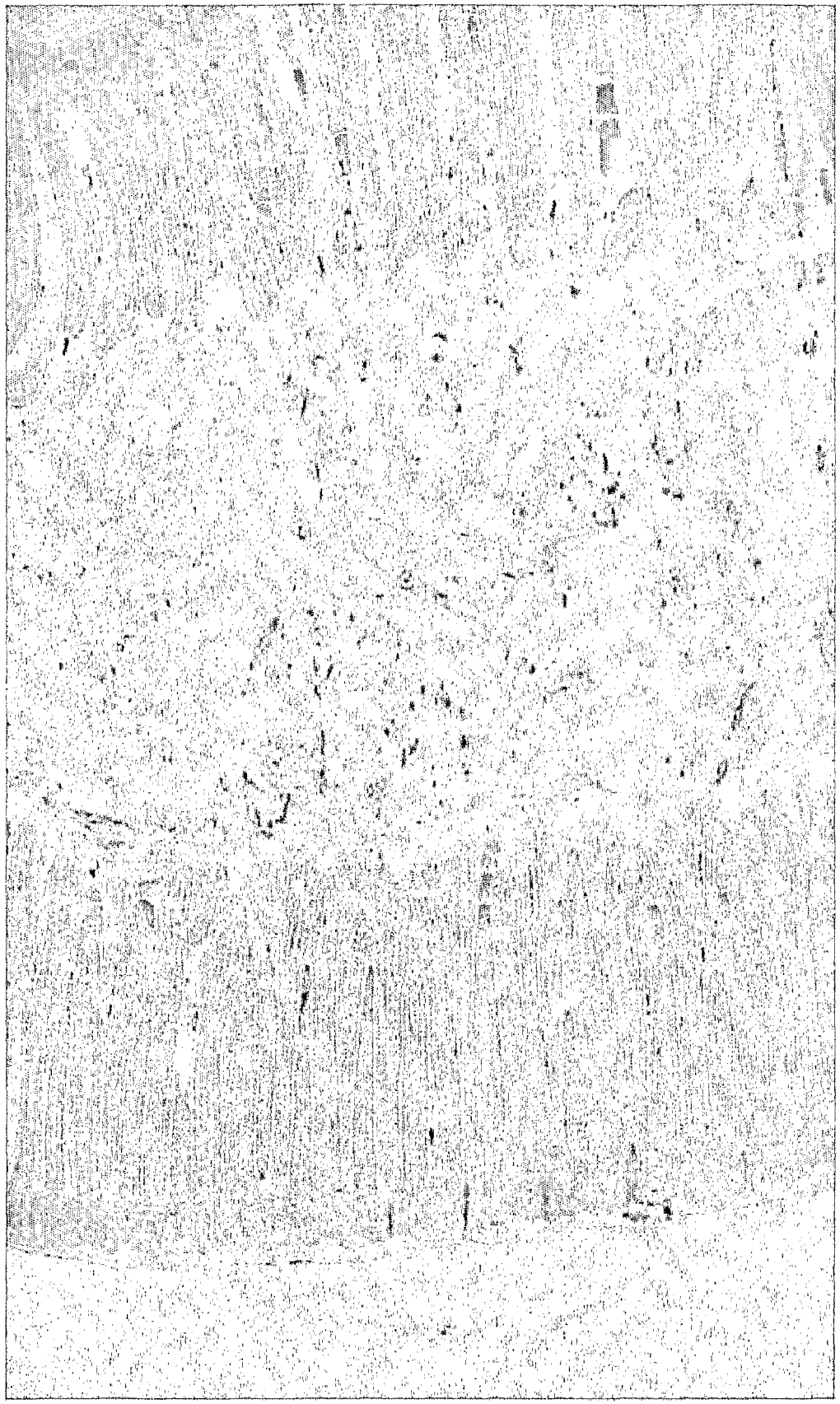
Figure 21:
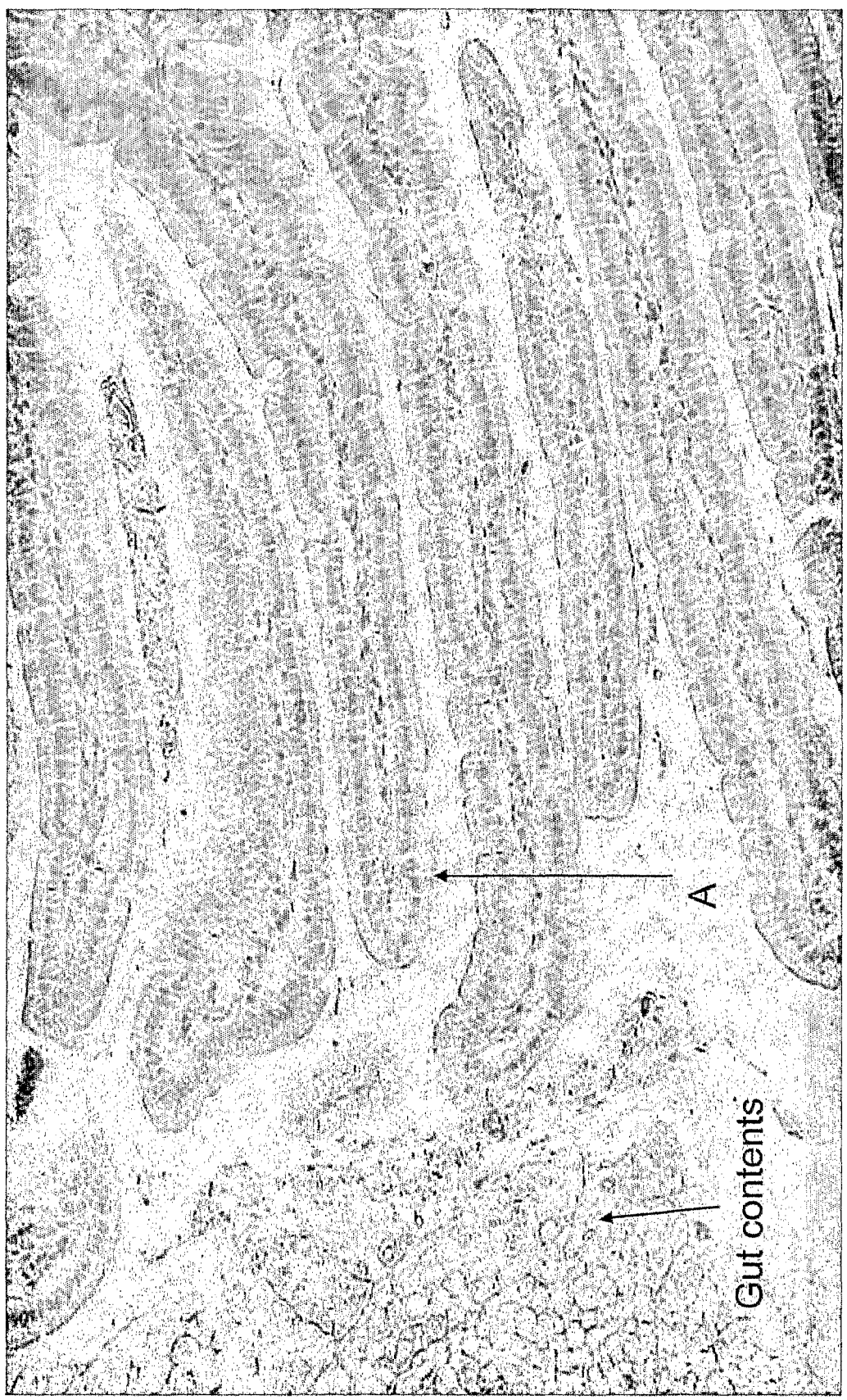

A431 cells were injected subcutaneously and twelve days later, animals received treatment (arrows) with HSV1790 ($1\times10^6$ pfu/mice) on two occasions (day 12 and 14 post cell injection) with or without 5 further injections of 20 mg/kg CB1954 at days 15, 16, 17, 18 and 19. Control animals received media only. Each line represents a group, with at least 6 mice in each group. The two arrows indicate the days on which the virus was injected, days 12 and 14. Mice were monitored daily and killed when their tumour diameter reached 15 mm. Tumours were removed at time of death and immunohistochemistry performed to look for the presence and/or replication of the virus within the tumour. The median survival (time at which half the subjects have died) for the group of mice given no treatment was 19 days; given HSV1790 by i.v, 21 days; and given HSV1790 by i.v and given CB1954 26 days. Median survival of each group is plotted on FIG. 13*b*, both virally treated groups have significantly improved survival (p=0.02 and 0.007) respectively.

DETAILED DESCRIPTION OF THE INVENTION

Specific details of the best mode contemplated by the inventors for carrying out the invention are set forth below, by way of example. It will be apparent to one skilled in the art that the present invention may be practiced without limitation to these specific details.

EXAMPLE 1

Materials and Methods

Nude mice were subcutaneously injected with ~$20\times10^6$ UVW tumour cells (a glioma cell line) at 60% confluency per mouse to generate UVW xenografts in the right flank. The mice were inspected regularly for xenograft formation.

Once the xenografts had reached approximately 5 mm×5 mm the mice were injected intravenously with $10^7$ PFU HSV 1790 via tail vein injection.

In these experiments HSV 1790 was used as an exemplary HSV-1 strain 17 ICP34.5 null mutant. No prodrug activatable by NTR was administered.

One mouse was sacrificed at day 1 post injection and one at day 7 and the organs harvested. The following tissues were collected: tumour, blood, liver, lung, spleen, heart, kidney, gut, brain and skin.

Half of each sample was flash frozen in LN2 and processed for polymerase chain reaction (PCR) analysis, the other half was fixed in neutral buffered formalin for use in immunohistochemistry.

Immunohistochemistry

Sections were stained with an HSV polyclonal antibody (Dako HSV type 1 polyclonal {Cat. No. B0144} and secondary antibody Vectastain Elite rabbit IgG kit {Cat. No. PK6101}) and counterstained with haematoxylin. The sections were observed by light microscopy.

Positive staining was indicated by a dark brown colour and negative staining by a blue colour. Background staining was present in some samples and showed variation between tissue types, for example muscle and cardiac cells exhibited a light brown background stain. The background staining observed was separate and entirely distinguishable from the dark brown colour indicative of positive HSV staining.

The results of the immunohistochemical analysis are shown in FIGS. 1-31.

PCR

DNA and RNA was isolated from the flash frozen samples. The RNA was used to make cDNA using the ImProm Reverse Transcriptase kit (Promega). The cDNA obtained was then used for PCR. The following PCRs were performed:

HSV

PCR utilised primers:

```
HS13
(ACG ACG ACG TCC GAC GGC GA; [SEQ ID No. 1])
and

HS14
(GTG CTG GTG CTG GAC GAC AC  [SEQ ID No. 2])
``` as previously described[10].

These primers anneal to HSV-1 sequence co-ordinates 93536-93555 and 93813-93794 (complementary) which lie within the UL42 region of the genome. This region codes for a sub-unit of the viral DNA polymerase—the DNA polymerase accessory protein.

The resulting PCR product is 278 base-pairs in length and can be visualised by agarose gel electrophoresis.

The reaction conditions used were a 94° C. 'Hot-Start' for 2 minutes followed by 34 cycles of {94° C. for 15 seconds (denaturation); 72° C. for 1 min (annealing); 72° C. for 1 minute (extension)} and a final extension step at 72° C. for 2 minutes.

NTR

PCR utilised primers from the nitroreductase (NTR) enzyme from *E. coli* B genomic DNA. Sequence information for *E. coli* NTR can be found at the NCBI database (ncbi.nlm.nih.gov/) under accession numbers BA000007 (GI: 47118301)—*E. coli* complete genome sequence—and BAB34039 (GI:13360074)—nitroreductase sequence information.

Upstream primer 5'-CTTTCACATTGAGTCATTATGG-3'(SEQ ID No.3); and downstream primer 5'-TTACACTTCGGTTAAGGTGATG-3' (SEQ ID No.4) were used, based on those of Clark et al[15].

Following initial denaturation at 94° C. for two minutes, PCR conditions were 95° C. for 30s (denaturating), 55° C. for 30s (annealing), and 72° C. for 60s (extension), for 32 cycles.

Actin (Control)

The mouse B-actin primers used were:

```
5'-cgt gaa aag atg acc cag a-3';   (SEQ ID No. 5)
and

5'-agc ata gcc ctc gta gat g-3'.   (SEQ ID No. 6)
```

Following initial denaturation at 94° C. for two minutes, PCR conditions were 95° C. for 30s (denaturating) 57° C. annealing temperature and 72° C. (extension) for 60s for 30 cycles.

The results of the PCR analysis, as visualised by agarose gel electrophoresis, are contained in Tables 1 and 2.

Results

The PCR results are consistent for both DNA and RNA. Whilst the DNA PCR results may be used to confirm the presence of the HSV in a particular tissue, RNA PCR provides an indication of virus activity in that tissue. In particular, the RNA results indicate whether the HSV is actively replicating and thus provides information regarding the existence of a pathogenic infection of the cells of a given tissue.

This information may be used in conjunction with the immunohistochemical analysis for corroboration of the results.

A weak positive signal is present in the tumour samples on day 1 increasing to a strong positive signal by day 7. This is consistent for both HSV and NTR PCR for both RNA and DNA and indicates the presence and accumulation of replicating HSV in tumour tissue.

Figure 2:
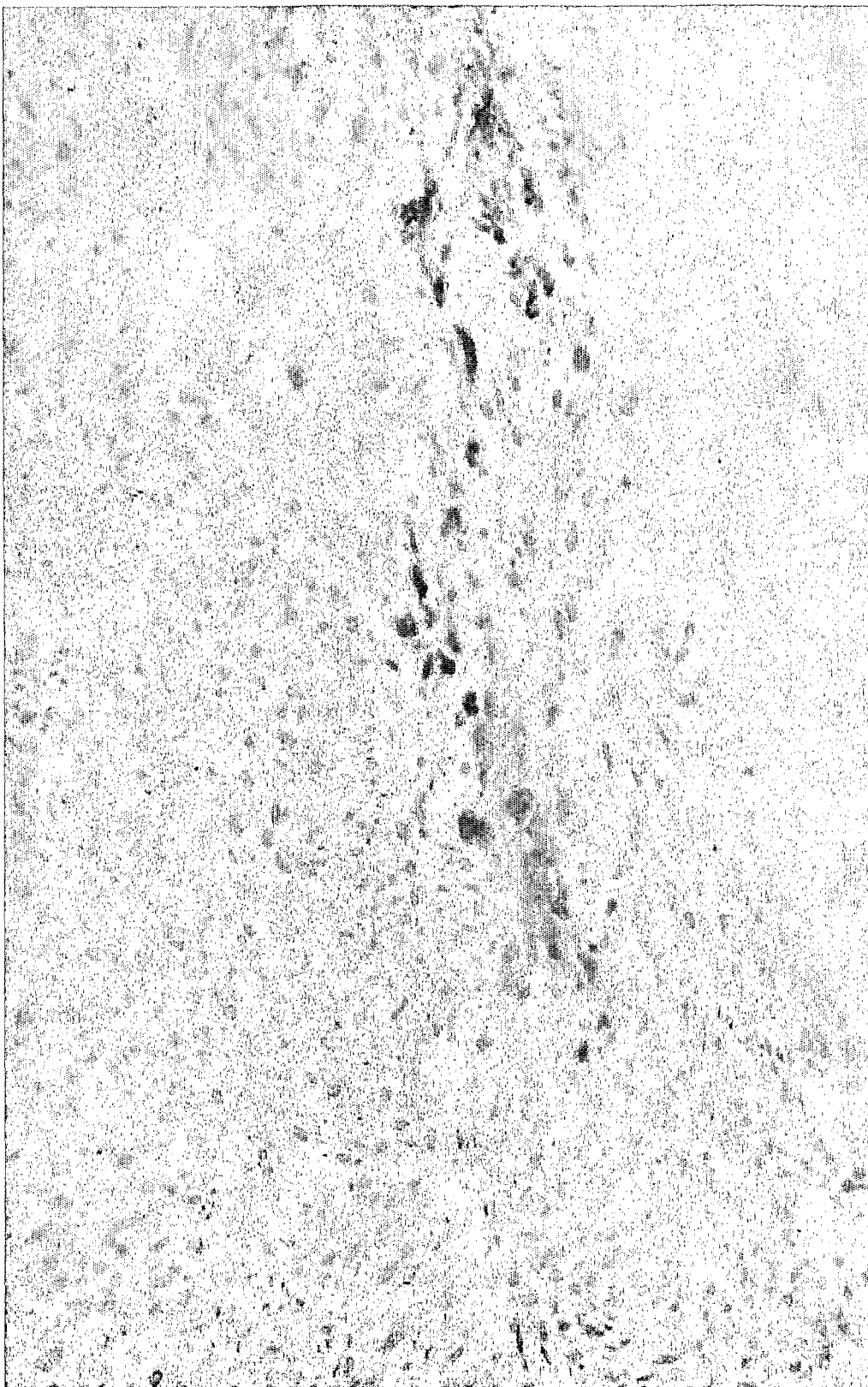
Figure 3:
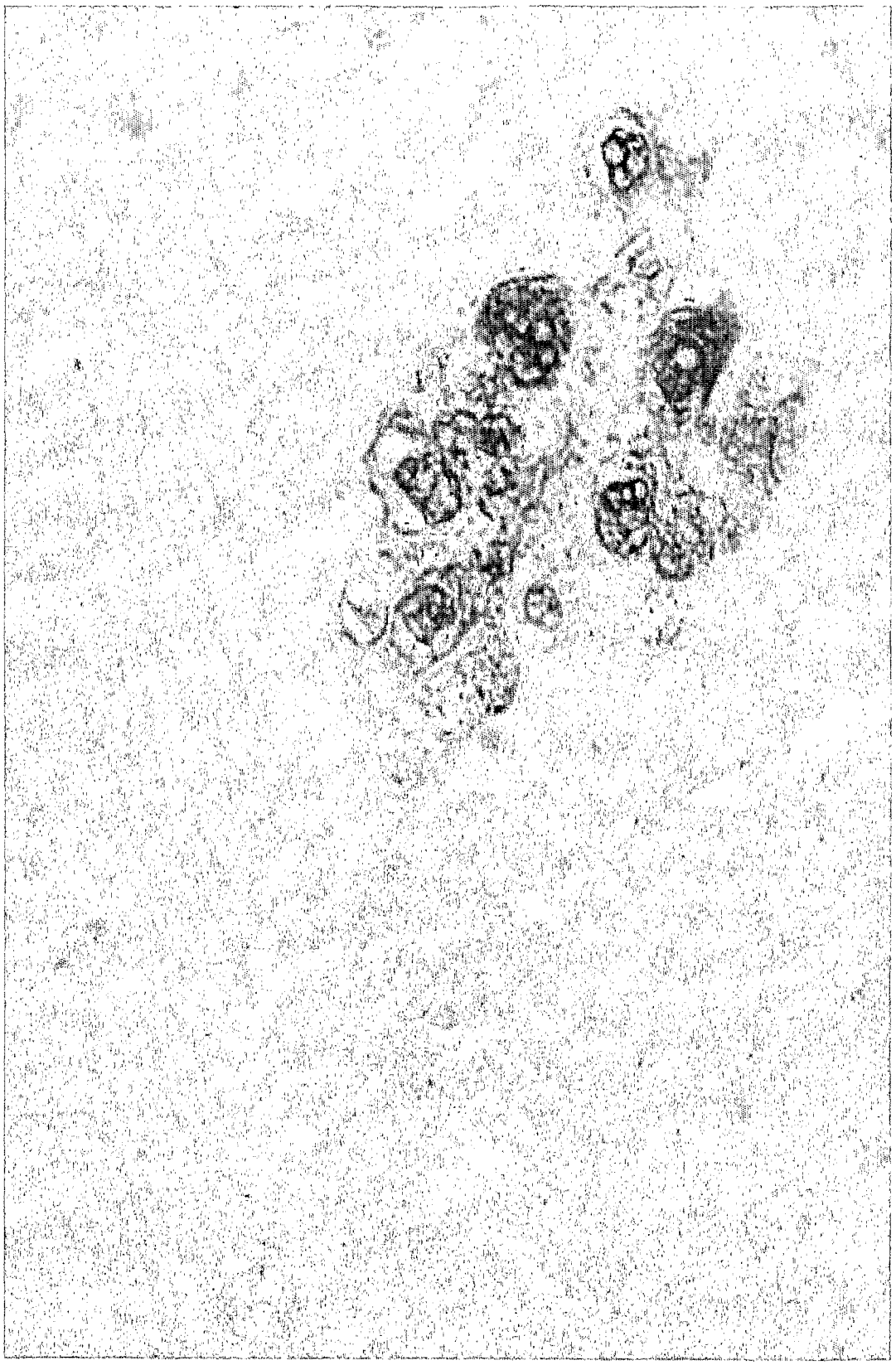
Figure 4:
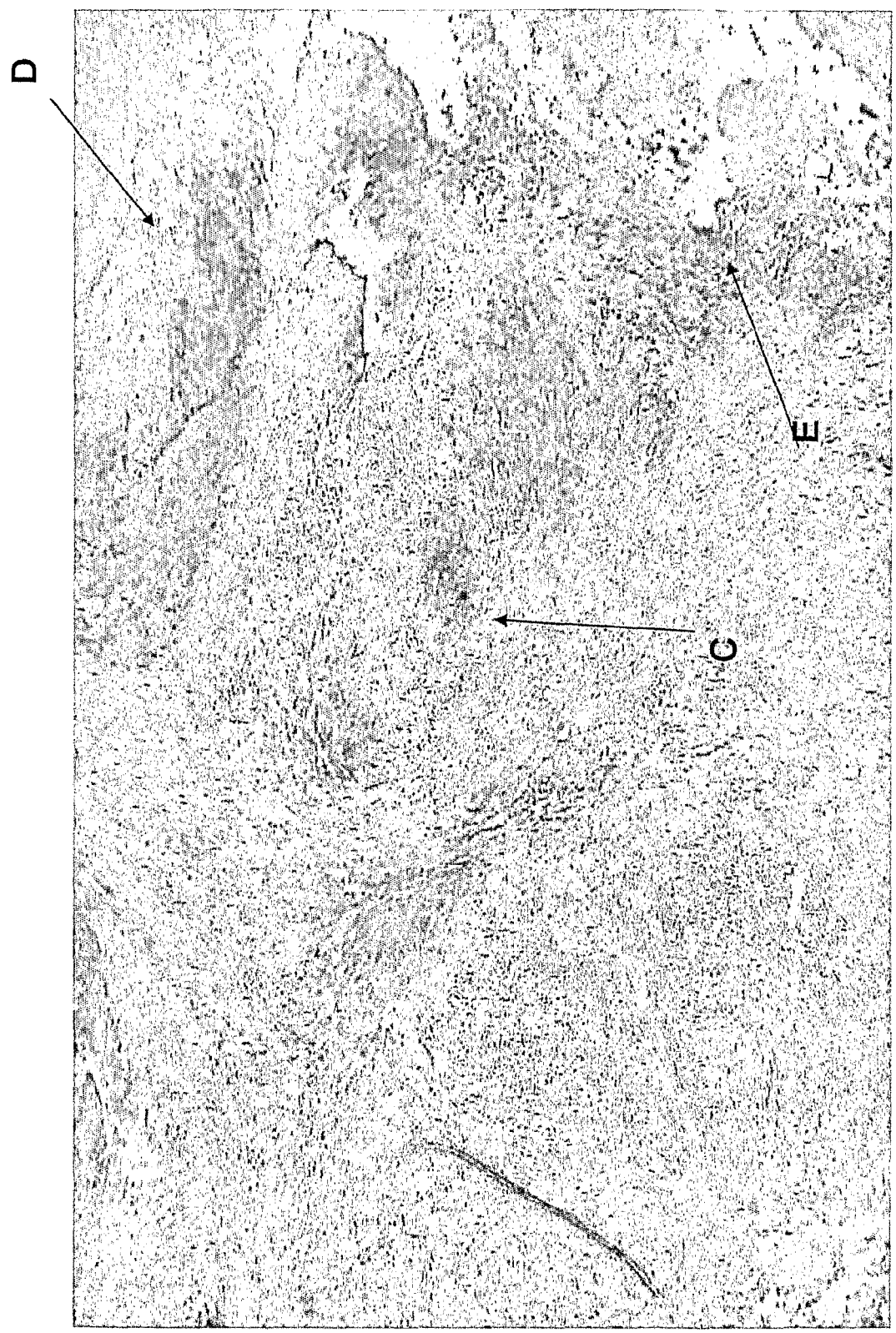

The PCR observations are reflected by the immunohistochemical analysis. FIG. 1 shows positive staining for HSV confirming the presence of HSV in tumour tissue at day 1. FIGS. 2 and 3 show regions of HSV positive staining. In particular, FIG. 3 shows an island of positive HSV staining in which the cells show the classic appearance of HSV infection. The cells are large, multi-nucleated and necrotic.

Figure 7:
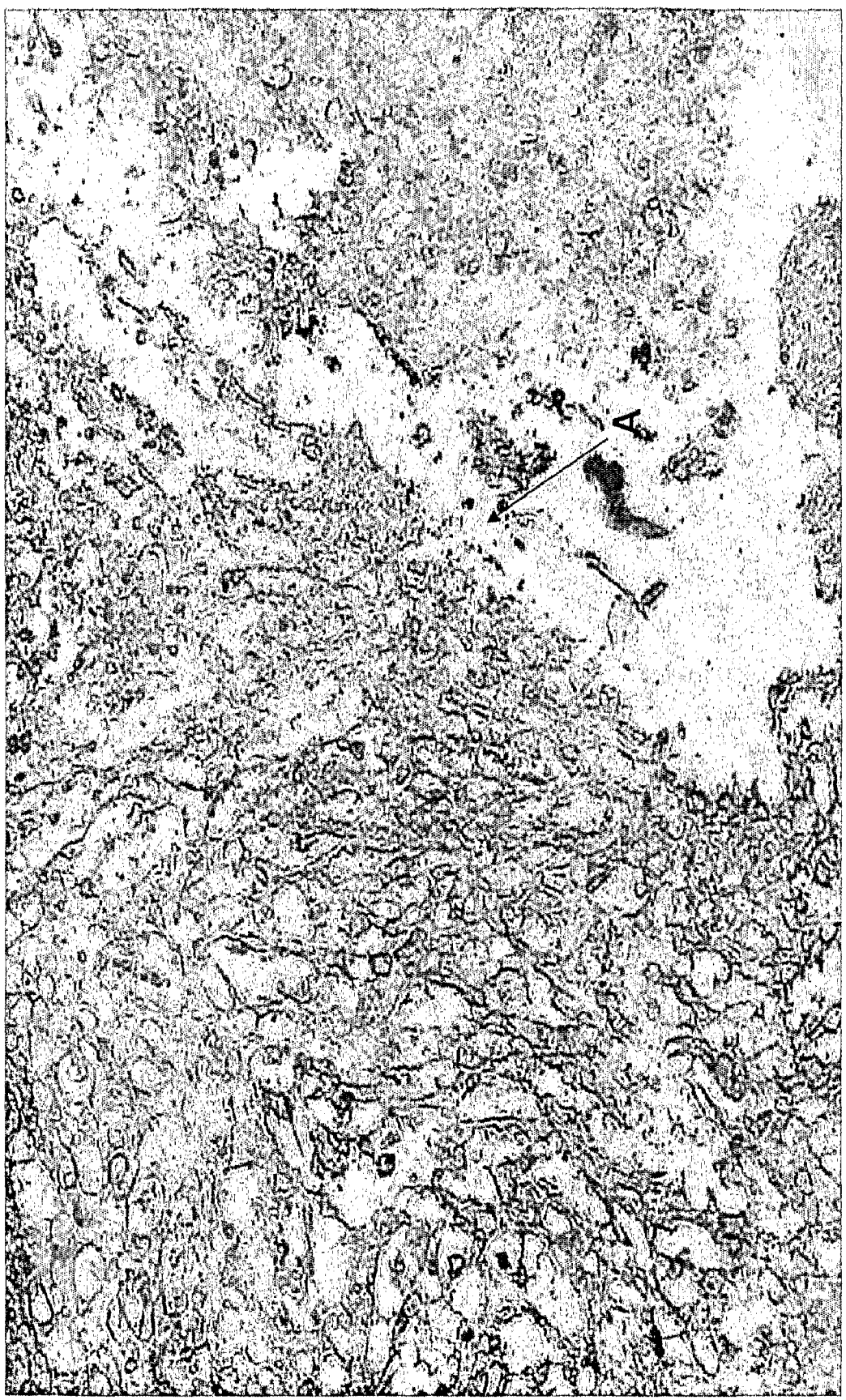
Figure 8:
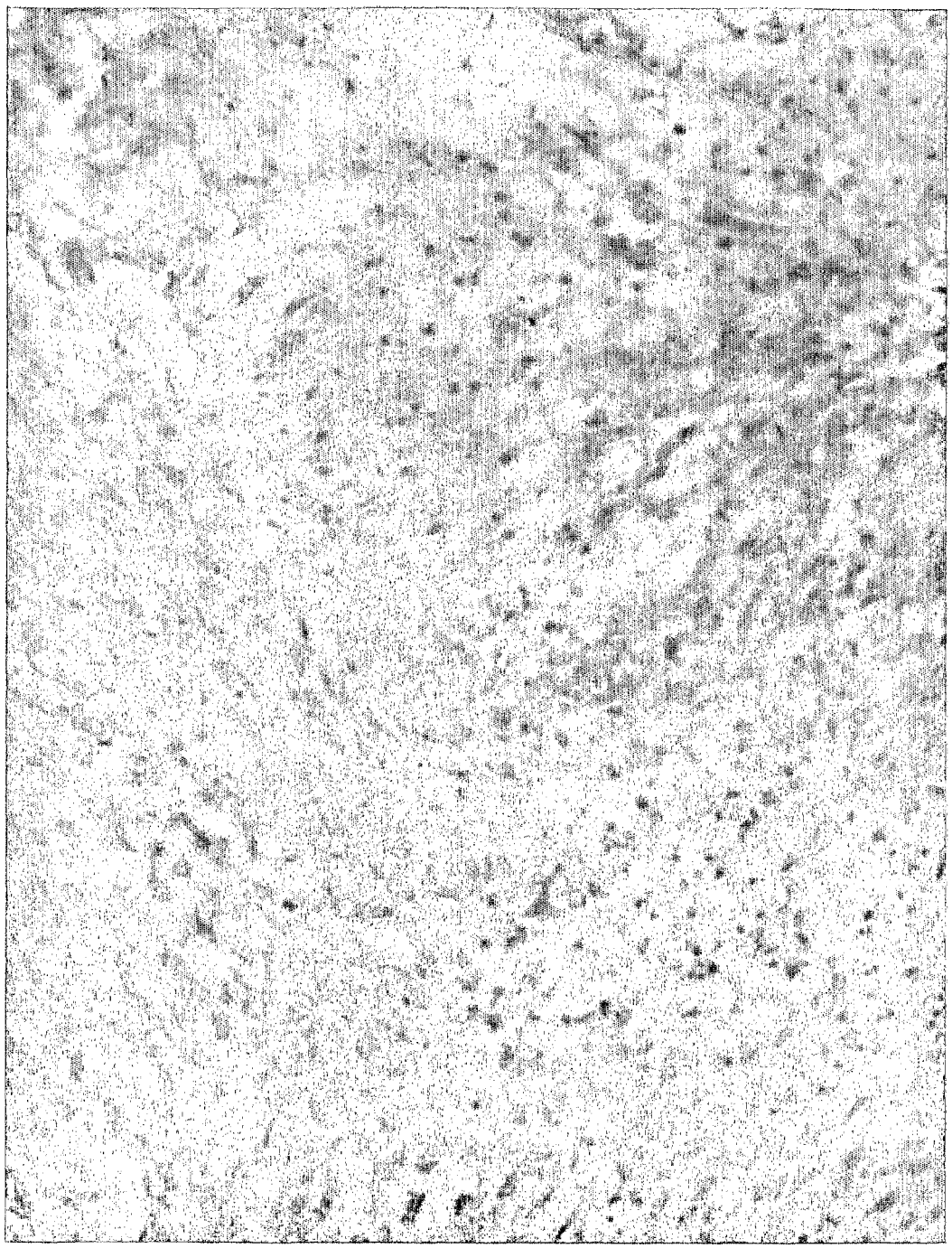
Figure 9:
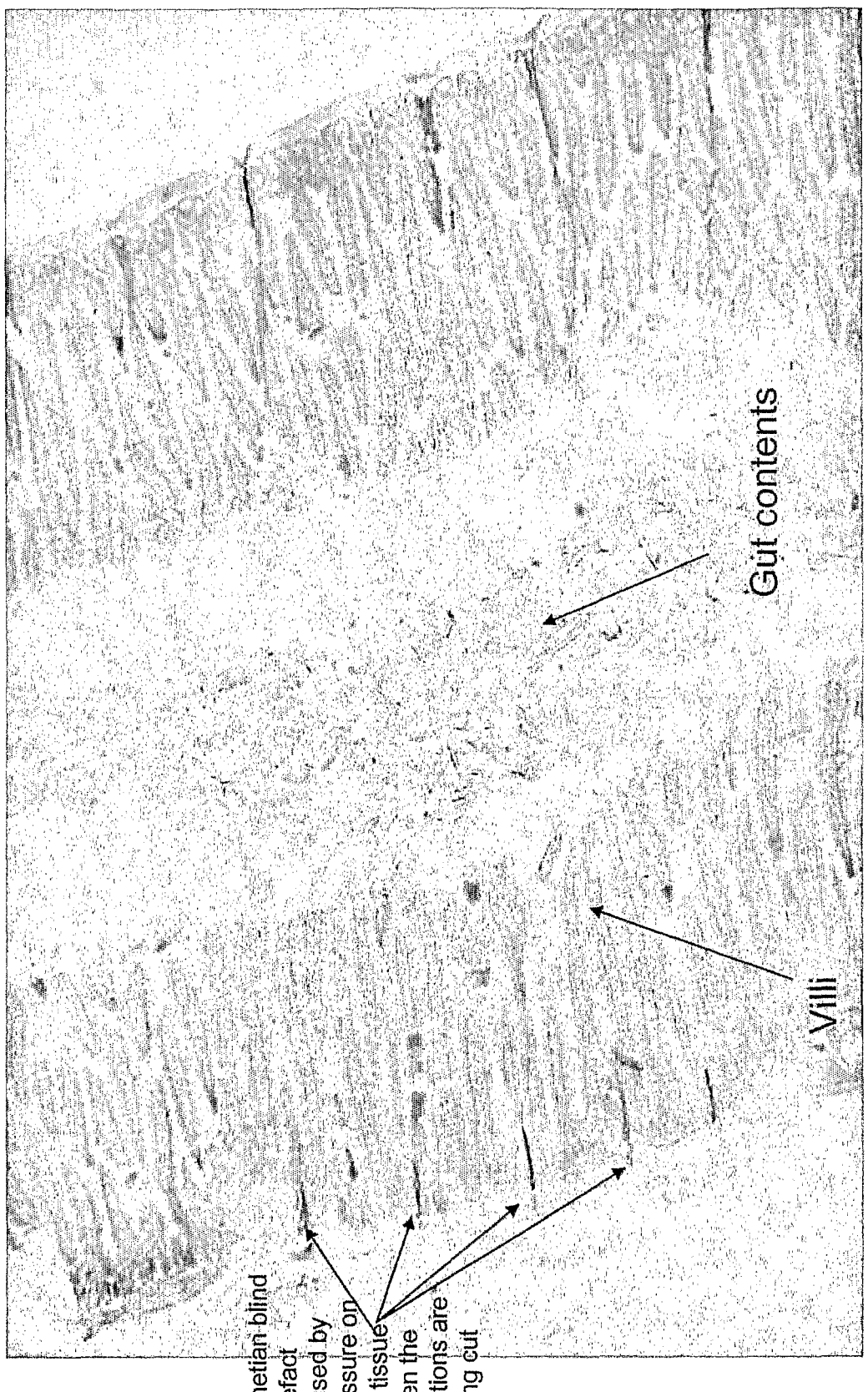
Figure 10:
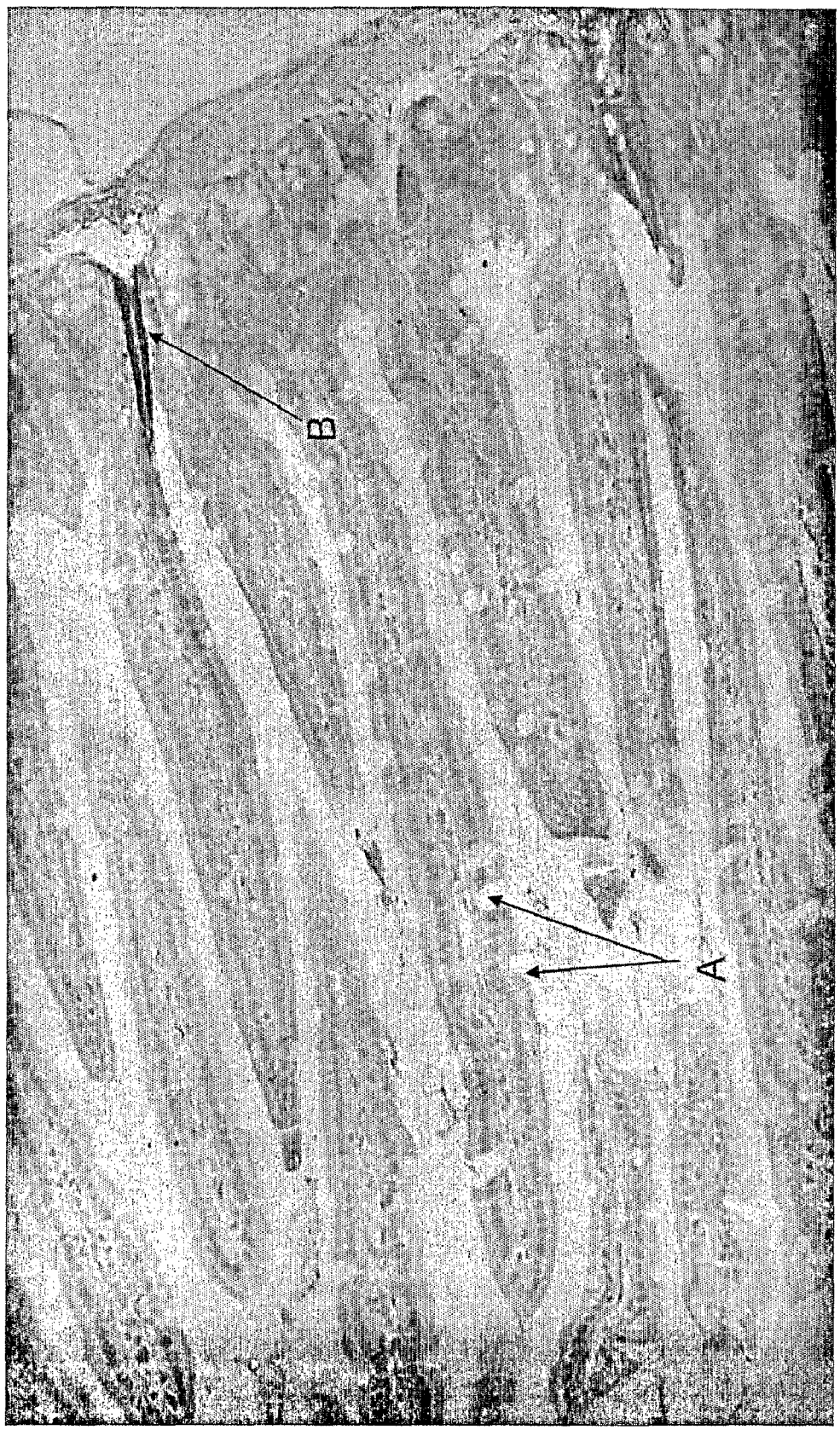

By day 7 (FIG. 4) the areas of HSV staining within tumour tissue are larger and more widespread compared to day 1. FIG. 7 shows an increased magnification view of area E of FIG. 4. The tissue in this region is highly necrotic and cell debris from dead cells is present.

In spleen tissue, the DNA PCR results at day 1 are positive for HSV, but not NTR. The day 1 RNA PCR result was negative for both HSV and NTR indicating that any HSV present is not actively replicating. At day 7 no positive result was obtained either by DNA or RNA PCR of spleen tissue.

Figure 11:
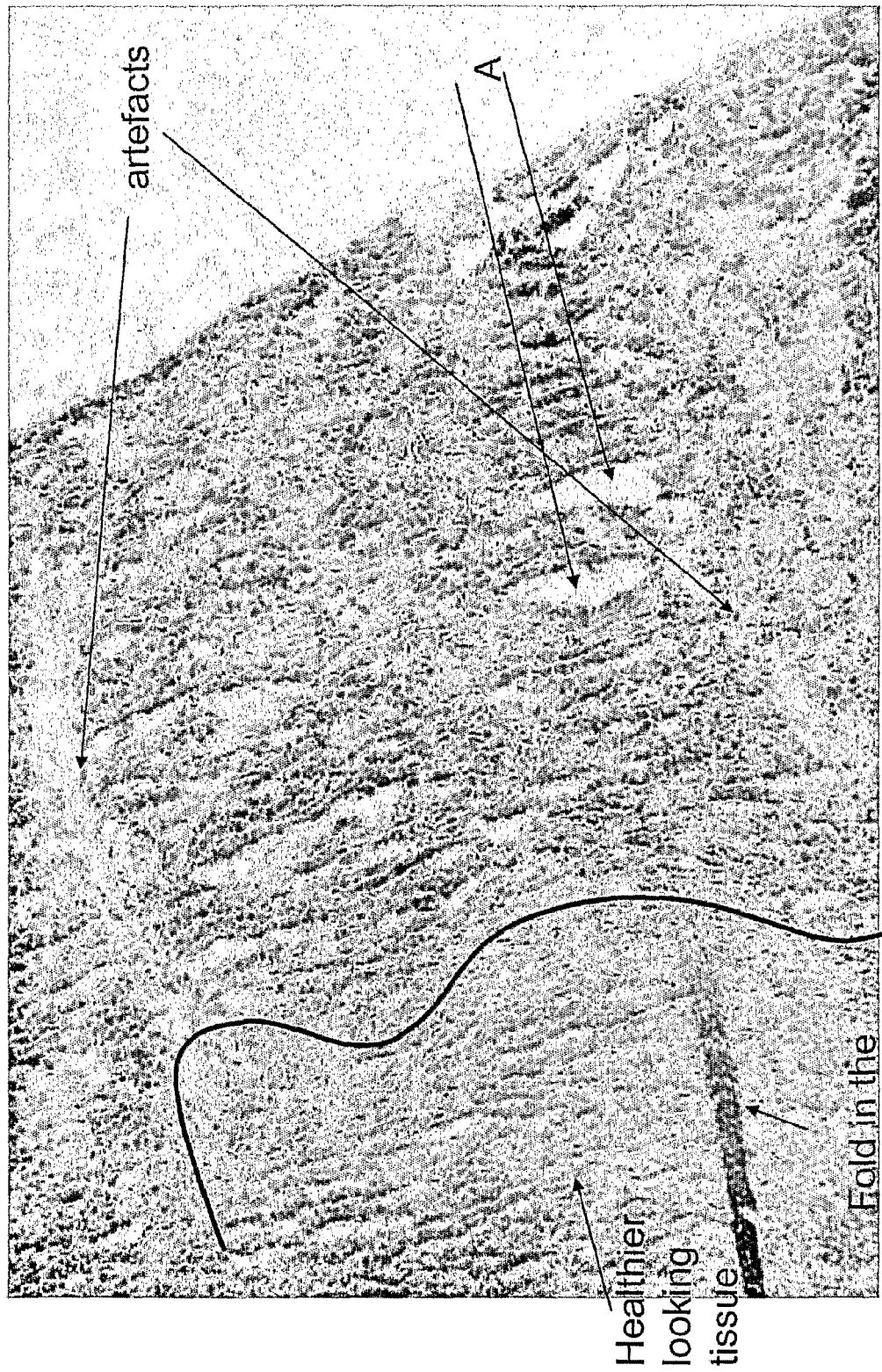
Figure 12:

The immunohistochemical results for spleen tissue are shown in FIG. 11 (day 1) and FIG. 22 (day 7). In FIG. 11 some positive HSV staining is present to the right of the line indicated. By day 7 (FIG. 22) this has decreased and most of the cells are negative for HSV.

These results are consistent with the PCR data that show a loss of HSV in spleen between day 1 and day 7. In view of the fact that the RNA PCR result is negative for spleen tissue at both day 1 and day 7 (indicating that HSV in the spleen are not replicating), this result is most likely attributable to splenic filtering of the blood.

The DNA PCR data indicates weak positive results in blood, skin, gut, heart and liver. These results are weak and are not consistently repeated. Moreover, they are not borne out by the immunohistochemical analysis except for some possible weak positive staining for HSV in skin as shown in FIG. 23. Of course, the RNA PCR results are negative for blood, skin, gut, liver and spleen. Given that the HSV is administered intravenously in the tail vein, the presence of some HSV particles in various tissues owing to the circulation of the HSV particles in the blood is not surprising. Importantly, the RNA PCR results show that HSV replication activity, which may lead to lysis and a therapeutic effect, is exclusively limited to tumour cells by day 7.

The RNA PCR data indicates a medium positive result in heart tissue at day 1. However, in contrast to the results in tumour tissue this result is not consistent for both HSV and NTR, disappears by day 7 and is not borne out by the immunohistochemical analysis which does not show any positive staining for HSV.

Changes in tumour size were not followed in these experiments but preliminary survival data indicates a median survival time of 7 days in the absence of virus and 14 days where virus was administered intravenously. This data supports the ability of the HSV to not only target the tumour, but to treat the tumour and improve survival time.

The results demonstrate that non-neurovirulent HSV-1 mutants of strain 17 may be administered at a site on the body that is distal to a tumour requiring treatment such that the HSV accumulates in the tumour. The results support an increasing accumulation of HSV in the tumour over time and indicate that the HSV may self-target the tumour. HSV RNA production is exclusively limited to tumour cells by day 7 and supports the accumulation of HSV in tumour tissue by exploiting the ability of the oncolytic HSV to selectively replicate in dividing tumour cells. The immunohistochemical analysis provides further support for both HSV infection of tumour cells and necrosis of tumour cells and is consistent with a mechanism of lytic HSV replication in tumour tissue.

TABLE 1

DNA PCR Results

| ID No. | Sample info. | Day | HSV 21/05/05 | HSV 7/6/05 | NTR 21/05/05 | Actin |
|---|---|---|---|---|---|---|
| 350 | Tumour | 1 | + | + | + | − |
| 351 | Blood | 1 | − | + | + | − |
| 352 | Brain | 1 | − | − | − | − |
| 353 | Skin | 1 | − | − | − | + |
| 354 | Lung | 1 | − | − | − | + |
| 355 | Kidney | 1 | − | − | − | ++ |
| 356 | Gut | 1 | − | − | − | +++ |
| 357 | Spleen | 1 | +++ | +++ | − | ++ |
| 358 | Heart | 1 | − | − | − | + |
| 359 | Liver | 1 | − | − | − | ++ |
| 360 | Tumour | 7 | +++ | +++ | +++ | + |
| 361 | Blood | 7 | − | ++ | − | − |
| 367 | Brain | 7 | − | − | − | + |
| 369 | Skin | 7 | + | − | ++ | + |
| 364 | Lung | 7 | − | − | − | + |
| 366 | Kidney | 7 | − | − | − | + |
| 368 | Gut | 7 | − | ++ | − | +++ |
| 362 | Spleen | 7 | − | − | − | ++ |
| 365 | Heart | 7 | + | − | − | + |
| 363 | Liver | 7 | − | ++ | − | ++ |

TABLE 2

RNA PCR Results

| ID No. | Sample info. | Day | HSV 30/04/05 | NTR 06/06/05 | Actin 26/05/05 |
|---|---|---|---|---|---|
| 350 | Tumour | 1 | ++ | − | +++ |
| 351 | Blood | 1 | NI | − | +++ |
| 352 | Brain | 1 | − | − | +++ |
| 353 | Skin | 1 | − | − | +++ |
| 354 | Lung | 1 | − | − | +++ |
| 355 | Kidney | 1 | − | − | +++ |
| 356 | Gut | 1 | − | − | +++ |
| 357 | Spleen | 1 | − | − | +++ |
| 358 | Heart | 1 | ++ | − | +++ |
| 359 | Liver | 1 | − | − | +++ |
| 360 | Tumour | 7 | +++ | ++ | +++ |
| 361 | Blood | 7 | NI | NI | +++ |
| 367 | Brain | 7 | − | − | +++ |
| 369 | Skin | 7 | − | − | +++ |
| 364 | Lung | 7 | − | − | +++ |
| 366 | Kidney | 7 | − | − | +++ |
| 368 | Gut | 7 | − | − | +++ |
| 362 | Spleen | 7 | NI | − | +++ |
| 365 | Heart | 7 | − | − | +++ |
| 363 | Liver | 7 | NI | − | +++ |
| 362 | Spleen | 7 | − | − | +++ |

Key to Tables 1 and 2:
+++ Strong band on gel
++ Medium band on gel
+ Weak band on gel
− No band
NI Non-informative—contaminated with DNA (RNA only)

EXAMPLE 2

Evaluation of the Anti-tumor Activity of a Selectively Replication Competent Herpes Simplex Virus in Combination with Enzyme Prodrug Therapy HSV1790 is a second generation oncolytic virus generated by inserting the bacterial enzyme nitroreductase (NTR) into the oncolytic virus HSV 1716, under the control of the CMV IE promoter. NTR converts the inactive prodrug CB1954 into an active alkylating agent which has an anti-tumor effect. The purpose of this study was to determine the anti-tumor efficacy of the combination of HSV1790 and CB 1954 in vitro and in vivo, and to explore the efficacy of this combination after systemic (intravenous) administration of HSV1790.

Experimental Design:

In vitro, cells which are known to be non permissive for HSV 1790 replication were used in order to distinguish between an oncolytic effect due to viral replication, and cell death due to activated prodrug.

In vivo, intratumoural administration of HSV1790 ($10^5$-$10^9$ PFU) with, or without administration of CB1954 (max 80 mg/kg) by the intraperitoneal route was performed on mouse xenograft models of A2780, CP70 and A431 cell lines, and tumor volume measured regularly. Tumor and organ distribution of HSV1790 following intravenous administration was determined by immunohistochemistry and by analysis of DNA and RNA from harvested tumor tissues and organs.

Administration of HSV 1790, followed by CB1954, enhanced tumor cell killing in 3T6 cells compared to HSV1790 alone. In vivo, the combination of intra-tumoral administration of HSV1790, followed by intraperitoneal CB1954, enhanced tumor reduction and improved survival compared to administration of virus alone. Following systemic administration of HSV1790, viral replication is detected in tumor tissue, but not in normal organs.

HSV1790, when used in combination with CB1954, can enhance tumor cell killing in vitro and enhance tumor reduction and survival in vivo without toxicity in normal tissues and organs.

Introduction

Cancer is a genetic disease, and the hallmarks of individual cancer cells are mutations in genes related to growth control, apoptosis, immortality and also functional aberrations that support the ability of cancer cells to invade and metastasize (1). Genetic therapies in cancer are designed to produce one of several types of outcome. Firstly, the genetic material introduced into the host or tumor may result directly in cancer cell death, for example by the intratumoral administration of a replication competent virus. Secondly, the genes introduced into the host or tumor cells are expressed, and can induce an immune response directed against the tumor (2). Thirdly, the gene product may be toxic to the tumor cell or may activate a subsequently administered drug into a cytotoxic agent that results in cancer cell death. This approach is frequently described as 'gene directed enzyme pro-drug therapy' (GDEPT) or 'suicide gene therapy' (3).

Herpes simplex virus type 1 (HSV-1) has a number of pertinent characteristics that support its use in cancer therapy. It infects a broad range of cell types, it is cytolytic by nature (the life cycle of the virus results in host destruction), and it has a well characterized and, in the case of Glasgow strain 17+, a fully sequenced genome (4). Furthermore, its large genome (152 kb) contains non essential genes that can be replaced by therapeutic transgenes of up to 30 kb (5). HSV1716 is a selectively replication competent mutant of the HSV-1 in which both copies of the RL1 gene has been deleted (6). The RL1 gene encodes the protein ICP34.5, which is a specific determinant of virulence (7). ICP34.5 functions by complexing with proliferating cell nuclear antigen (PCNA), which is involved in DNA replication and repair (8). In most tumor cells, PCNA levels are high, and ICP34.5 is not required for productive HSV replication. In contrast, in normal, terminally differentiated cells, PCNA levels are low and ICP34.5 is required to recruit any available PCNA to initiate virus replication. Thus HSV1716 replicates in actively dividing but not terminally differentiated cells (9), and has an antitumor effect in vitro in a range of tumor cell types including gliomas (10).

HSV 1716 has demonstrated selective tumor cell killing, with minimal toxicity, and its administration has resulted in improved survival in a number of xenograft tumor models in mice, including glioma (1 1), melanoma (12-14), mesothelioma (15), ovarian (161, lung (17, 18) and breast (19) carcinomas. Clinical trials of intra-lesional administration of HSV1716 in patients with glioma, melanoma and squamous cell carcinoma of the head and neck have been performed (20-23) and have demonstrated the safety of this approach, and with evidence that the virus is capable of directly destroying human tumor cells while leaving normal cells intact.

One potential limitation of the intra-lesional administration of HSV1716 for the treatment of human tumors is that there is heterogeneity of cell type and growth state within a tumor, and consequently not all cells within a tumor will be permissive for lytic replication by HSV1716. One strategy to overcome this limitation is to combine the oncolytic effects of HSV1716 with a gene-directed enzyme prodrug therapy approach. A number of enzyme pro-drug systems have been proposed for cancer gene therapy (24), including the E. Coli nitroreductase (NTR) with the pro-drug CB1954 (25-27). CB1954 [5(aziridin-1-yl)-2,4-dinitrobenzamide] is a monofunctional alkylating agent that is poorly metabolized in human cells and thus has low toxicity. The enzyme, NTR, converts the inactive CB 1954 pro-drug into its active form, which is a functional cytotoxic alkylating agent that introduces poorly repaired inter-strand cross-links into DNA and these lesions kill cells regardless of their cell cycle state (28). In addition, the active metabolite is diffusible and membrane permeable—this results in an efficient bystander effect (29, 30). We have generated and characterized a second generation virus (HSV1790) which contains the E. coli nitroreductase gene inserted into the RL1 locus of the HSV1716 genome. As the virus should only replicate and produce NTR in tumor cells, toxicity to normal cells should be avoided. In this manuscript, we report the generation of this second generation virus, and demonstrate that the combination of HSV 1790 and the prodrug CB 1954 has enhanced tumor cell killing in vitro, and results in improved tumor reduction and survival in vivo compared to the oncolytic effect of HSV 1790 alone.

Another potential drawback in the application of genetic therapies in cancer medicine is that administration of the genetic therapeutic usually requires direct injection into the patient's tumor. Consequently many of the clinical trials of these therapies have been restricted to patients with localized tumors that are accessible by direct injection or by injection under radiological guidance or post operatively. However, patients with advanced cancer invariably have metastatic disease or tumors that are inaccessible for direct injection. In this manuscript we report safety and efficacy data after systemic (intravenous) administration of HSV1790 in athymic mice bearing human tumor xenografts. We demonstrate that the virus selectively locates to tumor tissues, replicates and produces NTR within tumors without affecting other organs. Furthermore, tumour reduction, and enhanced survival, is observed in vivo in tumor bearing mice following pro-drug administration. These studies indicate that systemic administration of HSV1790 and CB1954 should be explored further in human clinical trials.

Materials and Methods

Construction of HSV-1 Recombinant Virus Expressing ntr:

The plasmid pPS949, containing the ntr gene downstream of the CMV IE promoter (pCMV-NTR) in a pLNCX (Clonetech) backbone, was a kind donation from Professor Lawrence Young (University of Birmingham). The pCMV-NTR fragment was excised from pPS949 and cloned into BglII digested, CIP treated RLI-.dIRES-GFP. Clones were screened for the pCMV-NTR insert using BglIIXhoI restriction enzyme analysis and one clone was found to contain the insert in the correct orientation (data not shown). The plasmid RLI.dCMV-NTR-GFP was digested with ScaI which cuts in a region outwith the flanking sequences and the PCMV-NTR-IRES-GFP-PolyA fragment. BW cells were co-transfected with the linearised plasmid and HSV17+ DNA. Recombinant virus was identified using GFP fluorescence and several green plaques were plaque purified as described in (31). To ensure that recombination had taken place in the correct location and that the endogenous copy of the RL1 gene had been replaced by the pCMV-NTR-IRES-GFP-Poly A cassette, DNA from HSV1790 was purified, digested with BamHI and analysed by Southern Blot (data not shown). FIG. 32 shows a schematic representation of HSV1716/CMV/NTR (designated HSV 1790 and referred to as such hereafter) genome and relevant fragment sizes expected from BamHI digestion of HSV 1790 DNA.

Cell Cultures:

BHK (baby hamster kidney 21 clone 13) cells and mouse embryo 3T6 cells were obtained from the European Collection of Cell Culture (ECACC). BHK cells were grown in Eagle's medium supplemented with 10% newborn calf serum and 10% (v/v) tryptose phosphate broth. This will be referred to subsequently as ETC 10. For virus titrations and plaque purification EMC10 (Eagle's medium containing 1.5% methylcellulose and 10% newborn calf serum) was used to overlay the cells. The ovarian cell lines A2780 and CP70 (obtained from ECACC) were cultured in RPMI 1640 medium supplemented with 10% fetal calf serum. Cell cultures were incubated in a humidified atmosphere of 5% $CO_2$/95% $O_2$ at 37° C. The squamous cell carcinoma cell line A431, cervical carcinoma C33a and the glioma line U373MG were all obtained from the American Tissue Culture Collection (-ATCC) and were cultured in DMEM containing 10% fetal calf serum and incubated in a humidified atmosphere of 10% $CO_2$/90% $O_2$ at 37° C. All cultures were tested for *Mycoplasma* using VenorGeM® *Mycoplasma* PCR Detection Kit (Cambio, Cambridge, UK). Titration of virus stocks was carried out as previously described in (32).

Western Blotting:

Western blotting was carried out using standard techniques. For NTR detection a rabbit polyclonal anti-NTR antibody was kindly provided by Professor Lawrence Young (University of Birmingham, UK) and used at a concentration of 1/1000. The secondary antibody, goat anti-rabbit IgG peroxidase conjugate (Sigma) was also used at 1/1000.

In vivo tumor reduction and biodistribution studies. Female 6-8 week old athymic nude mice (Charles River Labs) were maintained under specific pathogen free conditions and in isolation after virus injection.

Actively growing A2780, CP70 and A431 cells were harvested and resuspended in phosphate buffered saline (PBS). Cells ($1 \times 10^7$ for A2780 and A431, $5 \times 10^6$ CP70 per mouse) were injected into the flanks of athymic mice. The mice were examined regularly for tumor growth. When the mean tumor diameters were approximately 5 mm, the animals were randomized into groups. HSV 1790 or HSV1716 or PBS (maximum volume 100 µl) was administered by direct intratumoral injection. Virus was diluted in PBS+10% fetal calf serum and kept at -70° C. until use. CB1954, resuspended in archais oil with 10% acetone was then administered by intraperitoneal injection (maximum volume 100 µl, maximum dose 3×80 mg/kg) at least 48 hrs after viral injection. For general examination of toxicity, animals were weighed regularly and tumor volumes were calculated from caliper measurements (volume=$d^3 \times \pi/6$). For statistical analysis, unpaired Student's t-tests were used. P values of <0.05 were considered significant. All animal experimentation was performed according to United Kingdom Home Office regulations and UKCCR guidelines adhered to at all times.

Immunohistochemistry:

Organs and xenograft tumor samples were removed immediately from individual mice after sacrifice and fixed in neutral buffered formalin (NBF) for at least 24 hrs before embedding in paraffin using standard procedures, Sections were prepared for immunohistochemistry by standard protocols. Briefly, paraffin embedded sections were dewaxed, dehydrated and endogenous peroxidase was quenched. Non-specific binding was reduced with 10% normal goat serum before sections were incubated with primary antibody overnight at 4° C. (HSV-1 polyclonal, Dako 1:1000).

After incubation with biotinylated secondary antibody (Vector anti-rabbit Elite kit 1:500) and avidin biotin complex (ABC) solution (Elite Kit, Vector Laboratories) color was developed using diaminobenzidine (DAB) (Vector Labs) as the chromogen. The slides were counterstained, dehydrated, mounted and visualized using a light microscope. HSV-1 infected liver sections were used as a positive control, omission of primary antibody and tumor sections from mice uninfected with virus constituted the negative controls.

Extraction of RNA and DNA from tissues—(RNA):

Tumor tissue and mouse internal organs were collected from individual mice at time of sacrifice and frozen at -70° C. A small (<0.5 g) tissue sample was resuspended in buffer and the cells were disrupted with a Retsch MM200 homogenizer. RNA was extracted using the Promega (SV) RNA extraction kit following the manufacturers recommended procedure (Promega, Southampton, UK).

DNA:

Tissue (<0.5 g) samples were homogenized using the Retsch MM200 homogenizer and DNA extracted using the Nucleon ST DNA extraction Kit (Thistle Scientific Ltd, Glasgow, UK) using the manufacturers instructions.

Reverse Transcriptase Reactions:

Reverse transcription was preformed using ImProm Reverse transcriptase kit (Promega, Southampton, UK) using the random hexanucleotide primers under manufacturers recommended conditions.

PCR:

PCRs were carried out with Ready-Mix (Abgene, Surrey, UK) and 1 µl of RT reaction mix in a 20 µl reaction volume. For HSV PCR the primers HS 13 (ACG ACG ACG TCC GAC GGC GA) [SEQ ID No.7] and HS 14 (GTG CTG GTG CTG GAG GAC AC) (34) [SEQ ID No.8] were used. These anneal to HSV-1 sequence co-ordinates 93536-93555 and 93813-

93794 (complementary) which lie within the UL42 region of the genome. This region codes for a sub-unit of the viral DNA polymerase—the DNA polymerase accessory protein. The resulting PCR product is 278 base-pairs in length and was visualized by agarose gel electrophoresis. The reaction conditions used are a 94° C. 'Hot-Start' for 2 minutes followed by 34 cycles of {94° C. for 15 seconds (denaturation); 72° C. for 1 min (annealing); 72° C. for 1 minute (extension)} and a final extension step at 72° C. for 2 minutes. For NTR: The PCR used the primers sequence of the nitroreductase (NTR) enzyme from $E.\ coli$ B genomic DNA. Upstream primer 5-TTTCACATTGAGTCATTATGG-3 [SEQ ID No.9] and downstream primer 5-TTACACTTCGGTTAAGGTGATG-3 [SEQ ID No.10] were used (35). Following initial denaturation at 94° C. for two minutes, PCR conditions were 95° C. for 30s, 55° C. for 30s and 72° C. for 60s, for 32 cycles.

Results

Expression of NTR in cell lines infected with HSV1790. To demonstrate that HSV1790 expresses the NTR protein a Western blot was performed using a polyclonal NTR antibody. Although the recombinant virus strongly expressed GFP (observed during the plaque purification process) indicating that it should express NTR, this was not conclusive proof. Four cell lines—BHK, C8161, VM and 3T6 were infected with HSV1790 and protein expression analysed by Western blotting, using an NTR-specific antibody. FIG. 33 shows that the 24 KDa NTR protein was expressed in all the cell lines infected with HSV1790. Even though the virus does not replicate efficiently in confluent 3T6 cells, reasonably strong expression of NTR was detected demonstrating that productive replication of the virus is not necessary for NTR expression in infected cells.

Enhanced cell kill in vitro in HSV1790 infected cells treated with CB1954.

Previous experiments had shown the replication kinetics of the virus to be identical to that of the parental strain HSV 1716 indicating no alteration in replication potential due to the insertion of the ntr gene (Paul Dunn, PhD Thesis, University of Glasgow, 2003). To determine whether NTR expression would result in enhanced cell killing after HSV1790 infection and addition of the prodrug CB1954, cytotoxicity assays were performed in 3T6 cells, a cell line in which the HSV did not replicate efficiently. As almost no HSV1790 replication occurs in 3T6 cells infected at a low MOI (>0.1), any significant cell death observed in the cells infected with HSV1790 after CB1954 administration would be due to NTR expression in the cells, and the subsequent activation of CB1954. The addition of 50 pM CB1954 alone had previously been shown to cause less than 5% cell death-(data not shown). The effects of HSV1790 infection, with or without 50 pM CB1954, were examined and the results shown in FIGS. 34 and 35. Five days after treatment, 75% of the cells treated with 10 plaque forming units (pfu)/cell HSV1790+CB1954 were dead compared to only 2% in those treated with HSV1790 only (FIGS. 34 and 35). It can therefore be concluded that almost 70% of the cell death observed in the HSV1790 infected cells was due to NTR converting CB1954 to its toxic form and not from cell lysis from viral replication.

HSV1790 Toxicity and Efficacy in Vivo.

No formal toxicity studies were performed. However in preliminary experiments, the dose of HSV1790, administered by a single intratumoral injection, was escalated in groups of mice bearing A2780 human tumour xenografts (n=3) to determine the acceptable dose for subsequent experiments, based on toxicity. A dose of $1\times10^9$ pfu HSV1790 by intratumoural injection was not tolerated well; the mice lost more than 10% of their body weight and had to be sacrificed. At doses of $1\times10^8$ and below, the treatment was well tolerated and the mice did not show any signs of ill health or adverse effects.

To determine the efficacy of HSV1790+CB1954 in treating established subcutaneous human tumour xenografts, serial tumour volume measurement were taken regularly after administration of HSV1790 alone, HSV1790+CB1954 or no treatment. Administration of CB1954 alone was not performed as previous experiments had shown that CB1954 administration as a single agent has no anti-tumoral effect (data not shown). Two doses of virus were administered as giving multiple intratumoral injections appears to be more effective than the administration of the same total dose on one occasion (36). CB1954 treatment was commenced 48 hrs after the last virus injection (max 80 mg/kg on 3 occasions). Previous experiments in vitro (data not shown) and (36) suggested that administering the prodrug too soon after viral administration kills the cells in which the virus is replicating, effectively thereby reducing the number of infectious virus particles within the tumor. Administration of HSV1790 and CB1954 had no effect on body weight (data not shown) and there were no signs of toxicity in the mice. In mice bearing A2780 (FIG. 36A) and A431 (FIG. 36C) xenografts, there was a marked reduction in tumor volume when the xenografts are treated with HSV1790+CB1954 compared to HSV 1790 alone. For mice bearing A431 tumours, administration of HSV1790+CB1954 resulted in significantly smaller tumour volumes (P=0.03) and significantly longer median survival (P<0.05) (FIGS. 36C and F) than in the mice treated with HSV1790 alone. In mice bearing CP70 tumor xenografts, administration of HSV1790 reduced tumor volume compared to control mice (FIG. 36B) but the addition of prodrug had no further anti-tumor effect.

Tumor and Organ Distribution of HSV1790 after Systemic (Intravenous) Administration.

To explore the tumor and organ distribution of HSV1790 after systemic (intravenous) administration, $1\times10^7$ pfu of HSV1790 was administered by tail vein injection to athymic nude mice bearing established UVW and A431 tumour xenografts overlying their right hind flank. Mice were sacrificed either on day 1 or day 7 post injection and the tumors, blood and major organs (brain, heart, lung, liver, spleen, intestine, kidney and skin) were collected. Tissue from these organs was analysed by PCR and immunohistochemistry for the presence of HSV1790. Immunohistochemical staining with an anti-HSV antibody revealed active replication of the virus within the xenograft tumours (FIG. 37A-F) Necrosis was also widespread in the areas of positive staining (FIG. 37F). There was no indication of positive staining in any other organ (FIG. 37G-J) with the exception of skin; in which some positive staining was visible in cells below the dermal and epidermal layer (FIG. 37K).

DNA and RNA, extracted from the organs and tumours were also analysed by PCR, to determine presence of virus and the replication of the virus (FIG. 38). Both viral DNA and RNA are detected in the tumour tissue at day 1 post i.v injection at a low level. By day 7 post i.v injection the PCR band intensity has increased, demonstrating that HSV is replicating within the tumor tissue. Furthermore ntr DNA and RNA is detectable in the tumor demonstrating that HSV1790 is replicating within the tumor and is also producing the ntr protein. A high level of viral DNA is seen in the spleen at day 1. However there is no replicating virus detectable by RT-PCR. This suggests that the virus is not actively replicating and the positive PCR result is likely to be due to spleenic clearance of the virus from the circulating blood.

Tumor Growth Inhibition in Athymic Nude Mice after Administration of HSV1790 by Intravenous Injection.

To determine whether HSV1790 replication within tumors seen after intravenous injection has any anti-tumor effects, mice with A431 xenografts were randomly allocated into groups:

(a) 2× ($1 \times 10^6$) PFU of HSV1790 injected i.v (intravenous) at Days 1 and 3 followed by 20 mg/kg injection CB1954 i.p (intraperitoneal) daily for 5 days;
(b) 2× ($1 \times 10^6$) PFU of HSV1790 injected i.v at Days 1 and 3;
(c) No virus injections (injection of PBS only).

FIG. 39 show that HSV1790 either alone or in combination with CB1954 results in significantly prolonged survival of tumor bearing mice.

Discussion

We have previously described the safety and potential efficacy of herpes simplex virus therapy using the selectively replication competent mutant HSV1716 both in vivo (11-19) and in clinical studies (20-23). However, it is anticipated that HSV1716 although able to infect all cells will not lyrically replicate in all cells within tumors due, predominantly, to the heterogeneity of the cell state within a tumor mass. To overcome this, we have generated HSV1790, a second generation herpes simplex virus derived from the ICP34.5 null mutant HSV1716 and in which the E. Coli ntr gene has been inserted under the control of the CMV IE promoter.

Western blot analyses demonstrated that the ntr protein was expressed in all four cell lines tested following infection with HSV1790. Furthermore, the addition of the prodrug CB1954 to 3T6 cells infected with HSV1790 resulted in a significantly enhanced cell kill compared to infection with HSV1790 alone. Administration of the prodrug CB1954 to athymic mice, bearing tumor xenografts of either A431 or A2780 cells, 48 hours after intratumoral administration of HSV1790 resulted in a marked reduction of tumor volumes, and also resulted in significantly improved survival for mice bearing A431 tumors, compared to administration of HSV1790 without administration of CB1954. In contrast, administration of CB1954 following administration of HSV1790 to mice bearing CP70 tumor xenografts had no additional anti-tumor effect compared to administration of HSV1790 alone. CP70 is a derivative of the ovarian carcinoma cell line A2780, and has a drug-resistant phenotype due to the loss of MLH1, a key protein involved in mismatch repair (37, 38). These cells display resistance to a variety of DNA damaging agents and alkylating agents. CP70 has a higher tolerance of CB1954 than the parental A2780, with $IC_{50}$ values in vitro of 29 μM and 60 μM respectively (39).

Expression of NTR in these cells results in similar-fold sensitisation to the prodrug, with the value for A2780 remaining approximately half of that for CP70 cells (39). As the active form of CB 1954 is a bi-functional alkylating agent, it is possible that the intratumoral activation of CB 1954 to its active form by NTR expression, following HSV1790 administration, is insufficient to overcome the drug resistant phenotype of these CP70 cells.

Expression of a prodrug activating enzyme early in the virus replication cycle risks killing the virus (40, 41). In addition, the insertion of a transgene could theoretically worsen virus efficacy in vivo. However, neither of these potential drawbacks is likely with HSV1790 based on the results reported in this manuscript. Another potential drawback of combining an oncolytic virus with a 'suicide-gene therapy' approach is that if the virus alone can induce efficient cytopathic effects, then the transgene may not be expressed in target cells prior to the cell death, and there may be no additional therapeutic benefit to the combined approach. Again, the data presented in this manuscript suggests that the second generation virus HSV1790, when combined with the addition of the prodrug, has an enhanced anti-tumor efficacy compared to HSV1716.

Most human clinical trials of genetic therapies for cancer, including those using oncolytic viruses, continue to use direct intra-tumoral injection as the route of administration of the therapeutic virus. However, as most patients have metastatic disease, the preferred route of delivery of oncolytic viruses is through intravenous administration. Intravenous administration of viruses can cause significant systemic side effects, due to the acute release of cytokines. These symptoms can be effectively minimised by appropriate pre-radiation (42-44) and intravenous administration of Newcastle Disease Virus (42, 43) and Onyx 015 (44, 45) have been well tolerated in initial clinical studies with minimal toxicity.

Our results demonstrate replication of HSV1790 and expression of the ntr transgene within tumor tissue following intravenous administration, but with no evidence of viral replication in normal organ tissues. However, as athymic nude mice have a compromised immune system, the effect of a normal immune system on viral toxicity and efficacy is unknown. Viral infection of tumors can attribute an anti-tumor immune response which is beneficial (13, 46, and 47). In contrast, the host's immune system has been shown to neutralise virus and inhibit oncolytic activity (48). However prior immunity to HSV does not appear to significantly impair the therapeutic efficacy of herpes simplex therapy in immunocompetent models (49, 50). Further studies of systemic administration HSV 1790 in immunocompetent models are required.

In conclusion, we have demonstrated that the combination of the oncolytic herpes simplex virus HSV1716 with a 'suicide gene therapy' approach can enhance anti-tumor efficacy in comparison with the effects of the oncolytic virus alone. Intravenous administration of HSV1790 results in expression of the ntr transgene in tumor tissues, but not in normal organs, with efficient anti-tumor efficacy following administration of prodrug. As the prototype oncolytic virus HSV1716 has been shown to be totally non-toxic in human patients and has recently entered a Phase III trial, the results presented in this paper lead us to the conclusion that clinical studies of HSV1790 and CB1954 are warranted in patients with otherwise refractory tumors.

REFERENCES

EXAMPLE 1

1. B L Liu, M Robinson, Z-Q Han, R H Branston, C English, Preay, Y McGrath, S K Thomas, M Thornton, P Bullock, C A Love and R S Coffin; Gene Therapy (2003) 10, 292-303.
2. WO 92/13943
3. A Dolán, E Mckie, A R Maclean, D J McGeoch; Journal of General Virology (1992) 73 971-973.
4. Aidan Dolan, Fiona E Jamieson, Charles Cunnigham, Barbara C Barnett Duncan J McGeoch; Journal of Virology March 1998 2010-2021.
5. Joany Chou, Earl R Kern, Richard J Whitley, Bernard Roizman; Science (1990) 250 1262-1265.
6. Coffin R S, MacLean A R, Latchman D S, Brown S M; gene therapy (1996) Oct. 3(10) 886-91.
7. McKie E A, Hope R G, Brown S M, Maclean A R; Journal of General Virology, (1994) April 75(Pt4) 733-41.

8. McKay E M, McVey B, Marsden H S, Brown S M, MacLean A R; Journal of general Virology, (1993) November 74(Pt11) 2493-7.
9. Joany Chou, Bernard Roizman; Journal of Virology; (1990) March 1014-1020.
10. Puchhammer-Stöckl et al, Journal of Medical Virology 32:77-82 (1990).
11. MacLean A R, Parced M I J, Robertson L, Harland J, Brown S M 1991. *J Gen Virol* 72: 631-639.
12. Papanastassiou V, Rampling R, Fraser M, Petty R, Hadley D, Nicoll J, Harland J, Mabbs R, brown S M (2002). *Gene Therapy* 9: 398-406.
13. Rampling R, Cruikshank G, Papanastassiou V, Nicoll J, Hadley D, Brennan D, petty R, MacLean A, Harland J, McKie E, Mabbs R, Brown S M (2000). *Gene Therapy* 7: 859-866.
14. WO 2005/049845
15. Clark et al. Gene Therapy 1997 4 101-110

EXAMPLE 2

1. Hanahan D, Weinberg R A. The hallmarks of cancer. Cell 2000; 100: 57-70.
2. Pardoll D M. Spinning molecular immunology into successful immunotherapy. Nat Rev Immunol 2002; 2: 227-238.
3. Martin L, Lemeoine N. Direct killing by suicide genes. Cancer Metast Rev 1996; 15: 301-306.
4. McGeoch D J, Dolan A, Donald S, Rixon F J. Sequence determination and genetic content of the short unique region in the genome of herpes simplex virus type 1. J Mol Biol 1985 Jan. 5; 181(1):1-13.
5. Glorioso J C, Goins W F, Meany C A, Fink D J, DeLuca N A, Gene Transfer to brain using herpes simplex virus vectors. Ann Neurol 1994; 35: 328434.
6. Dolan A, McKie E, MacLean McGeeoch D J. Status of the ICP34.5 gene in herpes simplex virus type I strain 17. J Gen Virol 1992; 73: 97 1-973.
7. Valgi-Nagy T, Faeed M U, O'Keefe J S et al. The herpes simplex vim type 1 strain 17+ y34.5 deletion mutant 17 16 is avirulent in SCID mice. J Gen. Virol 1994; 75: 2059-2063.
8. Brown S M, MacLean A R, MacKie E A, Harland J. the herpes simplex virulence factor ICP34.5 and the cellular protein MyD116 complex with proliferating cell nuclear antigen through the 63 amino acid domain conserved in ICP34.5, MyD116 and GADD34. J. Virol 1997; 7 1: 9442-9449.
9. Brown S M, Harland J, Maclean A R, Podlech J, Clementi J B. Cell type and cell state determine differential in vim growth of non virulent ICP34.5 negative herpes simplex virus. I. Gen. Virol. 1994; 75: 2367-2377.
10. Coffin R S, MacLean A R, Latchman D S, Brown S M. Gene delivery to the central and peripheral nervous system of mice using a HSV1 ICP34.5 deletion mutant vectors. Gene Ther. 1996; 3: 886-89 1.
11. McKie E A, Graham D I, Brown S M. Selective astrocytic transgene expression in vitro and in vivo from the GFAP promoter in a HSV RL1 null mutant vector-potential glioblastoma targeting. Gene Ther 1998; 5: 440-450.
12. Randazzo B P, Kesari S, Gesser R M eb al. Treatment of experimental intracranial murine melanoma with a neuroattenuated herpes simplex virus 1 mutant. Virology 1995 Aug. 1; 211(1): 94-101.
13. Miller C G, Fraser N W. Role of the immune response during neuro-attenuated herpes simplex mediated tumour destruction in a murine intracranial melanoma model. Cancer Res 2000; 20: 5714-22.
14. Randazzo B P, Bhat M G, Kesari S, Fraser N R, Brown S M. Treatment of experimental subcutaneous human melanoma with a replication restricted herpes simplex mutant. J Invest Dermatol 1997; 108: 933-37.
15. Kucharczuk J C, Randazzo B, Chang M Y et al. Use of a v"replication-restricted" herpes virus to treat experimental human malignant mesothelioma. Cancer Res 1997; 57(3): 466-71.
16. Coukos G, Makrigiannakis A, Kang E H et al. Use of carrier cells to deliver a replication-selective herpes simlex virus-1 mutant for the intraperitoneal therapy of epithelial ovarian cancer. Clin Cancer Res 1999; 5: 1523-1537.
17. Lambright E S, Caparrelli D J, Abbas A E et al Oncolytic therapy using a mutant type-1 herpes simplex virus and the role of the immune system. Ann. Thorac Surg 1999; 68: 1756-1760.
18. Toyoizumi T, Mick R, Abbas A E, Kang A E, Kaiser L R, Molnar-Kimber K L. Combined therapy with chemotherapeutic agents and herpes simplex type 1 ICP34.5 mutant (HSV 17 16) in human non small cell lung cancer. Hum Gene Ther 1999; 10 (1 8):3013-29.
19. Thomas D L, Fraser N R. HSV-I therapy of primary tumours reduces the number of metastases in an immune competent model of metastatic breast cancer. Mol Ther 2003; 8:543-51.
20. Papanastassiou V T, Rampling R, Fraser M et al. The potential for efficacy of the modified (ICP34.5—herpes simplex virus HSV1716 following intratumoural injection into human malignant glioma: a proof of principle study. Gene Ther 2002; 9: 398-406.
21. Rampling R, Cruickshank G, Papanastassiou V et al. Toxicity evaluation of replication competent herpes simplex virus (ICP34.5 null mutant 17 16) in patients with recurrent malignant glioma. Gene Ther 2000; 7: 859-866.
22. Mackie R M, Stewart B J, Brown S M. Intralesional injection of herpes simplex virus 17 16 in patients with metastatic melanoma. Lancet 200 1; 358: 525-526.
23. Harrow S, Papanastassiou V. Harland J, et al. HSVI716 injection into the brain adjacent to tumour following surgical resection of high grade glioma: safety data and long term survival. Gene Ther 2004; 1 1:1648-1658.
24. Greco O, Dacb G U. Gene directed enzyme prodrug therapy of cancer: historical appraisal and future perspectives. J. Cell Physiol 2001; 187: 22-36.
25. Bailey S M, Hart I R. Nitroreductase activation of CB 1954—an alternative 'suicide' gene system. Gene Ther, 1997; 4: 80-8 1.
26. Bailey S M, Knox R J, Hobbs G M et al. Investigation of alternative prodrugs for use with *E. Coli* nitroreductase in 'suicide' gene approaches in cancer therapy. Gene Ther 1996; 3: 1 143-1 150.
27. McNeish I A, Green N J S, Gilligan M G et al. Virus directed enzyme prodrug therapy for ovarian and pancreatic cancer using retrovirally delivered *E. Coli* nitroreductase and CB1954. Gene Ther 1998; 5: 1061-1069.
28. Anlezark G M, Melton R G, Sherwood R F, Coles B, Friedlos F, Knox R J. The bioactivation of 5-(aziridin-1-yl)-2,4dinitrobenzamide (CB1954). Purification and properties of a nitroreductase enzyme from *Escherichia coli*-a potential enzyme for antibody-directed enzyme prodrug therapy (ADEPT). Biochem Pharmacol 1992 Dec. 15; 44(12): 2289-95.

29. Bridgewater J A, Knox W, Pitts J D, Collins J K, Springer C J. The bystander effect of the nitroreductase 1 CB 1954 enzyme/prodrug system is due to a cell permeable metabolite. Human Gene Ther 1997; 6: 709-7 17.
30. Dejha A H, Hulme A, Dexter M T et al. Expression of *Escherichia Coli* B nitroreductase in established human tumour xenografts in mice results in potent antitumoural and bystander effects upon systemic administration of the prodrug CB1954. Cancer Gene Ther 2000; 5: 72 1-73 1.
31. Willis, S H, Peng C, Ponce ce Leon M et al. Expression and purification of secreted forms of HSV glycoproteins from baculovirus—infected insect cells. From Methods in Molecular Medicine, Vol 10: Herpes Simplex Virus protocols. Humana Press Inc, Totowa N.J.
32. Harland J, Brown S M. Preparation of HSV-DNA. From Methods in Molecular Medicine, Vol 10; Herpes Simplex Virus protocols Chapter 2. Humana Press Inc, Totowa N.J.
33. Towbin H, Staehelin T, Gordon J. Electrophoretic transfer of proteins from poly acrylmide gels to nitrocellulose sheets: procedure and some applications. PNAS1979; 76: 43504354,
34. Puchhammer-St6ckl E, Popow-Mpp T, Heinz F X, Mandl C W, Kunz C. Establishment of PCR for the early diagnosis of herpes simplex encephalitis. J Med Virology 1990; 32: 77-82.
35. Clark A J, Iwobi M, Cui W et al. Selective cell ablation in transgenic mice expression *E, Coli* nitroreductme. Gene Ther 1997 February; 4(2): 10 1-10.
36. Weise C C, Williams A, Olesch J, Kh D H, Efficacy of a replication-competent adenovirus (ONYX-015) following intratumoural injection: intratumoural spread and distribution effects. Cancer Gene Ther 1999; 6: 499-504.
37. Anthoney, D A, McIlwrath Aj, Gallagher W M, Edlin A R M, Brown R. Microsatellite instability, apoptosis and loss of p53 function in drug resistant tumour cells, Cancer Res 1996; 56: 1374-1381.
38. Strathdee G, MacKeen M J, Illand M, Brown R. A role for methylation of the hMLH1 promoter in loss of hMLH 1 expression and drug resistance on ovarian cancer. Oncogene 1999; 18: 2335-2341.
39. Bilsland A E, Anderson C J, Fletcher-Monaghan A J ef al. Selective ablation of human, cancer cells by telomerase-specific adenoviral suicide gene therapy vectors expressing bacterial nitroreductase, Oncogene 2003; 22: 370-380.
40. Freytag S O, Roguiski K R, Paielli D L, Gilbert J D, Kim J H. A novel three-pronged approach to kill cancer cells selectively: Concomitant viral, double suicide gene, and radiotherapy. Human Gene Ther 1998; 9: 1323-1333.
41. Rogulski K R, Wing M S, Paielli D L, et al. Double suicide gene therapy augments the antitumour activity of a replication-competent lytic adenovirus through enhanced cytotoxicity and radiosensitization. Human Gene Ther 2000; 11: 67-76.
42. Lorence R M, Pecora A L, Major P P et d, Overview of phase I studies of intravenous administration of PV701, an oncolytic virus. Curr Opin Mol Ther 2003; 5: 618-624.
43. Percora A L, Rimi N, Cohen G I et al. Phase I trial of intravenous administration of PV70 1, an oncolytic virus, in patients with advanced solid cancers. J. Clin Oncol 2002; 20: 225 1-2266,
44. Reid T, Warren R, Kirn D. Intravascular adenoviral agents in cancer patients: lessons from clinical trials. Cancer Gene Ther. 2002; 9: 978-986.
45. Reid T, Galanis E, Abbruzzese J et al. Intra-arterial administration of a replicationselective adenovirus (dl1520) in patients with colorectal carcinoma metastatic to the liver: a phase I trial. Gene Ther. 200 1; 8: 16 18-1626.
46. Toda M, Rabkin S D, Kojima H, Martuza R L. Herpes simplex virus as an in situ cancer vaccine for the induction of a specific anti-tumour immunity. Human Gene Ther 1999; 10: 385-393.
47. Wong Rj, Chan, M K, Yu Z et al Effective intravenous therapy of murine pulmonary metastases with an oncolytic herpes simplex virus expressing Interleukin 12. Clin Cancer Res 2004; 10: 25 1-259.
48. Hirasawa K, Nishikawa S G, Norman K L et al. Systemic roevirus therapy of metastatic cancer in immune competent mice. Cancer Res 2003; 63; 348-353.
49. Chahlavi A, Rabkin S, Todo T et al. Effect of prior exposure to herpes simplex 1 on viral vector-mediated tumor therapy in immunocompetent mice. Gene Ther 1999; 6: 1751-1758.
50. Lambright E S, Kang E H, Force S et al. Effect of pre-existing anti-herpes immunity on the efficacy of herpes simplex therapy in a murine intraperitoneal tumour model. Mol Ther 2000; 4: 387-93.

The invention claimed is:

1. A kit of parts for use in treating a tumour in a human patient by combination therapy, said kit comprising a first container containing an herpes simplex virus (HSV-1) and a second container comprising a pharmaceutical, wherein the pharmaceutical is an activatable nitroreductase (NTR) prodrug and the HSV-1 genome encodes an expressible nitroreductase polypeptide capable of converting the activatable NTR prodrug to a therapeutically active pharmaceutical, and wherein the HSV-1 comprises a deletion, addition, substitution or insertion in each ICP34.5 gene, the kit further comprising instructions for the therapeutically effective administration of said HSV-1 and/or pharmaceutical to a human patient in need of treatment at an extratumoural location in order to treat the tumour, and wherein the tumor is a type that is capable of being treated with an alkylating agent.

2. The kit of claim 1 wherein the NTR prodrug is CB1954.

3. The kit of claim 1 wherein the nucleotide sequence encoding said polypeptide is located entirely within, or so as to overlap, the ICP34.5 encoding nucleotide sequence of the HSV genome.

4. A method of treating a tumour in a human comprising the steps of administering to an individual human in need of treatment a therapeutically effective amount of a pharmaceutical, wherein the pharmaceutical is an nitroreductase (NTR) activatable prodrug, and a therapeutically effective amount of an herpes simplex virus (HSV-1) wherein the HSV-1 genome encodes an expressible nitroreductase polypeptide capable of converting the NTR activatable prodrug wherein the HSV-1 comprises a deletion, addition, substitution or insertion in each ICP34.5 gene, and wherein the HSV-1 is administered at an extratumoural location, and wherein the tumor is a type that is capable of being treated with an alkylating agent.

5. The method of claim 4 wherein the method involves simultaneous, separate or sequential administration of the HSV and activatable prodrug.

6. The method of claim 4 wherein the NTR prodrug is CB 1954.

7. The method of claim 4 wherein the nucleotide sequence encoding said nitroreductase is located entirely within, or so as to overlap, the ICP34.5 encoding nucleotide sequence of the HSV genome.

8. The method of claim 7 wherein the NTR prodrug is CB1954.

9. The method of claim 4 wherein the extratumoural administration is into a circulating fluid of the patient.

10. The method of claim 4 wherein the extratumoural administration is into the patient's blood.

11. The method of claim 4 wherein said activatable prodrug is administered directly to the tumour.

12. The method of claim 4 wherein said HSV and activatable prodrug are administered at the same extratumoural location.

13. The method of claim 4 wherein said HSV and activatable prodrug are administered to the same circulating fluid.

14. The method of claim 4 wherein said HSV and activatable prodrug are administered at different extratumoural locations.

15. The method of claim 4 wherein the HSV is non-neurovirulent.

16. The method of claim 4 wherein the HSV is oncolytic.

17. The method of claim 4 wherein the HSV has an inactivating mutation in one or each ICP34.5 locus of the HSV genome.

18. The method of claim 4 wherein the HSV has a mutation in each ICP34.5 locus such that the HSV cannot express a functional ICP34.5 gene product.

19. The method of claim 4 wherein the HSV is an ICP34.5 null mutant.

20. The method of claim 4 wherein the HSV is an HSV of strain 17.

21. The method of claim 4 wherein the HSV is a mutant of HSV1716.

22. The method of claim 4 wherein the HSV is HSV 1790 deposited under ECACC accession number 03110501.

* * * * *